US009477906B2

(12) United States Patent
Röder et al.

(10) Patent No.: US 9,477,906 B2
(45) Date of Patent: Oct. 25, 2016

(54) CLASSIFICATION GENERATION METHOD USING COMBINATION OF MINI-CLASSIFIERS WITH REGULARIZATION AND USES THEREOF

(71) Applicant: Biodesix, Inc., Boulder, CO (US)

(72) Inventors: Heinrich Röder, Steamboat Springs, CO (US); Joanna Röder, Steamboat Springs, CO (US)

(73) Assignee: Biodesix, Inc., Boulder, CO (US)

( * ) Notice: Subject to any disclaimer, the term of this patent is extended or adjusted under 35 U.S.C. 154(b) by 178 days.

(21) Appl. No.: 14/486,442

(22) Filed: Sep. 15, 2014

(65) Prior Publication Data

US 2015/0102216 A1    Apr. 16, 2015

Related U.S. Application Data

(60) Provisional application No. 61/975,259, filed on Apr. 4, 2014, provisional application No. 61/878,110, filed on Sep. 16, 2013.

(51) Int. Cl.
*G06K 9/62* (2006.01)
*G06F 19/24* (2011.01)
(Continued)

(52) U.S. Cl.
CPC .......... *G06K 9/6227* (2013.01); *A61B 5/7264* (2013.01); *G06F 19/24* (2013.01); *G06K 9/00147* (2013.01); *H01J 49/0036* (2013.01); *H01J 49/26* (2013.01)

(58) Field of Classification Search
USPC ................................................ 250/282, 281
See application file for complete search history.

(56) References Cited

U.S. PATENT DOCUMENTS 7,736,905 B2 * 6/2010 Roder ................... G06F 19/24
435/372
9,279,798 B2 * 3/2016 Roder ................. G01N 33/487
(Continued)

OTHER PUBLICATIONS

Srivastava, "Improving Neural Networks with Dropout", Master Thesis submitted 2013.
(Continued)

*Primary Examiner* — Kiet T Nguyen
(74) *Attorney, Agent, or Firm* — McDonnell Boehnen Hulbert & Berghoff LLP

(57) ABSTRACT

A method for classifier generation includes a step of obtaining data for classification of a multitude of samples, the data for each of the samples consisting of a multitude of physical measurement feature values and a class label. Individual mini-classifiers are generated using sets of features from the samples. The performance of the mini-classifiers is tested, and those that meet a performance threshold are retained. A master classifier is generated by conducting a regularized ensemble training of the retained/filtered set of mini-classifiers to the classification labels for the samples, e.g., by randomly selecting a small fraction of the filtered mini-classifiers (drop out regularization) and conducting logistical training on such selected mini-classifiers. The set of samples are randomly separated into a test set and a training set. The steps of generating the mini-classifiers, filtering and generating a master classifier are repeated for different realizations of the separation of the set of samples into test and training sets, thereby generating a plurality of master classifiers. A final classifier is defined from one or a combination of more than one of the master classifiers.

39 Claims, 34 Drawing Sheets

(51) Int. Cl.
    *A61B 5/00*    (2006.01)
    *G06K 9/00*    (2006.01)
    *H01J 49/00*   (2006.01)
    *H01J 49/26*   (2006.01)

(56) References Cited

U.S. PATENT DOCUMENTS

2003/0017481 A1   1/2003   Golub
2007/0269804 A1   11/2007  Liew
2015/0283206 A1*  10/2015  Roder .................. A61K 38/179
                                                    514/9.6

OTHER PUBLICATIONS

International Search Report dated May 7, 2015, for corresponding PCT application No. PCT/US2014/055633.
Helmbold et al., "On the Inductive Bias of Dropout", eprint arXiv:1412.4736, 2015.
Wager et al., "Dropout Training as Adaptive Regularization", C. Burges, L. Bottou, M. Welling, Z. Ghahramani, K. Weinberger (Eds.), Advances in Neural Information Processing Systems, vol. 26 (2013), pp. 351-359.
Baldi et al., "The Dropout Learning Algorithm", Aritifical Intelligence, 210:78-122 (2014).
International Preliminary Report on Patentability for corresponding PCT application No. PCT/US2014/055633, dated Mar. 22, 2016.
Van De Vijver et al., "A Gene-Expression Signature as a Predictor of Survival in Breast Cancer", The New England of Journal Medicine, 347(25):1999-2009 (2002).
van't Veer et al.,, "Geen expression profiling predicts clinical outcome of breast cancer", Nature, 415:530-536 (2002).
Tusher et al., "Significance analysis of microarrays applied to the ionizing radiation response", PNAS, 98(9):5116-5121 (2001).
Venet et al., "Most Random Gene Expression Signatures are Significant Breast Cancer Outcome"; PLOS Computational Biology, 7(10):e10021240 (2011).
Elkan, "Maximum Likelihood, Logistic Regression, and Stochastic Gradient Training", elkan@cs.ucsd.edu, (2013).
"Clinical Review Criteria: MammaPrint Test (Gene-Expression Profiling Test, 70-Gene Prognostic Signature) for Predicitn Risk of Cancer Recurrence" (2014).
Wager et al., "Dropout Training as Adaptive Regularization", arXiv:1307.1493[stat.ML] (2013).
Hinton et al., "Improving neural networks by preventing co-adaptation of feature detectors", arXiv:1307.1493[stat.ML] (2012).
Wang et al., "Fast "dropout" training for logistic regression"; Neural Information Processing Systems 2012 Workshop on Log-Linear Models.
"Logistic Regression", (2011), http://classes.engr.oregonstate.edu/eecs/winter2011/cs434/notes/Logistic-regression-7.pdf.
Wang et al., "Fast dropout training", International Conference on Machine Learning (2013).
Girosi et al, "Regularization Theory and Neural Networks Architectures", Neural Computation, 7:219-269, (1995).
Tikhonov, "On the Stability of Inverse Problems", Comptes Rendus (Doklady) de l'Academie des Sciences de l'URSS, vol. XXXIX, N. 5 (1943).
Tibshirani, "Regression Shrinkage and Selection via the Lasso", J.R. Statist. Soc. B, 58(1):267-288 (1996).
Bay, "Nearest neighbor classification from multiple feature subsets", Intelligent Data Analysis, 3:191-209 (1999).
Rokach, "Ensemble-based classifiers", Artif Intell Rev, 33:1-39 (2010).
Seewald et al., "An Evaluation of Grading Classifiers", LNCS 2189, pp. 115-124 (2001).

* cited by examiner

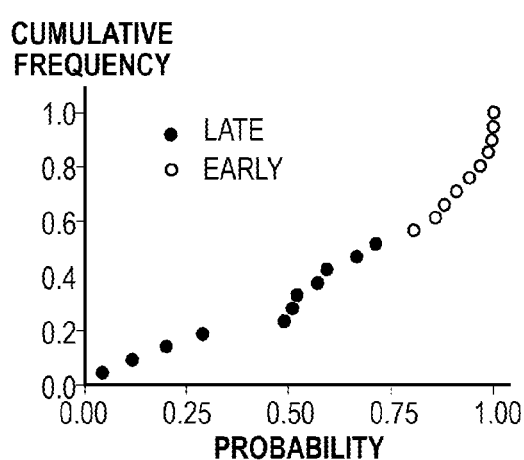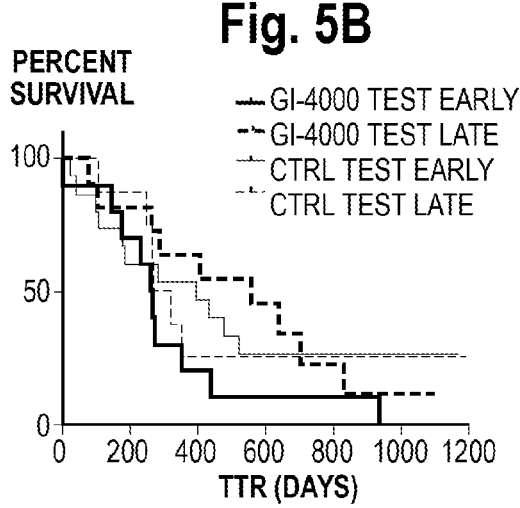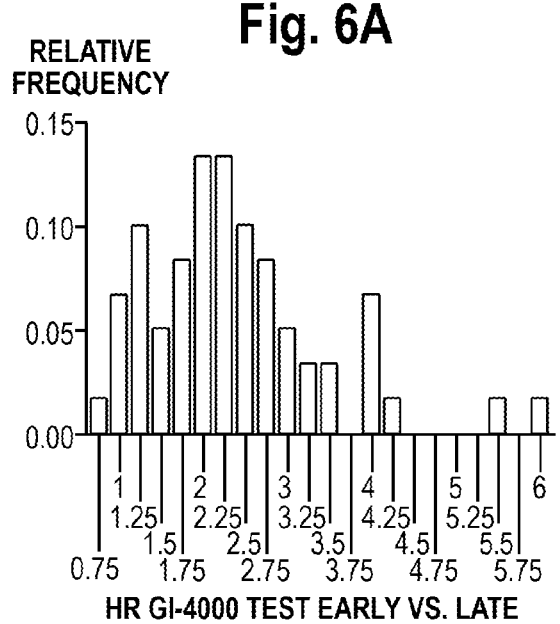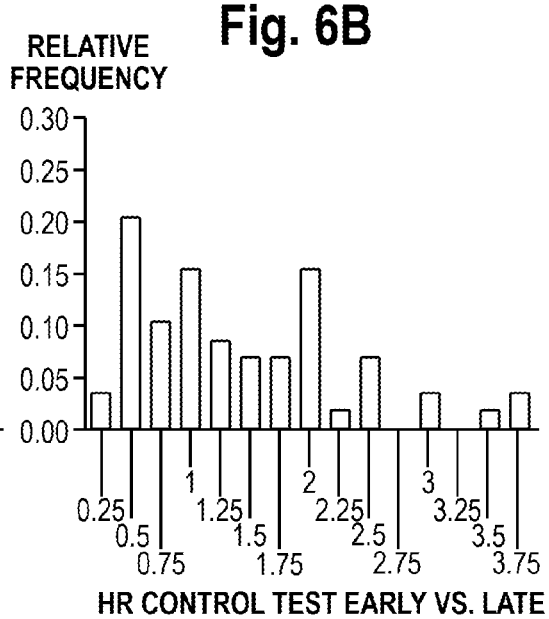

Fig. 7A
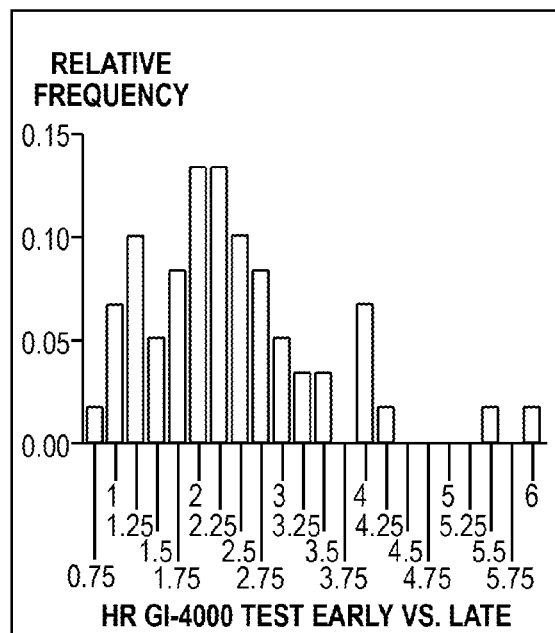
Fig. 7B
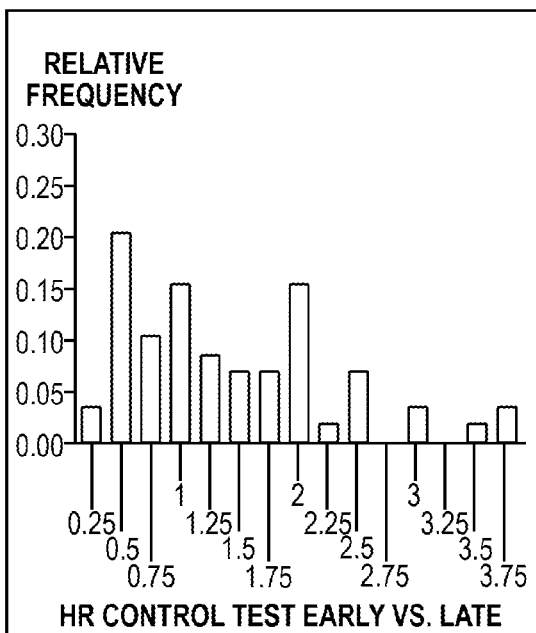
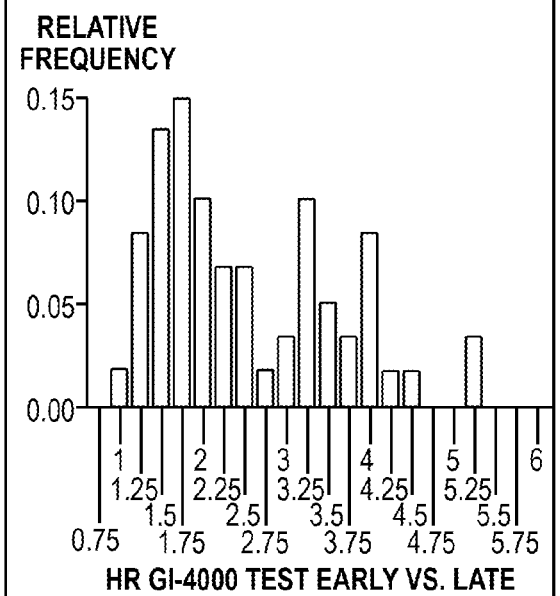
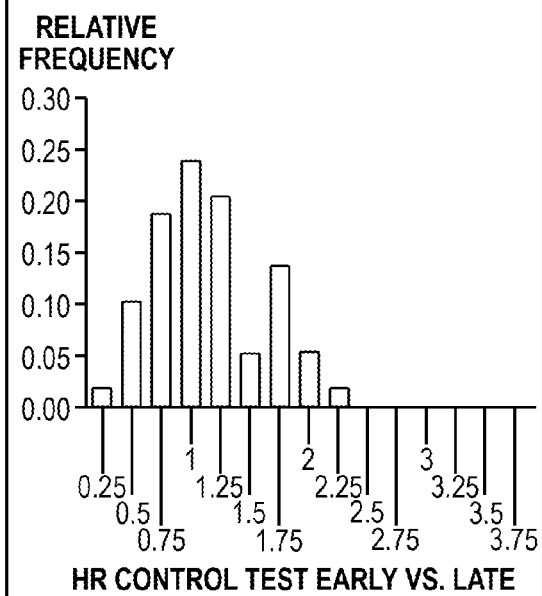

HR GI-4000 EARLY VS. LATE: 3.6
HR CONTROL EARLY VS. LATE: 1.4
HR LATE CONTROL VS. GI-4000: 1.1

HR GI-4000 EARLY VS. LATE: 3.3
HR CONTROL EARLY VS. LATE: 1.6
HR LATE CONTROL VS. GI-4000: 1.3

HR GI-4000 EARLY VS. LATE: 3.5
HR CONTROL EARLY VS. LATE: 1.5
HR LATE CONTROL VS. GI-4000: 1.3

HR GI-4000 EARLY VS. LATE: 4.4
HR CONTROL EARLY VS. LATE: 1.1
HR LATE CONTROL VS. GI-4000: 1.4

MEDIAN TTR
GI-4000 EARLY    266 DAYS
GI-4000 LATE     631 DAYS
CONTROL EARLY    352 DAYS
CONTROL LATE     280 DAYS
HR LATE GI-4000 VS. CONTROL 1.2
HR GI-4000 EARLY VS. LATE 3.4

MEDIAN OS
GI-4000 EARLY    500 DAYS
GI-4000 LATE     1274 DAYS
CONTROL EARLY    849 DAYS
CONTROL LATE     755 DAYS
HR LATE GI-4000 VS. CONTROL 1.5
HR GI-4000 EARLY VS. LATE 4.8

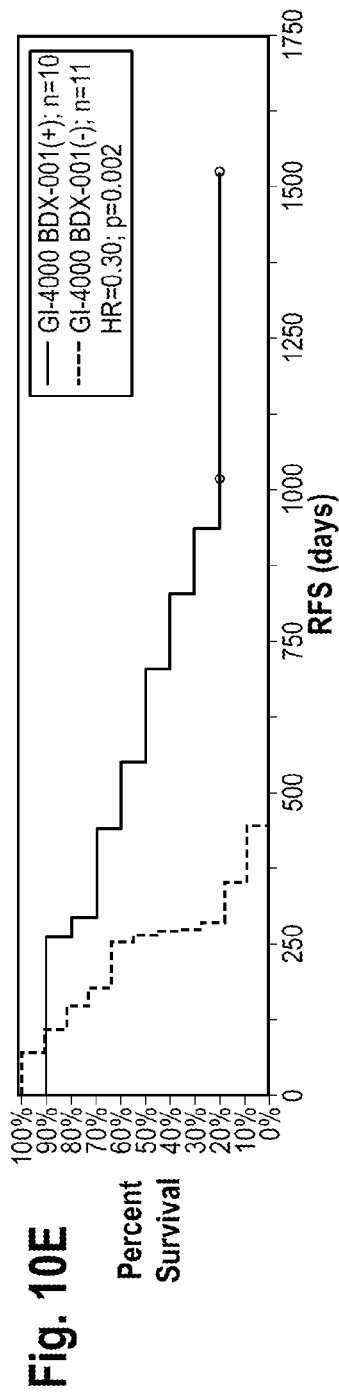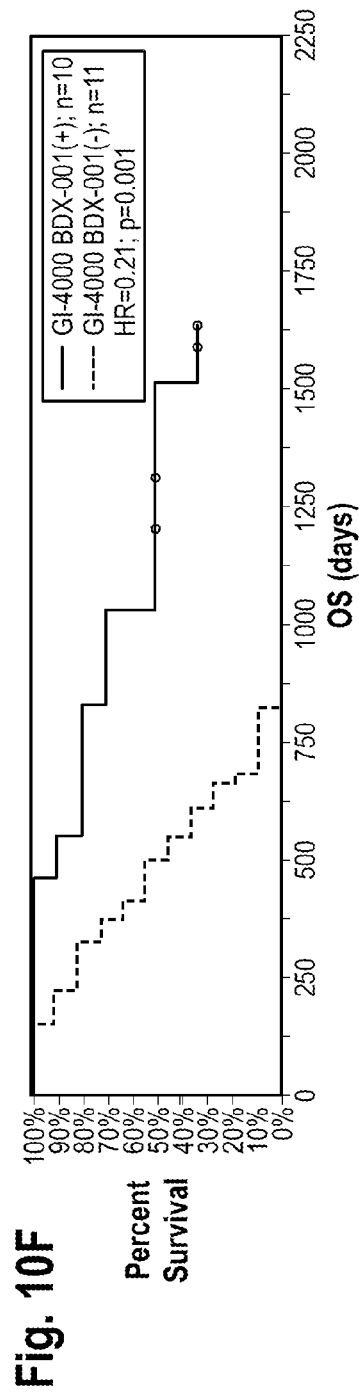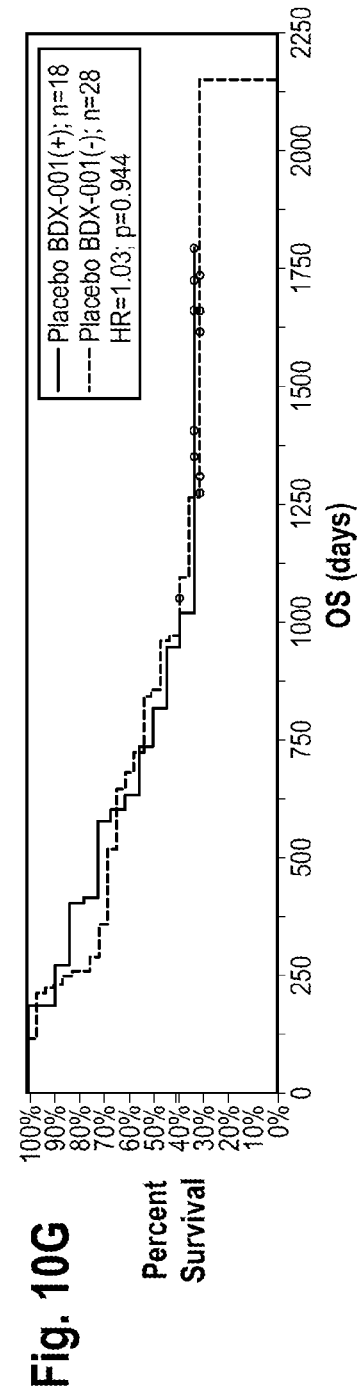

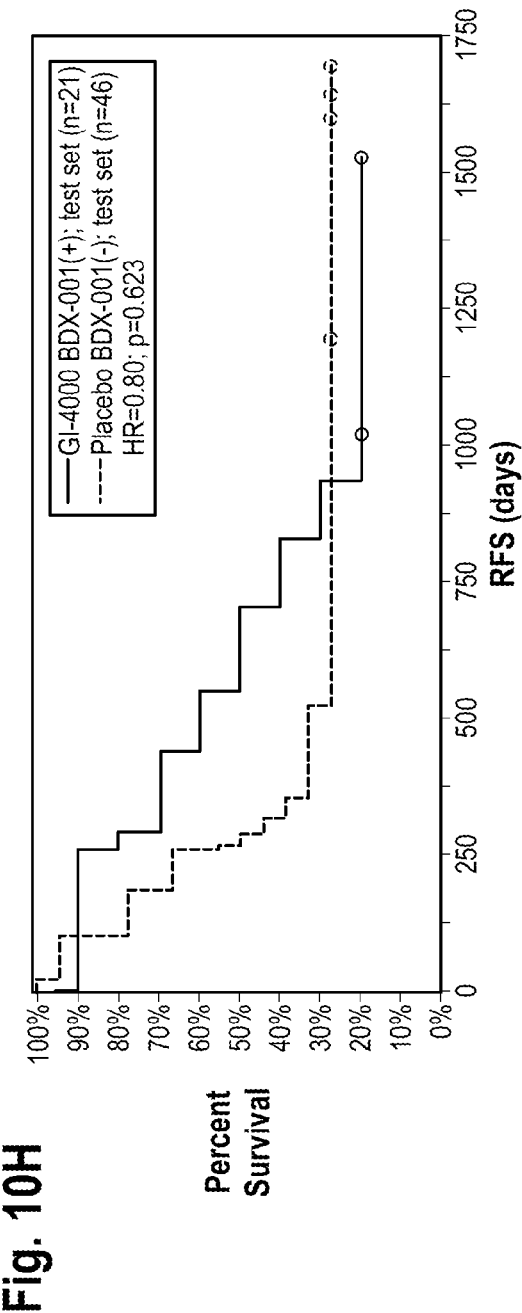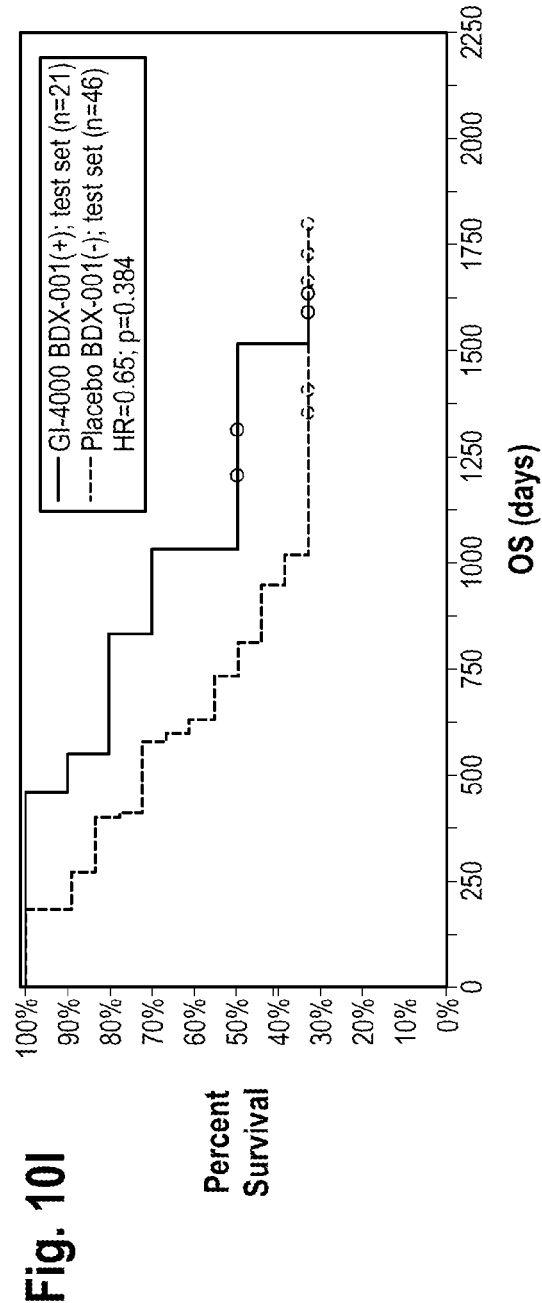
Fig. 10H
Fig. 10I

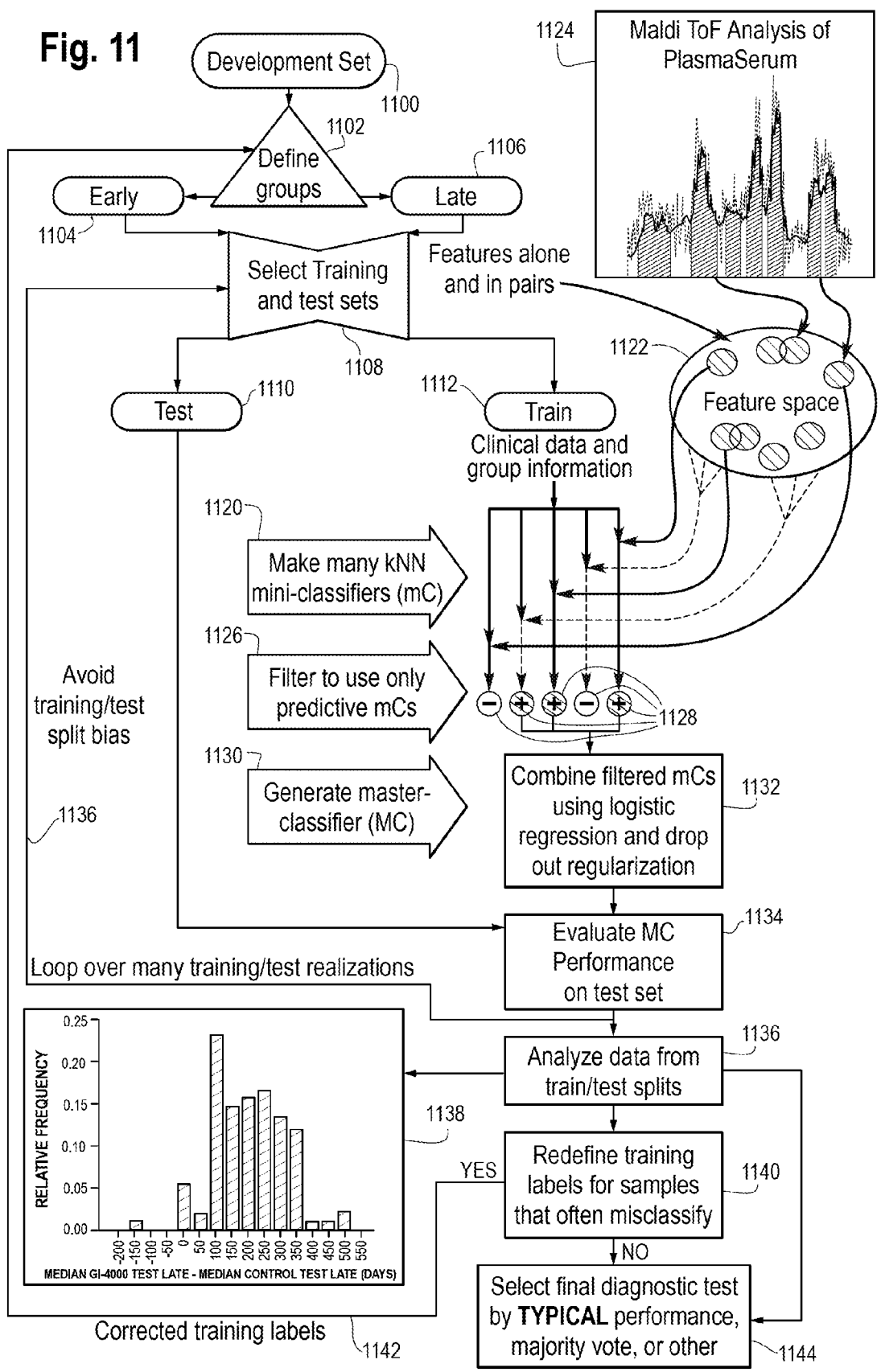

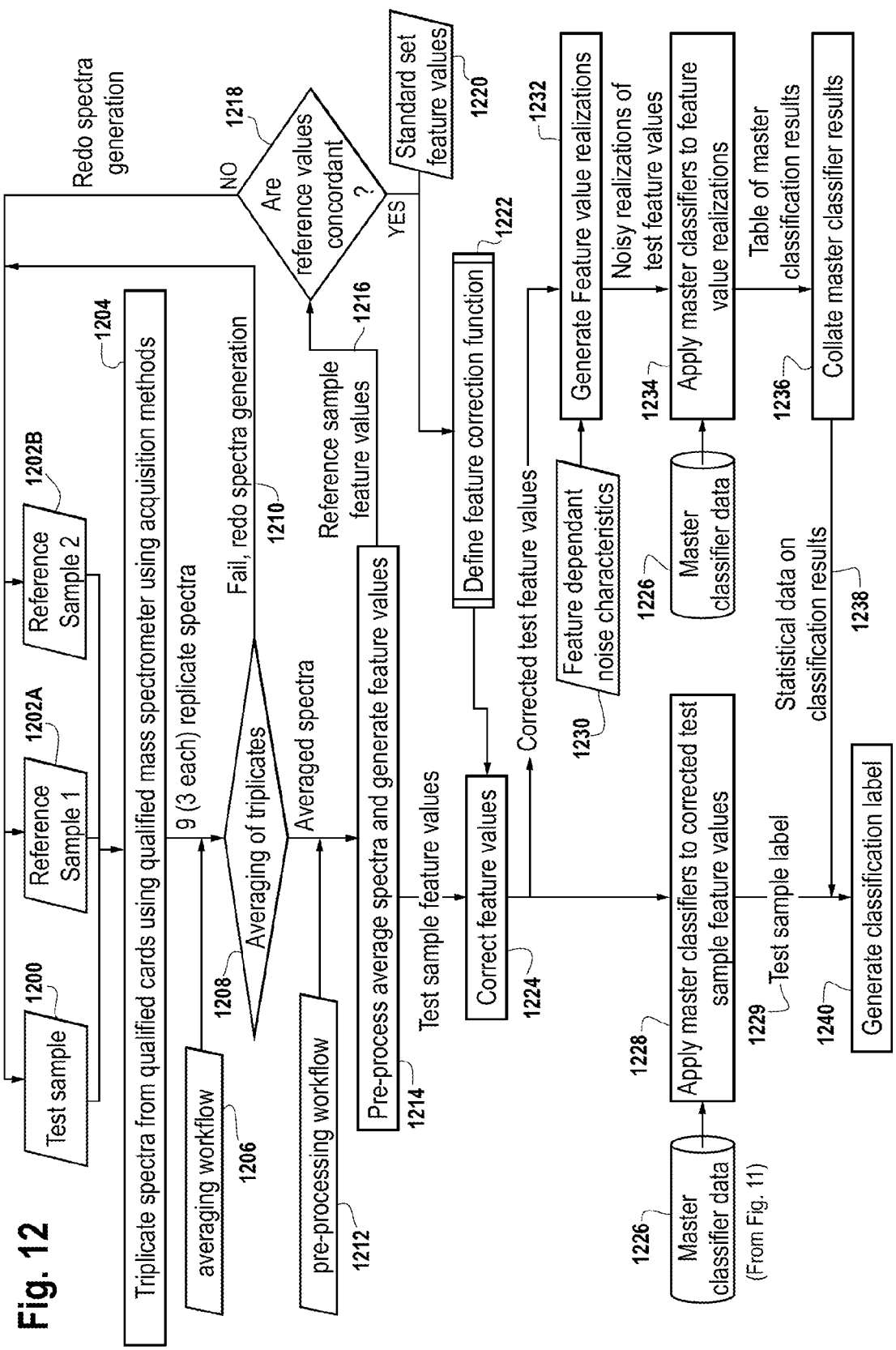

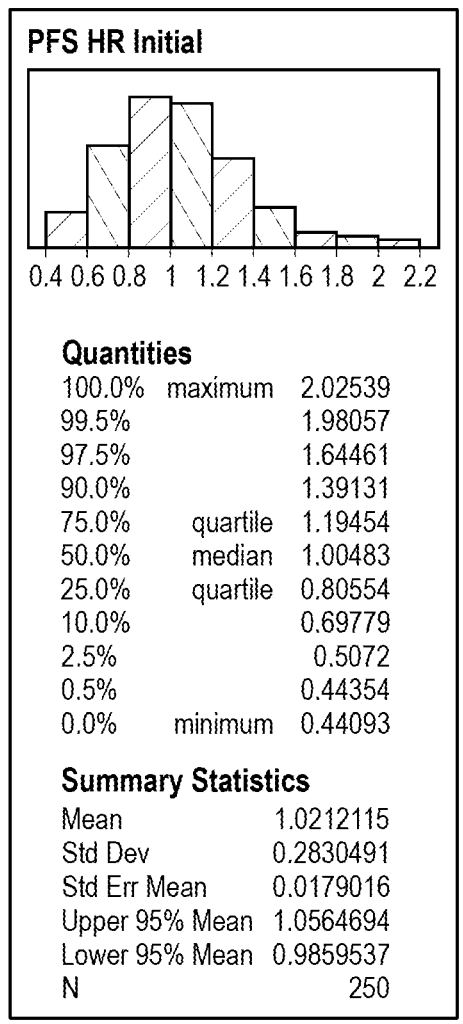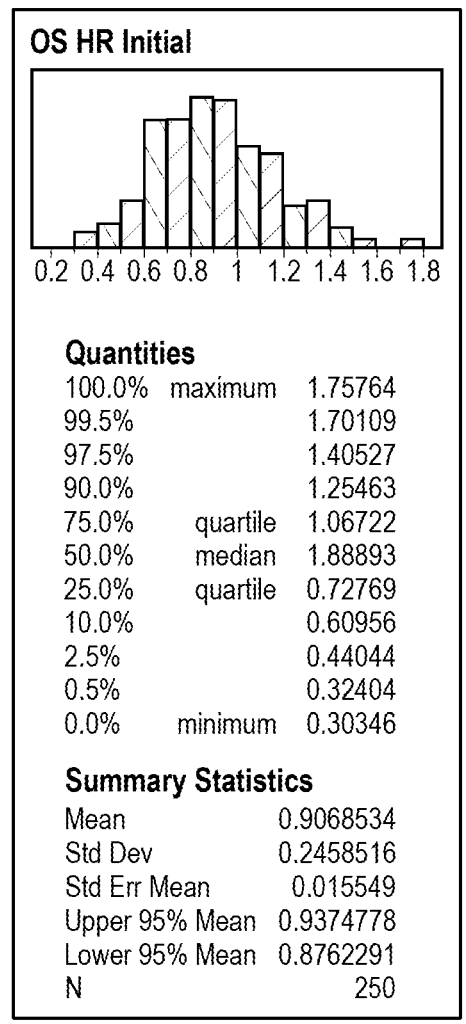
Fig. 14A
Fig. 14B
PFS HR Initial
0.4 0.6 0.8 1 1.2 1.4 1.6 1.8 2 2.2
Quantities
100.0%   maximum   2.02539
99.5%              1.98057
97.5%              1.64461
90.0%              1.39131
75.0%   quartile   1.19454
50.0%   median     1.00483
25.0%   quartile   0.80554
10.0%              0.69779
2.5%               0.5072
0.5%               0.44354
0.0%    minimum    0.44093
Summary Statistics
Mean              1.0212115
Std Dev           0.2830491
Std Err Mean      0.0179016
Upper 95% Mean    1.0564694
Lower 95% Mean    0.9859537
N                       250
OS HR Initial
0.2 0.4 0.6 0.8 1 1.2 1.4 1.6 1.8
Quantities
100.0%   maximum   1.75764
99.5%              1.70109
97.5%              1.40527
90.0%              1.25463
75.0%   quartile   1.06722
50.0%   median     1.88893
25.0%   quartile   0.72769
10.0%              0.60956
2.5%               0.44044
0.5%               0.32404
0.0%    minimum    0.30346
Summary Statistics
Mean              0.9068534
Std Dev           0.2458516
Std Err Mean      0.015549
Upper 95% Mean    0.9374778
Lower 95% Mean    0.8762291
N                       250

HR (95% CI): 0.49 (0.29-0.83)
log-rank p = 0.007    CPH p = 0.008
Median: Early/Unknown (VS-G): 9.6 months
    Late: 17.1 months HR (95% CI): 0.83 (0.44-1.55)
log-rank p = 0.545    CPH p = 0.548
Median: Early/Unknown (VS-G): 10.9 months
    Late: 15.1 months HR (95% CI): 0.48 (0.28-0.80)
log-rank p = 0.004    CPH p = 0.005
Median: Early/Unknown (VS-G): 2.3 months
          Late: 3.9 months HR (95% CI): 0.78 (0.44-1.37)
log-rank p = 0.375    CPH p = 0.380
Median: Early/Unknown (VS-G): 4.7 months
          Late: 6.1 months HR (95% CI): 0.67 (0.32-1.42)
log-rank p = 0.294    CPH p = 0.294
Median: Late CT:    15.1 months
        Late ERL: 17.1 months HR (95% CI): 0.93 (0.47-1.84)
log-rank p = 0.830    CPH p = 0.830
Median: Late CT:    6.1 months
        Late ERL: 3.9 months

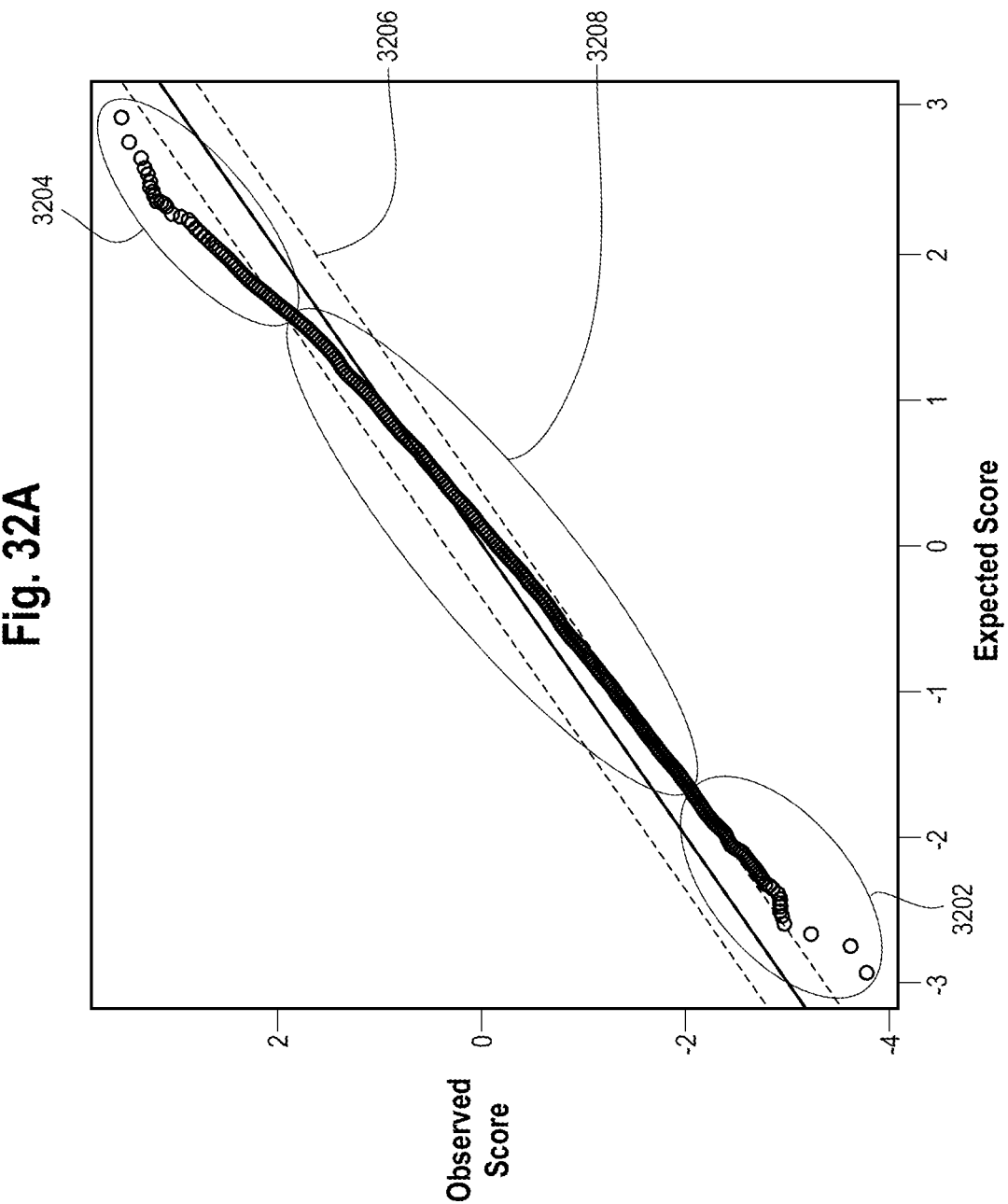

CLASSIFICATION GENERATION METHOD USING COMBINATION OF MINI-CLASSIFIERS WITH REGULARIZATION AND USES THEREOF

CROSS-REFERENCE TO RELATED APPLICATIONS

This application claims priority benefits under 35 U.S.C. §119(e) to prior U.S. provisional application Ser. No. 61/975,259 filed Apr. 4, 2014, and to prior U.S. provisional application Ser. No. 61/878,110 filed Sep. 16, 2013, the content of each of which is incorporated by reference herein.

FIELD

This disclosure relates to a method and system for generating classifiers for performing classification of samples, e.g., biological samples. It features a combination of filtered atomic or "mini" classifiers combined in accordance with a regularized combination method, for example by logistic training to classification group labels and dropout regularization, and generation of a master classifier from the filtered mini-classifiers after logistic regression training and drop out regularization.

In contrast to standard applications of machine learning focusing on developing classifiers when large training data sets are available, the big data challenge, in bio-life-sciences the problem setting is different. Here we have the problem that the number, n, of available samples is limited arising typically from clinical studies, and the number of attributes (measurements) associated with each sample, p, usually exceeds the number of samples. Rather than obtaining information from many instances, in these deep data problems one attempts to gain information from a deep description of individual instances. The present methods work particularly well in classification problems where p>>n, as will be demonstrated in the examples in the detailed description.

BACKGROUND

A previous patent application of the present inventors, U.S. Ser. No. 13/835,909 filed Mar. 15, 2013, describes classification of mass spectrometry data of blood-based samples to predict cancer patient benefit from yeast-based immunotherapy, including GI-4000, a drug developed by GlobeImmune, Inc., Louisville Colo. The entire content of the '909 application is incorporated by reference herein. The description of the Deep MALDI mass spectrometry methods in that document, as well as U.S. Ser. No. 13/836,436 filed Mar. 15, 2013, also incorporated by reference herein. The interested reader is specifically directed to that section of the '909 application and the '436 application for reference.

Briefly, GI-4000 is a yeast based immunotherapy targeted at RAS mutations common in pancreatic cancer. GlobeImmune conducted a Phase II study to evaluate the efficacy of this treatment in combination with gemcitabine compared to gemcitabine alone in the adjuvant setting. While the overall result was ambiguous, there were hints of benefit from GI-4000 in some subgroups. Detailed analysis of follow-up data also showed that GI-4000 did stimulate yeast-specific immune response in some patients.

The inventors' assignee, Biodesix, Inc. (Boulder Colo.) has developed advanced mass spectrometry analysis techniques which, in combination with sophisticated data analysis algorithms and novel learning theory approaches, enable the development of predictive assays from serum or plasma samples. These techniques have led to the development of a commercially available assay, VeriStrat®, clinically used in the prediction of erlotinib resistance in second line non-small cell lung cancer from pre-treatment samples. The VeriStrat test is described at length in U.S. Pat. No. 7,736,905, the content of which is incorporated by reference herein.

We applied the Biodesix assay development platform to samples from the GI-4000 trial to develop a test to select patients who would benefit from the addition of GI-4000 to gemcitabine in the adjuvant treatment of pancreatic cancer. While previous attempts at this problem showed promise, performance estimates were limited to cross-validation results due to the small size of the available sample set.

A new classifier generation method was developed as explained in this document. As explained below, using newly developed training algorithms we were able to split the available samples into proper training and test sets. This greatly enhances our confidence in the generalizability of the development results. This document, in Example 1, describes the results and methods used in the development of a predictive test for patient benefit for GI-4000+gemcitabine as an example of the generation and use of the classifier development methodology described herein.

A further example of development of a classifier and method for predicting patient benefit from anti-cancer drugs is also described. This example is in the context of non-small cell lung cancer (NSCLC), epidermal growth factor receptor inhibitors (EGFR-Is) and chemotherapy drugs.

A further example is described in which a classifier is generated from genomic data, in this example messenger RNA (mRNA) transcript expression levels from tumor samples from humans with breast cancer. The classifier is predictive of whether a breast cancer patient is at risk of early relapse.

However, as will be appreciated from the following discussion, the methodology is of general applicability to classification problems, especially those where p>n and the following detailed descriptions are offered by way of example and not limitation.

SUMMARY

In a first aspect, a method for generating a classifier is described below. The method includes a step a) of obtaining physical measurement data for classification from a plurality of samples (e.g., blood, tissue, or other type of biological sample). The data for classification for each of the samples consists of a multitude of feature values (e.g., integrated intensity values at particular m/Z ranges in mass spectrometry data, fluorescence intensity measurements associated with mRNA transcript, protein, or gene expression levels) and an associated class or group label. The class or group label can take various forms (the particular moniker not being particularly important); it can be iteratively defined in generation of the classifier, and in some embodiments may have some diagnostic or therapeutic meaning or attribute.

The method continues with a step b) of constructing a multitude of individual mini-classifiers using sets of feature values from the samples up to a pre-selected feature set size (s, integer). For example, mini-classifiers are constructed for individual features (s=1) and/or pairs of features (s=2). For example, if the initial feature set contains 100 features, the number of mini-classifiers for s=1 would be 100, and for s=2 would be 4950=100*99/2. The mini-classifiers execute a classification algorithm, such as k-nearest neighbors, in which the values for a feature or pairs of features of a sample instance are compared to the values of the same feature or features in a training set and the nearest neighbors (e.g., k=5) in feature space are identified and by majority vote a class label is assigned to the sample instance by each mini-classifier. Other supervised classification methods could be used as an alternative to k-nearest neighbors, e.g., tree-based classification, linear discriminants, support vector machines, etc. It will be understood that one could use larger values of s, and the number of possible feature combinations would increase resulting in larger computational resource requirements.

The method continues with step c) of testing the performance of individual mini-classifiers to classify at least some of the multitude of biological samples (e.g., a training set, a subset of an entire development set), and retaining only those mini-classifiers whose classification accuracy or predictive power, or any suitable other performance metric, exceeds a pre-defined threshold, to thereby arrive at a filtered (pruned) set of mini-classifiers.

The method continues with step d) of generating a master classifier by combining the filtered mini-classifiers using a regularized combination method. In one embodiment, this regularized combination method takes the form of repeatedly conducting a logistic training of the filtered set of mini-classifiers to the class labels for the samples. This is done by randomly selecting a small fraction of the filtered mini-classifiers as a result of carrying out an extreme dropout from the filtered set of mini-classifiers (a technique referred to as drop-out regularization herein), and conducting logistical training on such selected mini-classifiers.

In step e) of the method, the samples are a set of samples which are randomly separated into a test set and a training set, and the steps b)-d) are repeated in the programmed computer for different realizations of the separation of the set of samples into test and training sets, thereby generating a plurality of master classifiers, one for each realization of the separation of the set of samples into training and test sets.

The method continues with step f) of defining a final classifier from one or a combination of more than one of the plurality of master classifiers. The final classifier can be defined in a variety of ways, including by selection of a single master classifier from the plurality of master classifiers having typical or representative performance, by majority vote of all the master classifiers, by modified majority vote (explained below), by weighted majority vote, or otherwise.

The methodology has potentially wide application to a variety of possible classification problems in the biological sciences and with different types of sample data. In this document, we describe several examples of the classifier generation methodology and uses thereof from mass spectrometry data. We also describe an example in which a classifier is developed from genomic data, in this example mRNA transcript expression levels from a tissue sample. The classifiers thus developed can be used for predictive tests. In one example, the method generates a classifier for classification of blood-based samples into one of two classes as a test to predict whether a pancreatic cancer patient is likely to obtain benefit from a combination of drugs, in this case a yeast-based immunotherapy drug (GI-4000)+gemcitabine in treatment of pancreatic cancer. Another example generates a classifier for classification of mass spectra from blood-based samples into one of three classes to guide treatment of non-small cell lung cancer (NSCLC) patients, including prediction of whether a patient is likely to obtain more benefit from an epidermal growth factor receptor inhibitor (EGFR-I) than from chemotherapy drugs. In the genomic example, the classifier predicts whether a breast cancer patient is at risk from an early relapse of the breast cancer.

In another aspect, a classification generation system is described comprising a general purpose computer having a processing unit and a memory storing data for classification of a multitude of samples, the data for each of the samples consisting of a multitude of feature values and a class label. The memory stores program code for: 1) constructing a multitude of individual mini-classifiers using sets of features from the samples up to a pre-selected feature set size (s, integer); 2) testing the performance of individual mini-classifiers to classify at least some of the multitude of biological samples and retaining those mini-classifiers whose classification accuracy, or other performance metric, exceeds a pre-defined threshold to arrive at a filtered set of mini-classifiers; 3) generating a master classifier by combining the filtered mini-classifiers using a regularized combination method; 4) repeating steps 1)-3) for different realizations of the separation of the set of samples into test and training sets, thereby generating a plurality of master classifiers, one for each realization of the separation of the set of samples into training and test sets, and 5) defining a final classifier from one or a combination of more than one of the plurality of master classifiers.

In one embodiment, the program code executing the combining step 3) repeatedly conducts a logistic training of the filtered set of mini-classifiers to the classification labels for the samples by randomly selecting a small fraction (extreme dropout) of the filtered mini-classifiers and conducting logistical training on such selected mini-classifiers. Other regularized combination methods can also be used, as explained in further detail below. The final classifier can be defined in various ways, for example, as a weighted average of the collection of master classifiers, as one of the master classifiers from a particular training/test set split showing "typical" performance, as a majority vote of the master classifiers from an ensemble of training/test splits of the sample set data, or otherwise.

The classification generation system may also include a mass spectrometer for obtaining the data for use in classification. The classification generation system may be instantiated as a laboratory test center operating on samples, such as blood-based samples, to make predictions as to whether the samples are associated with a patient that is likely to benefit from a drug or combination of drugs. Alternatively, the classification generation system may include a genomic or proteomic microarray assay platform (for example, gene or mRNA expression profiling chips such as those offered by Affymetrix, Inc. or the equivalent) that obtains a multitude of gene, protein, or mRNA expression profiles from a sample, e.g., tissue or other biological sample. Typically, such sample data is also associated with some clinical data and a group or class attribute, such as whether the patient providing the sample has or does not have cancer, was or was not responsive to some therapy, an early or late responder, had early or late recurrence of cancer, etc. The clinical data thus may include a class label for the sample. Once the classifier has been generated in accordance with the present inventive methods from the measurement data and class labels, a sample to be classified is obtained and measurement data for the sample is obtained and supplied to the classifier. The classifier generates a class label for the patient, e.g., responder/non-responder, cancer/non-cancer, high risk/low risk of relapse, etc.

In yet another aspect, a laboratory test center is described which includes a measurement system for conducting a physical testing process on a test sample and obtain data for classification (e.g., mass spectrometer, or gene expression assay platform), and a programmed computer implementing a final classifier as described herein, wherein the programmed computer is operative to classify the data for classification obtained from the test sample.

In another aspect, a method of classifying a biological sample is disclosed. The method includes step a) generating a classifier according to the methodology described above (obtaining classification data, constructing mini-classifiers, filtering the mini-classifiers, and combining them using a regularized combination method to generate a master classifier), step b) conducting a measurement of the biological sample to thereby obtain a set of feature values pertaining to the biological sample for use in classification of the biological sample, and step c) executing in a programmed computer an application of the classifier generated in step a) to the feature values obtained in step b) and producing a class label for the biological sample.

In still another aspect, a method for classifying a test sample is disclosed. The method includes steps of: a) subjecting the test sample to a measurement process (e.g., mass spectrometry) and responsively generating a set of values for a multitude of features (e.g., m/z peak positions); b) subjecting at least one reference sample to the same measurement process in step a) and responsively generating a reference set of feature values; c) in a programmed computer, correcting the feature values generated in step a) for the test sample from a defined feature correction function, the feature value correction function obtained from the reference set of feature values generated in step b); and d) with the programmed computer conducting a classification of the sample using a classifier and the corrected feature values.

In still another aspect, a method of classifier generation is disclosed which includes steps of: obtaining a development sample set of data in the form of multitude of feature values from a physical measurement of a set of samples (e.g., mass spectrometry data, genomic expression data etc.), the development sample set including a class label assigned to each member of the development sample set; with the aid of a computer, generating a classifier from the development sample set; evaluating the performance of the classifier; assigning a new class label for each member of a subset of the development sample set which are identified as persistently misclassified during the evaluating step; with the aid of the computer, generating a new classifier based on the development sample set including the subset with the new class labels; and evaluating the performance of the new classifier. In one embodiment, the classifier and the new classifier are based on a master classifier generated by combining a filtered set of mini-classifiers using a regularized combination method, e.g., logistic regression training and dropout regularization, performed on a training set obtained from the development set of samples. In one embodiment, the classifier and new classifier are obtained from a multitude of splits of the development sample set into training and test sets. In another embodiment, the method can further include the step of selecting a new set of feature values in the development sample set data. The generating the new classifier step is performed using the development sample set with the subset of new samples with new class labels and the new set of feature values. This methodology will be explained in more detail in the Example 4 of CMC/D classifier development using genomic data, but may be applied to other types of data sets.

A still further aspect of the invention is a method of classifier generation which includes the steps of: (a) obtaining a development sample set of data in the form of feature values from a physical measurement of a set of samples, each of the set of samples having an initial class label, wherein the initial class label has a therapeutic or diagnostic attribute; (b) dividing the development sample set of data into a training set and a test set, (c) with the aid of a computer, generating a master classifier from a filtered set of mini-classifiers combined in accordance with a regularized combination method; (d) evaluating the performance of the master classifier; (e) splitting the development sample set into a new realizations of the training and test sets; (f) repeatedly iterating steps (c), (d) and (e) on different realizations of the training set and test set and thereby generating a plurality of master classifiers, and (g) defining a final classifier from one or more of the master classifiers. This final classifier may be defined as a master classifier having typical performance, as a majority vote of all master classifiers, by modified majority vote, as a weighted average, or using some other combination method.

BRIEF DESCRIPTION OF THE DRAWINGS

FIG. 5A is a plot of the cumulative frequency of probabilities of being classified as Early in the GI-4000 arm test set generated by the first CMC/D classifier created. Samples classified as Late (Early) using the adjusted probability cutoff of 0.75 are shown. FIG. 5B consists of Kaplan-Meier plots for TTR for the test set classifications generated by the first CMC/D classifier using the adjusted probability cutoff of 0.75.

FIG. 6A is a histogram showing the distribution of hazard ratios (HR) between Early and Late classifications for the GI-4000 test set. FIG. 6B is a histogram showing the distribution of hazard ratios between Early and Late classifications for the control test set. FIGS. 6A and 6B are histograms for 60 different training/test set realizations.

FIGS. 7A and 7B are histograms showing the distribution of hazard ratios between Early and Late classifications for the GI-4000 test set (FIG. 7A) and the control test set (FIG. 7B) for 60 training/test set realizations with original class labels (top) and updated class labels (bottom).

FIGS. 10E-10I are the plots of recurrence free survival (RFS) and overall survival (OS) for patients in the GI-4000+ gemcitabine study as shown in FIGS. 10C and 10D, but plotted in pairs for ease of reference.

FIG. 11 is a detailed low chart showing a method for generating a CMC/D classifier from measurement data and initial group/class label assignments associated with the samples in a classifier development sample set.

FIG. 12 is a flow chart showing a test methodology for testing a biological sample using a CMC/D classifier generated in accordance with FIG. 11 for Example 3. In FIG. 12, there are additional steps shown on the right hand side of the figure for use in the situation where feature-dependent noise characteristics are introduced to insure stability of the classifier. These steps are not considered essential for the method.

FIGS. 14A-14F are plots of the distribution of Hazard Ratios (HR) between Early and Late classification of the test sets for PFS and OS generated in the CMC/D classifier generation method (step 1134 in FIG. 11). FIGS. 14A-14B are for PFS and OS for the initial class labels, whereas FIGS. 14B-14F are for PFS and OS after one or two flips of class labels for test samples frequently misclassified.

FIG. 16A shows OS for gefitinib-treated patients; FIG. 16B shows PFS for gefitinib-treated patients, FIG. 16C shows OS for chemotherapy-treated patients and FIG. 16D shows PFS for chemotherapy-treated patients

In FIG. 27, a reselection of features in the measurement data was performed when corrected/flipped training labels were assigned for samples which were misclassified in a previous iteration of the method, and new definitions of class labels defined.

FIGS. 32A and 32B are SAM plots showing the progression of statistical significance of features selected for classification in Example 4 from an initial set of features (FIG. 32A) to a final set of features (FIG. 32B) after three iterations of the classifier development process with label flips and selection of new features with each flip.

DETAILED DESCRIPTION

Figure 1:
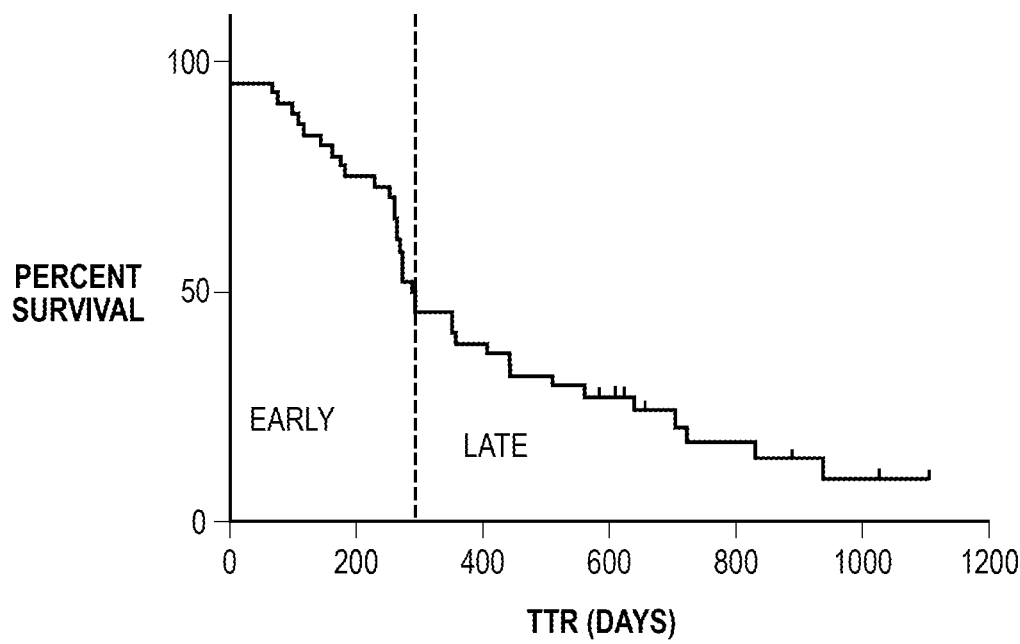
FIG. 1 is Kaplan-Meier plot of TTR (time to recurrence) for subjects in the treatment arm of the GI-4000 study showing the division of subjects into Early and Late recurrence groups.

In a first aspect, a method for classifier generation is disclosed. The classifier generated with the method is used to assign a class label to a sample under test. The classifier generation method will be described in both the context of mass spectrometry data of a set of blood-based samples, and genomic data (e.g., mRNA transcript expression levels) from tissue samples. In two illustrated examples below, the classifier is generated in order to construct a test to predict whether a patient providing a blood-based sample is likely to benefit from a particular drug or combination of drugs. A first example is described below in the context of generating a classifier for the GI-4000+gemcitabine drug combination to treat pancreatic cancer. A second example is described below in the context of generating a classifier to predict whether a NSCLC patient is likely to benefit from an EGFR-I in treatment of cancer as compared to chemotherapy. However, it will be appreciated that the methodology described herein is generally applicable to classifier development, and is not limited to these particular examples. The classifier generation method is particularly useful for mass spectrometry data of biological samples. However, the method is useful for other types of classification problems and other types of data or sample sets. For example, the classifier generation method is performed on genomic data (mRNA transcript expression levels) from set of tissue samples. This classifier is then used to predict whether a breast cancer patient is at high or low risk of early relapse.

As noted previously, in contrast to standard applications of machine learning focusing on developing classifiers when large training data sets are available, the big data challenge, in bio-life-sciences the problem setting is different. Here we have the problem that the number of available samples, arising typically from clinical studies, is often limited, and the number of attributes usually exceeds the number of samples. Rather than obtaining information from many instances, in these deep data problems one attempts to gain information from a deep description of individual instances. The present methods take advantage of this insight. While they are ideally suited to classifier development situations where the number of available samples for classifier training is limited, they are not necessarily limited to only these situations.

The method includes a first step a) of obtaining measurement data for classification from a multitude of samples, i.e., measurement data reflecting some physical property or characteristic of the samples. The data for each of the samples consists of a multitude of feature values, and a class label. For example, the data could be mass spectrometry data obtained from subjecting the sample to some form of mass spectrometry, e.g., MALDI-TOF, in the form of feature values (integrated peak intensity values at a multitude of m/Z ranges or peaks) as well as a label indicating some attribute of the sample (cancer/non-cancer, early responder/late responder. etc.). Alternatively, the multitude of feature values could be genomic data, e.g., fluorescence intensity measurements which are associated with gene expression levels, mRNA expression levels, or the like, from a particular sample, e.g., tissue or blood, and a class label. This label could have diagnostic or therapeutic attributes, and may be defined by an operator. For example, the label could be in the form of diagnostic label (cancer/non-cancer), whether the sample came from a patient that benefitted from some particular drug or combination of drugs (benefit/non-benefit), or a label indicating some other property or characteristic of the sample, such as whether the patient had an early or late recurrence of disease (early/late), had a good or poor overall survival (good/poor), etc. The class label can be assigned previously in some automated fashion, or could be assigned by a human operator prior to or at the time of generation of the classifier, and may be iteratively defined during multiple iterations of master classifiers over different splits of a development sample set into training and test sets or after evaluation of the classifier performance after an initial, tentative label is assigned, as will be appreciated from the following discussion.

The method continues with a step b) of constructing a multitude of individual mini-classifiers using sets of feature values from the samples up to a pre-selected feature set size s (s=integer 1 . . . n). For example a multiple of individual mini- or atomic classifiers could be constructed using a single feature (s=1), or a pair of features (s=2), or three of the features (s=3), or even higher order combinations containing more than 3 features. The selection of a value of s will normally be small enough to allow the code implementing the method to run in a reasonable amount of time, but could be larger in some circumstances or where longer code run-times are acceptable. The selection of a value of s also may be dictated by the number of measurement data values (p) in the data set, and where p is in the hundreds, thousands or even tens of thousands, s will typically be 1, or 2 or possibly 3, depending on the computing resources available. The mini-classifiers execute a supervised learning classification algorithm, such as k-nearest neighbors, in which the values for a feature or pairs of features of a sample instance are compared to the values of the same feature or features in a training set and the nearest neighbors (e.g., k=5) in feature space are identified and by majority vote a class label is assigned to the sample instance for each mini-classifier. In practice, there may be thousands of such mini-classifiers depending on the number of features which are used for classification.

The method continues with a filtering step c), namely testing the performance, for example the accuracy, of each of the individual mini-classifiers to correctly classify at least some of the multitude of samples, or measuring the individual mini-classifier performance by some other metric (e.g. the difference between the Hazard Ratios (HRs) obtained between groups defined by the classifications of the individual mini-classifier for the training set samples in the experimental and control arms of a clinical trial) and retaining only those mini-classifiers whose classification accuracy, predictive power, or other performance metric, exceeds a pre-defined threshold to arrive at a filtered (pruned) set of mini-classifiers. The class label resulting from the classification operation may be compared with the class label for the sample known in advance if the chosen performance metric for mini-classifier filtering is classification accuracy. However, other performance metrics may be used and evaluated using the class labels resulting from the classification operation. Only those mini-classifiers that perform reasonably well under the chosen performance metric for classification are maintained. Alternative supervised classification algorithms could be used, such as linear discriminants, decision trees, probabilistic classification methods, margin-based classifiers like support vector machines, and any other classification method that trains a classifier from a set of labeled training data.

To overcome the problem of being biased by some univariate feature selection method depending on subset bias, we take a large proportion of all possible features as candidates for mini-classifiers. We then construct all possible KNN classifiers using feature sets up to a pre-selected size (parameter s). This gives us many "mini-classifiers": e.g. if we start with 100 features for each sample (p=100), we would get 4950 "mini-classifiers" from all different possible combinations of pairs of these features (s=2), 161,700 mini-classifiers using all possible combination of three features (s=3), and so forth. Other methods of exploring the space of possible mini-classifiers and features defining them are of course possible and could be used in place of this hierarchical approach. Of course, many of these "mini-classifiers" will have poor performance, and hence in the filtering step c) we only use those "mini-classifiers" that pass predefined criteria. These criteria are chosen dependent on the particular problem: If one has a two-class classification problem, one would select only those mini-classifiers whose classification accuracy exceeds a pre-defined threshold. In the case of the GI-4000 study described herein (Example 1 below), we selected those classifiers that would be predictive to some degree, i.e. where the hazard ratio (HR) between Late and Early recurrence groups is smaller in the GI-4000+gemcitabine group (treatment arm) than in the gemcitabine group (control arm) by some pre-specified value. Even with this filtering of "mini-classifiers" we end up with many thousands of "mini-classifier" candidates with performance spanning the whole range from borderline to decent to excellent performance. (In Example 1 described below there were approximately 3,500 such mini-classifiers which passed the filtering test and were used for logistic training with drop-out).

The method continues with a step d) of generating a master classifier (MC) by combining the filtered mini-classifiers using a regularized combination method. In one possible example, this step involves repeatedly conducting a logistic training of the filtered set of mini-classifiers generated at step c) to the classification labels for the samples. This is achieved by randomly selecting a small fraction of the filtered mini-classifiers as a result of carrying out an extreme dropout from the filtered set of mini-classifiers, and conducting logistical training on such selected mini-classifiers. While similar in spirit to standard classifier combination methods (see e.g. S. Tulyakov et al, *Review of Classifier Combination Methods*, Studies in Computational Intelligence, Volume 90, 2008, pp. 361-386), we have the particular problem that some "mini-classifiers" could be artificially perfect just by random chance, and hence would dominate the combinations. To avoid this overfitting to particular dominating "mini-classifiers", we generate many logistic training steps by randomly selecting only a small fraction of the "mini-classifiers" for each of these logistic training steps. This is a regularization of the problem in the spirit of dropout as used in deep learning theory. In this case, where we have many mini-classifiers and a small training set we use extreme dropout, where in excess of 99% of filtered mini-classifiers are dropped out in each iteration.

Other methods for performing the regularized combination method in step (d) that could be used include:

Logistic regression with a penalty function like ridge regression (based on Tikhonov regularization, Tikhonov, Andrey Nikolayevich (1943). "Об устойчивости обратных задач" [On the stability of inverse problems]. Doklady Akademii Nauk SSSR 39 (5): 195-198.)

The Lasso method (Tibshirani, R. (1996). Regression shrinkage and selection via the lasso. J. Royal. Statist. Soc B., Vol. 58, No. 1, pages 267-288).

Neural networks regularized by drop-out (Nitish Shrivastava, "Improving Neural Networks with Dropout", Master's Thesis, Graduate Department of Computer Science, University of Toronto; available at http://www.cs.toronto.edu/~nitish/msc_thesis.pdf.

General regularized neural networks (Girosi F. et al, Neural computation, (7), 219 (1995).

The above-cited publications are incorporated by reference herein.

In step e) of the method, the samples are a set of samples which are randomly separated into a test set and a training set, and the steps b)-d) are repeated in the programmed computer for different realizations of the separation of the set of samples into test and training sets, thereby generating a plurality of master classifiers, one for each realization of the separation of the set of samples into training and test sets.

The method continues with step f) of defining a final classifier from one or a combination of more than one of the plurality of master classifiers. The final classifier can be defined in a variety of ways, including by selection of a single master classifier from the plurality of master classifiers having typical or representative performance, by majority vote of all the master classifiers, by modified majority vote (explained below), by weighted majority vote, or otherwise.

Our approach of generating a master classifier is similar in spirit to "drop-out" regularization, a method used in the deep learning community to add noise to neural network training to avoid being trapped in local minima of the objective function. See Nitish Shrivastava, "*Improving Neural Networks with Dropout*", Master's Thesis, Graduate Department of Computer Science, University of Toronto; available at http://www.cs.toronto.edu/~nitish/msc_thesis.pdf. Our method can also be viewed from an ensemble learning approach (see e.g. "Ensemble Methods", Zhi-Hua Zhou, CRC Press, 2012 Boca Raton). Such approaches have shown promise in avoiding over-fitting, and increasing the likelihood of generating generalizable tests, i.e. tests that can be validated in independent sample sets.

The method recited above has many practical advantages and uses. Often, in classification development, particularly in the health sciences are such as cancer research or drug development, the researcher is faced with the problem of having only a small sample set available, which results in very small training and test sets if one were to follow a standard approach to classifier development. For example, in a sample set for a drug efficacy study, a training set could consist of perhaps 20 samples (n=20) from the treatment arm and a training set of similar size if one also splits the control arm into training and test sets. This would result in only about 10 samples in the early and late recurrence groups (see below), defined by some training label assignment, such as Early or Late. Standard approaches would start by investigating features (e.g., peaks in mass spectrometry data) and select those features that show some promise of containing information relevant to the training classes. These would then be combined using a k-nearest neighbor method to generate a multivariate test. For small sample sizes, as in this example, the selection of features included in the construction of a multivariate test can easily be dominated by some features that show discriminating power primarily due to a particular split of the samples into training and test sets. In other words, using univariate p-values to select features becomes less informative for smaller sample sizes, as the p-values themselves become less informative. One could attempt to overcome this issue by trying out many training/test set split scenarios, but there does not seem to be a practical way to avoid picking specialized features for each of these scenarios, which makes an estimation of the generalization performance of developed tests difficult. In previous work (the '909 application recited above incorporated by reference) we developed sophisticated cross-validation techniques, which showed substantial promise that this sample set allows for the development of a predictive test. However, this work resulted in many classifier candidates, and the selection of a particular classifier for further validation remained difficult.

We developed the methodology described herein that addresses both issues: (a) it does not depend on a particular selection of features for inclusion in a multivariate test, and (b) by combining many, even thousands, of possible classifier candidates, it provides a means of automatically generating one single well performing classifier (test).

We coined the term "combination of mini-classifiers with dropout", or "CMC/D" for short, to refer to the classifier generation method described in this document. The application of CMC/D to the GI-4000 data set, as explained below in Example 1, provides some major advantages over previous work: CMC/D enables us to work with smaller training sets and so allows a splitting of a sample set into a training set and a test set. This alleviates the major concern with previous work, i.e. the lack of an independent test set. CMC/D also allows the investigation of the dependence of classifier performance on a particular test/training split, which could lead to bias for small sample sets. Lastly, CMC/D results in one master classifier/test for each training/test set split. While this test may not be the most optimal that could be constructed given the data, such a test will be, by construction, less prone to the dangers of overfitting due to some artifact in the training set data.

The classifiers generated by CMC/D are probabilistic in nature as a result of using a regularized combination method, such as logistic regression in the combination of "mini-classifiers" in step d) of the method. The result of applying a CMC/D classifier to a particular sample measurement data (e.g., mass spectrum) gives the probability of a particular class (group) label, in this case Early, given the sample data, ranging from 0 to 1, with a probability of 0 indicating one class label and a probability of 1 indicating another class label. In Example 1, we used the natural probabilistic cut-off of 0.5 for classifying a sample as Early; i.e. if the probability generated for a particular sample is greater than 0.5 we classify it as Early, and conversely, if the probability is less 0.5 we classify the sample as Late. Values other than 0.5 could be used depending on design considerations. While we give an example of the effect of varying this cut-off below in Example 1, we chose the cut-off value of 0.5 for all development steps and for the final classification. This cut-off value is an adjustable parameter in the method, as will be explained below.

The type of samples which are used in classifier generation according to the inventive method is not particularly important and can vary widely. In one specific example, the samples are biological samples obtained from a human (such as blood, cerebrospinal fluid, urine etc.) and the step of obtaining data comprises performing some physical measurement on the sample, such as mass spectrometry and storing associated mass-spectral data. Another example of the physical measurement process is performing a genomic assay to obtain gene, protein, mRNA transcript, etc. expression levels (e.g., from fluorescence measurements) and storing the associated genomic data. In one specific example, the biological samples comprise tissue or blood-based samples from a human with cancer. The samples may be unfractionated serum or plasma samples, or could be samples after some depletion or fractionation step has been performed.

In one further embodiment, as described below in Example 1, the mass spectrometry data is acquired from at least 20,000 shots in MALDI-TOF mass spectrometry, such as for example using the "Deep-MALDI" mass spectrometry method described in US patent application of H. Röder et al., Ser. No. 13/836,436 filed Mar. 15, 2013, the content of which is incorporated by reference herein, and Duncan, et al., *Extending the Information Content of the MALDI Analysis of Biological Fluids (Deep MALDI)* presented at 61st ASMS Conference on Mass Spectrometry and Allied Topics, Minneapolis, USA June 2013.

It will further be appreciated the method will typically be implemented in a tangible, practical computing environment in which the measurement data for a set of samples is obtained by some measuring instrument, such as mass spectrometer or genomic assay, and the classifier generation steps b)-f) are implemented in a microprocessor of a programmed general-purpose computer. The generation of computer-executable code implementing the classifier development methodology from the present description, flow charts, and detailed examples, is within the ability of persons skilled in the art.

Example 1

Generation of CMC/D Classifier from Mass-Spectrometry

Data Obtained from Human Samples

FIGS. 1-11

This section of this document will explain a practical example of the execution of the CMC/D classifier development method in the context of a sample set in the form of blood-based samples which are subject to mass spectrometry and resulted in a data set for use in classification in the form of 100 features (peaks) at different m/Z positions which were used as the set of features from which to select features for mini-classifiers. The samples were obtained from pancreatic cancer patients enrolled in a clinical trial of the drug GI-4000. The goal of the classifier generation exercise was to demonstrate whether a classifier (test) operating on a mass spectrum of a blood-based sample could be constructed which accurately predicts, in advance of treatment, whether the pancreatic cancer patient associated with the sample is likely to benefit from GI-4000 in combination with gemcitabine as compared to gemcitabine alone. The methodology described in this example will apply by analogy to other sample sets or classification problems.

Patient Population and Available Samples

Samples used for this project were pre-treatment samples collected during the trial of GI-4000+gemcitabine versus gemcitabine alone as adjuvant therapy for resectable pancreas cancer in patients with tumors harboring KRAS mutations. Samples were depleted plasma, left after performance of ELISpot assays. Baseline samples were only available from 91 of the 179 patients enrolled in the trial. One sample initially classified as baseline may have been taken early in treatment and this (sample ID 520) was excluded from this study. The 90 remaining samples (listed in Example 1 Appendix A) were used to generate the deep MALDI mass spectra used in this project.

Table 1 summarizes the patient characteristics for the 90 subjects providing samples for this project. Forty four subjects were randomized to the treatment arm and 46 to the control arm. Demographics and baseline characteristics were well balanced between the GI-4000 and control arms within the data set. The data set appears to be generally representative of the overall study with two possibly meaningful imbalances, one favoring the patient group we did not use ("non-BDX group") and one favoring the patient group we did use ("BDX group") in terms of predicted outcome. Resection status, age and gender were well balanced between these two groups. There was an imbalance in ECOG performance status between the two groups with 92.3% of the BDX group having a performance status of 0 or 1 compared with 76.8% in the non-BDX group. However in the non-BDX group 14% were not reported vs. 0% in the BDX group. This imbalance is therefore probably not meaningful as most subjects in both groups had PS 0-1. The unreported group would most likely have been PS 0-1 if reported.

There was an imbalance in lymph node involvement with 72.2% in the BDX group having more than one node involved vs. 46.5% in the non-BDX group and 15.6% having no positive nodes in the BDX group vs. 34.9% in the non-BDX group so from a nodal status perspective, the BDX group had more extensive disease at baseline than the overall study population.

TABLE 1

Patient characteristics for subjects in this analysis

| Patient Characteristics | GI-4000 (N = 44) | Control (N = 46) |
|---|---|---|
| Age, Median (Range) | 66.5 (36-80) | 60 (46-82) |
| Gender, n (%) | | |
| Female | 15 (34) | 21 (46) |
| Male | 29 (66) | 25 (54) |
| Resection Status, n (%) | | |
| R0 | 34 (77) | 37 (80) |
| R1 | 10 (23) | 9 (20) |
| *ECOG Performance Status, n (%) | | |
| 0 | 12 (27) | 12 (26) |
| 1 | 29 (66) | 29 (63) |
| 2 | 3 (7) | 3 (7) |
| ELISpot Responder | | |
| Yes | 11 (25) | 13 (28) |
| No | 24 (55) | 21 (46) |
| NA | 9 (20) | 12 (26) |

*In control, 1 patient did not have ECOG performance status and 1 patient was PS 3

Spectral Acquisition and Pre-Processing
Generation of Deep MALDI Spectra

Spectra were generated using the deep MALDI method (see U.S. patent application Ser. No. 13/836,436 filed Mar. 15, 2013, the contents of which are incorporated by reference herein) using 10 matrix spots, 250 locations on a matrix spot with 800 laser shots per location, resulting in a theoretical maximum of 2,000,000 laser shots per sample. Following filtering out of unusable location spectra using acquisition testing, we were left with a minimal size of 875,000 shots for some samples and more for the others. We exceeded the design goal of at least 500,000 shot spectra. We chose 625 location spectra at random from those location spectra that passed acquisition testing to generate deep MALDI spectra comprising an average of 500,000 laser shots.

These deep MALDI spectra were pre-processed to generate comparable spectra using the following steps:

Background Estimation and Subtraction

The background was estimated using a two-step process. Initially wide estimation windows were chosen to account for large scale (in m/Z) trends in the background. Deep MALDI often gives small peaks in the m/Z-neighborhood of large peaks leading to inaccurate background estimation for these small peaks by following the large peaks too closely. To avoid this effect we added a supplementary background component to the previously estimated background using smaller estimation windows. The resulting two-step background was subtracted from all spectra.

Spectral Alignment

In any mass spectra there are slight discrepancies with respect to the translation of time-of-flight numbers to m/Z values. We identified a set of peaks that are present in the vast majority of the mass spectra and rescaled each spectrum's m/Z values such that the sum of the squared deviations of the common peaks in each individual spectrum to the reference set is as small as possible. This process leads to better resolution of close (in m/Z) features.

Normalization

In order to obtain features that differentiate between clinical groups, we need to measure the intensity of peaks from different samples and compare their values. The overall amount of ionized protein is not controllable within the MALDI process, and so we can only measure relative peak intensities. To do this we need to normalize the spectra. In order to avoid propagating the variability of peak intensities from peaks that are either intrinsically variable or which correlate to the clinical status of the patient to stable peaks during normalization, we used the spectral intensity from three regions in m/Z showing little sample dependence to normalize the spectra.

Feature Definitions and Feature Tables

In order to define possible candidates for peaks that can differentiate between clinical groups we located peaks in the pre-processed spectra and defined a range in m/Z around each peak's maximum. These ranges in m/Z define features that are used for all further analysis. We selected 655 features as possible candidates for differentiating between groups and calculated the integrated intensity of each of these features for each spectrum. In this way we obtain a feature value for each feature for each spectrum. The tabular listing, rows are spectra, columns are features, of these integrated intensities (feature values) is the feature table.

In the next section we will show how to use a newly designed methodology to utilize the feature table to construct a predictive test for selecting patients who benefit from the addition of GI-4000 to gemcitabine.

CMC/D Classifier Development Methodology Overview

In this example we were faced with the problem of having only a small sample set available, which results in very small training and test sets if one were to follow a standard approach. As explained above, for small sample sizes, as in this study, the selection of features included in the construction of a multivariate test can easily be dominated by some features that show discriminating power primarily due to a particular training/test split. One could attempt to overcome this issue by trying out many training/test set split scenarios, but there does not seem to be a practical way to avoid picking specialized features for each of these scenarios, which makes an estimation of the generalization performance of developed tests difficult. In previous work we developed sophisticated cross-validation techniques, which showed substantial promise that this sample set allows for the development of a predictive test. However, this work resulted in many classifier candidates, and the selection of a particular classifier for further validation remained difficult.

The CMC/D classifier development methodology described here addresses both issues: it does not depend on a particular selection of features for inclusion in a multivariate test, and by combining many, even thousands, of possible classifier candidates; it provides a means of automatically generating one single well-performing test.

To overcome the problem of being biased by some univariate feature selection method depending on subset bias, we take a large proportion of the feature values in the mass spectrometry data as candidates for classification. We then construct all possible kNN classifiers (i.e., the "mini-classifiers" herein) using feature sets up to a pre-selected size (s, =1, 2, or some other integer). This gives us many classifiers: e.g. if we start with 100 features, we would get 4950 "mini-classifiers" from all different pairs of these features (s=2), 161,700 for the combination of three features (s=3), and so forth. Of course, many of these "mini-classifiers" will have poor performance, and we only use those "mini-classifiers" that pass predefined filter criteria based on classification accuracy. These criteria are chosen dependent on the particular problem: If one has a two-class classification problem, one would select only those mini-classifiers whose classification accuracy exceeds a pre-defined threshold. In the case of the GI-4000 study, in the filtering step of the method we selected those classifiers that would be predictive to some degree, i.e. where the hazard ratio (HR) between late and early groups is smaller in the GI-4000+ gemcitabine group than in the gemcitabine group by some minimal amount. Even with this filtering of "mini-classifiers" we end up with many thousands of "mini-classifier" candidates spanning the whole range from borderline to decent to excellent performance.

In our method we generate a "master classifier" by combining these "pre-filtered mini-classifiers" using logistic training to the group (class) labels. While similar in spirit to standard classifier combination methods, we have the particular problem that some "mini-classifiers" could be artificially perfect just by random chance, and hence would dominate the combinations. To avoid this overfitting to particular dominating "mini-classifiers", we generate many logistic training steps by randomly selecting only a small fraction of the "mini-classifiers" for each of these logistic training steps. The final master classifier then uses the average over all the logistic regression steps.

In more detail, the result of each mini-classifier is one of two values, either "Early" or "Late". We can then use logistic regression to combine the results of the mini-classifiers in the spirit of a logistic regression by defining the probability of obtaining an "Early" via standard logistic regression (see e.g. http://en.wikipedia.org/wiki/Logistic_regression)

$$P(\text{"early"} | \text{feature for a spectrum}) = \frac{\exp\left(\sum_{\text{Mini classifiers}} w_{mc} I(mc(\text{feature values}))\right)}{\text{Normalization}} \quad \text{Eq.(1)}$$

where I(mc(feature values))=1, if the mini-classifier mc applied to the feature values of a sample returns "Early", and −1 if the mini-classifier returns "Late". The weights $w_{mc}$ are unknown and need to be determined from a regression fit of the above formula for all samples in the training set using +1 for the left hand side of the formula for the Early-labeled samples in the training set, and −1 for the Late-labeled samples, respectively. As we have many more mini-classifiers, and therefore weights, than samples, typically thousands of mini-classifiers and only tens of samples, such a fit will always lead to nearly perfect classification, and can easily be dominated by a mini-classifier that, possibly by random chance, fits the particular problem very well. We do not want our final test to be dominated by a single special mini-classifier which only performs well on this particular set and is unable to generalize well. Hence we designed a method to regularize such behavior: Instead of one overall regression to fit all the weights for all mini-classifiers to the training data at the same, we use only a few of the mini-classifiers for a regression, but repeat this process many times in generating the master classifier. For example we randomly pick three of the mini-classifiers, perform a regression for their three weights, pick another set of three mini-classifiers, and determine their weights, and repeat this process many times, generating many random picks, i.e. realizations of three mini-classifiers. The final weights defining the CMC/D master classifier are then the averages of the weights over all such realizations. The number of realizations should be large enough that each mini-classifier is very likely to be picked at least once during the entire process. This approach is similar in spirit to "drop-out" regularization, a method used in the deep learning community to add noise to neural network training to avoid being trapped in local minima of the objective function.

We coined the term "combination of mini-classifiers with dropout", CMC/D, to refer to this methodology. The application of CMC/D to the GI-4000 data set provides some major advantages over previous work: CMC/D enables us to work with smaller training sets and so allows a splitting into a training set and a test set. This alleviates the major concern with previous work, i.e. the lack of an independent test set. CMC/D also allows the investigation of the dependence of classifier performance on a particular test/training split, which could lead to bias for small sample sets. Lastly, once the parameters of the CMC/D procedure are fixed, it results in one unique test without further human intervention, i.e. it eliminates the necessity of choosing one classifier from a multitude of options based on classifier performance evaluation and subjective judgment. While this test may not be the most optimal that could be constructed given the data, such a test will be, by construction, less prone to the dangers of overfitting to some artifact in the training set data.

The classifiers generated by CMC/D are probabilistic in nature as a result of using a logistic regression in the combination of "mini-classifiers". The result of applying a CMC/D classifier to a particular spectrum gives the probability of a particular class (group) label, in this case Early, given the sample data. In most of the following we used the natural probabilistic cut-off of 0.5 for classifying a sample as Early; i.e. if the probability generated for a particular sample is greater than 0.5 we classify it as Early, and conversely, if the probability is less 0.5 we classify the sample as Late. Values other than 0.5 could be used depending on design considerations, as explained below. While we give an example of the effect of varying this cut-off below, we chose the cut-off value of 0.5 for all development steps and for the final classification.

The specific methodology of generating the classifier described above is shown in flowchart form in FIG. 11 and described subsequently in Example 2.

Obtaining Measurement Data and Selection of Large Set of Features for Creation of Mini-Classifiers Deep MALDI methods produced mass spectra with 655 individual features for each sample. Each sample was assigned a class label based on time to recurrence. Taking the definition of Early and Late recurrence used in previous projects for the treatment arm (Early=recurrence event before 276 days, Late=no recurrence before 500 Days), these 655 individual features were ranked by p-value for difference between these groups. Starting with the feature with smallest p-value for comparison between Late and Early groups, each feature was inspected for quality (presence of a distinguishable peak, smoothness, lack of excessive noise). Features deemed to be of insufficient quality were rejected until 100 features had been accepted. The centers (in m/Z) of the 100 features used in CMC/D classifier generation are listed in Example 1 Appendix B.

Selection of Early/Late Recurrence Groups and Training and Test Sets

Previous classifier development efforts had divided the GI-4000 treatment arm samples into Early (recurrence prior to 275 days), Late (no recurrence before 500 days) and Intermediate groups (the remainder). As this project aimed to split the samples into test and training groups, a different separation into Early and Late groups was required to maximize the test/training group sizes for Early and Late groups. The Early group was taken to be all samples from subjects with recurrence at or prior to 290 days. This gave an Early group of 22 patients. Two samples were reserved as an Intermediate group for technical reasons to avoid time-consuming software modifications to the grouping structures of our existing software. The remaining 20 samples, from subjects with no recurrence before 350 days, were used as the Late group. The sample IDs for subjects in each of these groups are listed in Example 1 Appendix C. This division into outcome groups is illustrated on the Kaplan-Meier plot of time-to-recurrence (TTR) for the treatment arm samples in FIG. 1 of the appended figures.

Figure 2:
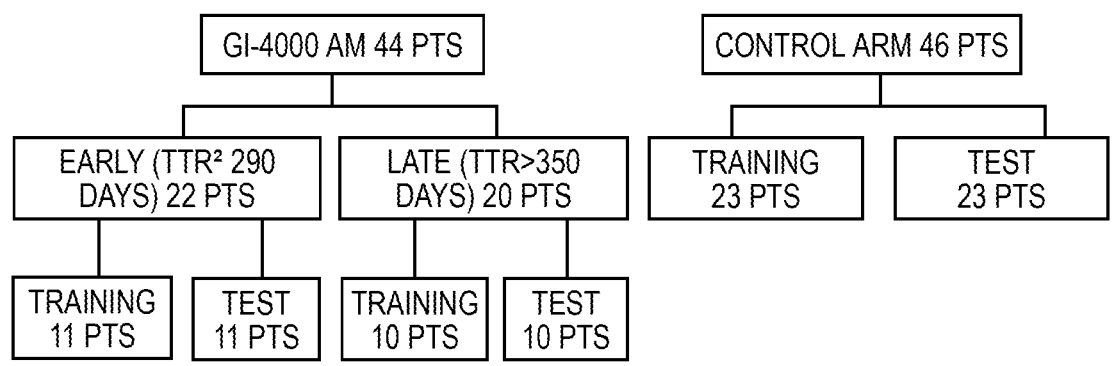
FIG. 2 is a diagram showing the split of subjects into classes (Early and Late recurrence groups) and training and test sets.

To split these treatment arm Early and Late groups into test and training sets, while maintaining a balance in outcomes across them, the following procedure was used: Each group, Early and Late, was sorted by time-to-recurrence and then split into pairs, so that the two subjects with shortest TTR formed the first pair, the next two subjects with 3rd and 4th ranked TTR formed the second pair, and so on. Within each of these pairs one subject was randomly assigned to the training set and the other to the test set. This gave equally sized training and test sets for each group (each of 11 subjects for the Early group and 10 for the Late group) with a balance of outcomes across the test/training split, while still allowing the generation of many different training/test splits in an automated, consistent manner, see FIG. 2.

Samples in the control arm were also split into training and test sets. As spectra from control arm samples are only used indirectly in classifier training, as will be explained later, only one training/test split was used for these samples. Subjects from the control arm were ranked according to their TTR and then alternately assigned to control training or control test sets to give two groups of 23 subjects each. The sample IDs for the control arm samples split into training and test sets are listed in Example 1 Appendix D.

Selection and Filtering of "Mini-Classifiers"

For a given training set it is possible to create many individual K nearest neighbor (KNN) classifiers using subsets of the 100 selected features. These individual KNN classifiers, defined by the samples in the training set and the particular subset of features define a "mini-classifier". For this project the value of K in the K-nearest neighbor algorithm was fixed at 5 throughout. As the aim is to produce a classifier with predictive power between GI-4000 and the control treatment, it was required that the "mini-classifiers" selected demonstrated some minimal level of predictive power, and so a filtering was done on the mini-classifiers to result in a filtered set of min-classifiers. The "mini-classifier" selection/filtering process was carried out as follows:

1. All 100 "mini-classifiers" formed from the training set using just one of the 100 candidate features for classification in K-NN (see Example 1 Appendix B) were selected.

2. From the 4950 possible "mini-classifiers" formed from the training set using two of the 100 candidate features for classification using K-NN (s=2), a filtering step was conducted whereby only those mini-classifiers were selected which demonstrated a minimal level of predictive power between treatment arms. The GI-4000 arm (Early training, Late training, and Intermediate) training set and control training set were classified by each 2 feature "mini-classifier". The hazard ratios (HRs) between Late and Early classifications were calculated within the GI-4000 arm and control arm training sets. If the Mantel-Haenszel HR for the control arm between Late and Early was bigger than the Mantel-Haenszel HR for the GI-4000 arm by at least 0.3 and not by more than 7.0, the "mini-classifier" was deemed acceptable for inclusion. This allowed us to exclude exceptionally over-fitted "mini-classifiers" with outrageously good performance, as well as mini-classifiers with very little or negative predictive power.

Typically, around 3,500 mini-classifiers were selected with single or pairs of candidate features. However, the number depended on the exact training set/test set realization and was sometimes less than 3000 or over 4000 for individual realizations.

Creation of Master CMC/D Classifier Using Logistic Regression with Drop Out

The several thousand "mini-classifiers" were combined into one master CMC/D classifier by training a logistic regression using the Late and Early training set labels and extreme drop out. The rate of drop out was set at 99.9%, so that of the typical 3500 or so "mini-classifiers", each drop out iteration included only 3-4 "mini-classifiers" chosen at random. Each CMC/D master classifier used 10,000 drop out iterations, which is sufficient to ensure that all mini-classifiers are likely to be included with non-zero weight in the resulting CMC/D master classifier. Hence, in general, all mini-classifiers passing the filtering procedure and all features contribute to the CMC/D master classifier. The resulting master classifier was generated as an average over all the logistic regression training of those sets of selected filtered mini-classifiers not subject to dropout. Thus, all of the 100 features listed in Example 1 Appendix B were used for classification in the master classifier. All mini-classifiers with a single feature (s=1) were used in the final classifier, and all pairs of features (s=2) were used which passed the filtering criteria (the mini-classifier using such feature pair had a degree of predictive power for the addition of GI-4000 to gemcitabine within the specified limits). This master classifier thus consisted of approximately 3,500 mini-classifiers, i.e., the combination of the 100 single feature classifiers and the two-feature classifiers that passed filtering, but with varying weights assigned to each mini-classifier.

CMC/D Classifier Performance Assessment

Once a CMC/D master classifier was created for a given training set realization, it was evaluated by running the classifier on the GI-4000 arm test set and the control arm test set. (see FIG. 2). The performance was assessed by examining the following quantities:

1. HR between Early and Late classifications of the GI-4000 test set for TTR.

2. HR between Early and Late classifications of the control arm test set for TTR.

3. HR between GI-4000 test set and control arm test set for samples classified as Late for TTR.

4. Ratio of HRs calculated in 1 and 2—similar to an interaction HR between treatment regimens and Early/Late classification.

5. Difference in HRs calculated in 1 and 2—an alternative way to assess predictive power of the classifier.

6. Median TTR for Early and Late classifications of GI-4000 test set and control arm test set.

7. Difference in median TTR for Late classifications of GI-4000 test set and control arm test set—to assess GI-4000 benefit over the control in the Late group (similar to the HR in 3).

Results

Figure 3:
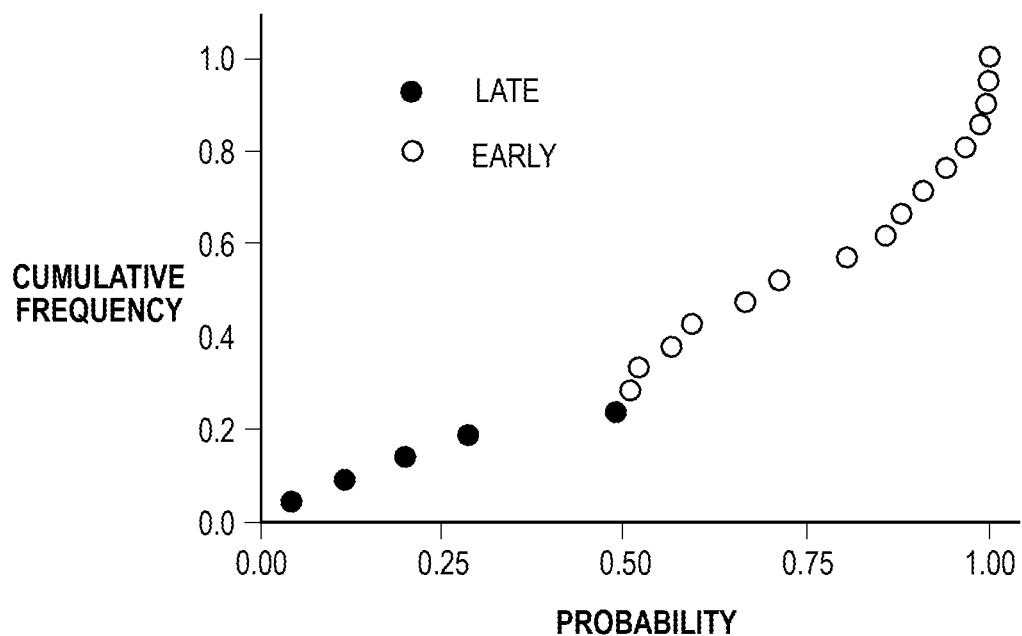
FIG. 3 shows the cumulative frequency of probabilities of being classified as Early in the GI-4000 test set generated by the first CMC/D classifier created. Samples were classified as Early or Late using the standard probability cutoff of 0.5.

The first CMC/D classifier we created classified the GI-4000 arm test set as shown in FIG. 3. FIG. 3 shows the cumulative frequency of probabilities of being classified as Early in the GI-4000 test set generated by the first CMC/D classifier created. Samples classified as Early (Late) was made using the standard cutoff of 0.5 and are shown in in the Figure, see legend.

Five of the 21 test set samples were classified as Late, using the standard 0.5 probability cutoff.

Figure 4:
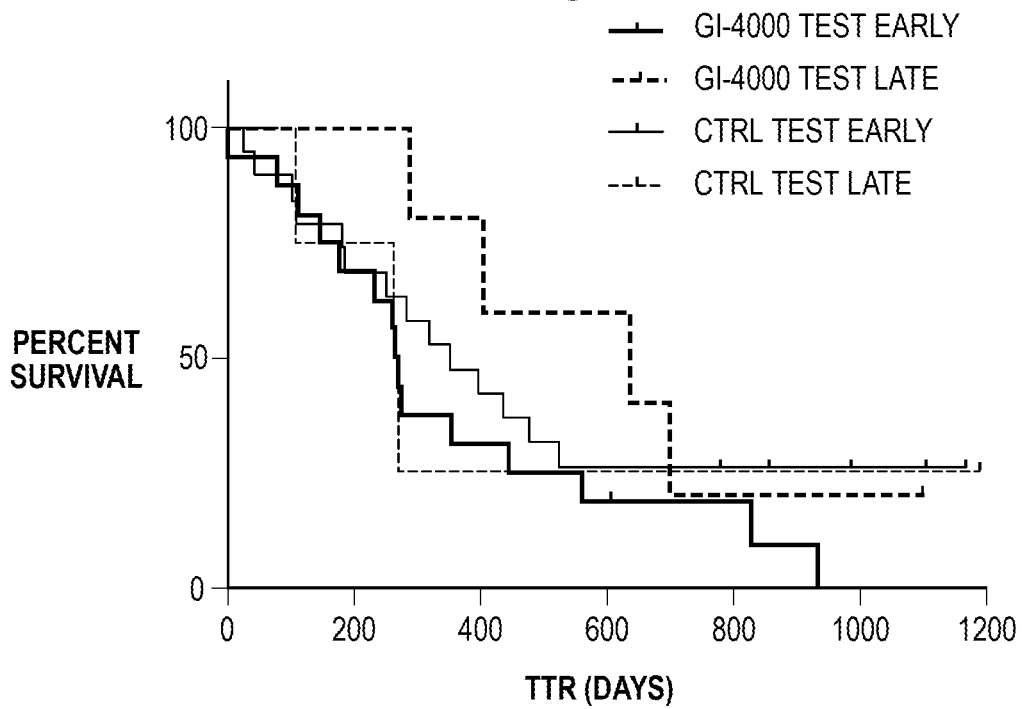
FIG. 4 shows Kaplan-Meier plots for TTR for the test set classifications generated by the first CMC/D classifier.

The Kaplan-Meier plot for TTR for the classifications in FIG. 3 and the classifications of the control test set are shown in FIG. 4.

The use of logistic regression to combine the "mini-classifiers" into a CMC/D master classifier gives one adjustable parameter, namely the cutoff in probability of being Early, which separates the Early and Late classifications. Adjusting this cutoff from the default value of 0.5 allows one to 'tune' the ratio of Early:Late classifications. As an example of how this can be Used, the cutoff was adjusted from 0.5 to 0.75 for this first CMC/D classifier. This increased the percentage of Late classifications in the GI-4000 test set to 52%. The results are shown in FIG. 5. In particular, FIG. 5A shows a plot of the cumulative frequency of probabilities of being classified as Early in the GI-4000 arm test set generated by the first CMC/D classifier created. Samples classified as Late (Early) using the standard cutoff of 0.75 are shown in contrasting dots. In FIG. 5B, Kaplan-Meier plots for TTR for the test set classifications generated by the first master classifier using the adjusted probability cutoff of 0.75 are shown.

The combination of many "mini-classifiers" using a large set of candidate features (p>>n) alleviates the problems of small training sets as far as overfitting of the feature selection problem is concerned. However, it does not remove the issue of sample bias in the split into training and test sets. This is of particular importance to this specific problem, because we do not have a natural or gold-standard choice for our classification groups, i.e., "Early" and "Late" recurrence groups. In contrast to the kind of classification problems that classify patients into, for example, those with or without cancer, where the groups can be determined by an independent, definitive measurement, in this case one has to try to infer groups based on continuous outcomes (specifically, time to recurrence (TTR) in this example). As many patient characteristics contribute to such outcomes one should expect that even if one knew an accurate prognostic or predictive classification, that group's outcomes would have a distribution of values with some 'good' prognosis patients having poor outcomes and some 'poor' prognosis patients having good outcomes. Overall the 'good' prognosis patients will have better outcomes than the 'poor' prognosis patients, but grouping the patients by a cutoff point in outcome will produce two groups that are correlated with the desired prognostic classifications, but not identical with them; there will be errors in the outcome-inferred groupings. Considering a training/test split realization with this in mind, one can see that if the realization has many label errors in the training set, any classifier will tend to have poor performance due to training label errors. Similarly, if the test set realization contains many label errors, a classifier that really performs well could be assessed as performing badly. Hence, it is important to try to assess the impact of the training/test realization (i.e., the split of samples into training and test sets) on the performance of the CMC/D classifiers and avoid those where an exceptional performance might result from a particularly biased choice.

For this reason, master classifiers were created for many possible training/test set realizations (splitting of the sample sets into training and test sets) generated using the general procedure above. Each realization gives particular values of the quantities used for classifier evaluation (the seven criteria specified in the performance assessment section above) and if many realizations are used to generate CMC/D master classifiers, the distributions of these quantities can be studied. Additionally, one might want to evaluate other quantities, such as the ratio of Early to Late classifications.

FIG. 6 shows histograms of the hazard ratios between Early and Late classifications for the GI-4000 test set and the control test set for around 60 different training/test set realizations/splits. The hazard ratios depend on the precise training/test set split. It is apparent that the distributions are somewhat broad, and that while many realizations produce 'typical' HRs (around 2-2.5 for GI-4000 and around 0.5-1.5 for the control), certain realizations yield outlying values. 'Typical' training/test set splits produce similar values of the hazard ratios between Early and Late classifications, but there are also less common, 'atypical' training/test set split realizations that yield much smaller or much larger hazard ratios (e.g. >5 for the GI-4000+gemcitabine arm or >3 for the control arm). These could be associated with particular training/test set splits that are particularly susceptible to overfitting or for which there is a large sample bias that yields an uncharacteristically good or poor classifier or an unrepresentative test set.

To address the issue of wrong assignment of subjects into Late and Early groups, the test set classifications of subjects in the GI-4000+gemcitabine arm were studied across the training/test set realizations. Several samples were notable as persistently classifying very badly, with 4 samples never classifying into their assigned group in any of the realizations. These sample IDs are listed in Table 2.

TABLE 2

Sample IDs and group labels for samples persistently misclassifying over many training/test set realizations

| Sample ID | Assigned Label | TTR (days) |
|---|---|---|
| 60 | Late | 353 |
| 71* | Early | 263 |
| 125 | Early | 290 |
| 126 | Early | 185 |
| 132* | Late | 354 |
| 502 | Late | 358 |
| 508* | Early | 275 |
| 513 | Late | 445 |
| 528* | Late | 585‡ |

*samples never classifying correctly;
‡censored in original data - now updated to event at 1034 days Assuming that these observations could be indicative of incorrectly assigned group (class) labels, the original Early/Late assignments for these samples were reversed for these 9 patients and the whole CMC/D classifier creation process was repeated using the updated set of labels. The resulting groupings of samples are summarized in Example 1 Appendix E.

The distributions of HRs between Early and Late classifications for GI-4000 and control test sets across training/test set realizations are shown in FIG. 7 for the original group labels as well as the updated labels. The distribution of HRs between Early and Late for the GI-4000 test set does not change very much. Meanwhile, the distribution of HRs between Early and Late for the control test set becomes narrower and its center moves to the left, indicating less separation between Early and Late groups in the control arm test set. This combination should denote an improvement in predictive power for the classifiers.

It will be noted that the assigned labels to the samples of Table 2 are those we gave initially, based on the TTR. However, when we use the master classifier to classify these samples when they are part of the test set, they persistently get classified into the opposite group. From TTR one wants these samples to have the assigned labels, but they just don't seem to fit. We have taken this as an indication that the class labels are incorrect, even though the TTR seemed to fit the class label. This is probably a result of how we split into groups in the first place. In other tests (such as the VeriStrat test described in our '905 patent cited above), some patients classified as Good die early, well before most of the Goods, and some patients classified as Poor live much longer than many other patients classified as Poor, even when Goods do better than Poors overall and as there are many factors that can affect outcome, this is not surprising. We believe that the same happens here. The classifier performance would be better if it provided better separation in the K-M survival plots and better HRs, if all the Poors (Earlys) died or recurred before all the Goods (Lates) but this is unlikely to ever happen in reality as many factors influence outcome, not just what we can measure in serum.

Figure 8A:
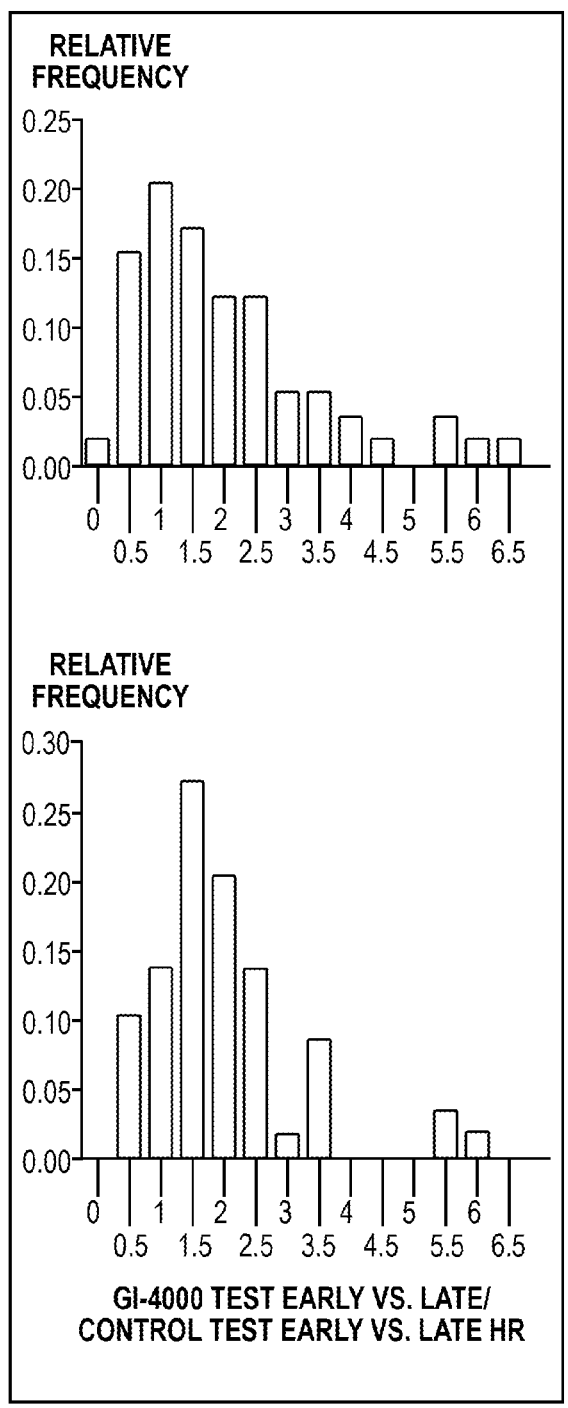
FIGS. 8A and 8B are histograms showing the distributions of (FIG. 8A) the ratio of hazard ratios between Early and Late classifications for the GI-4000 test set relative to the control test set and (FIG. 8B) the difference in median TTR between the Late group for the GI-4000 test set and the control test set for 60 training/test set realizations with original class labels (top) and updated class labels (bottom).
Figure 8B:
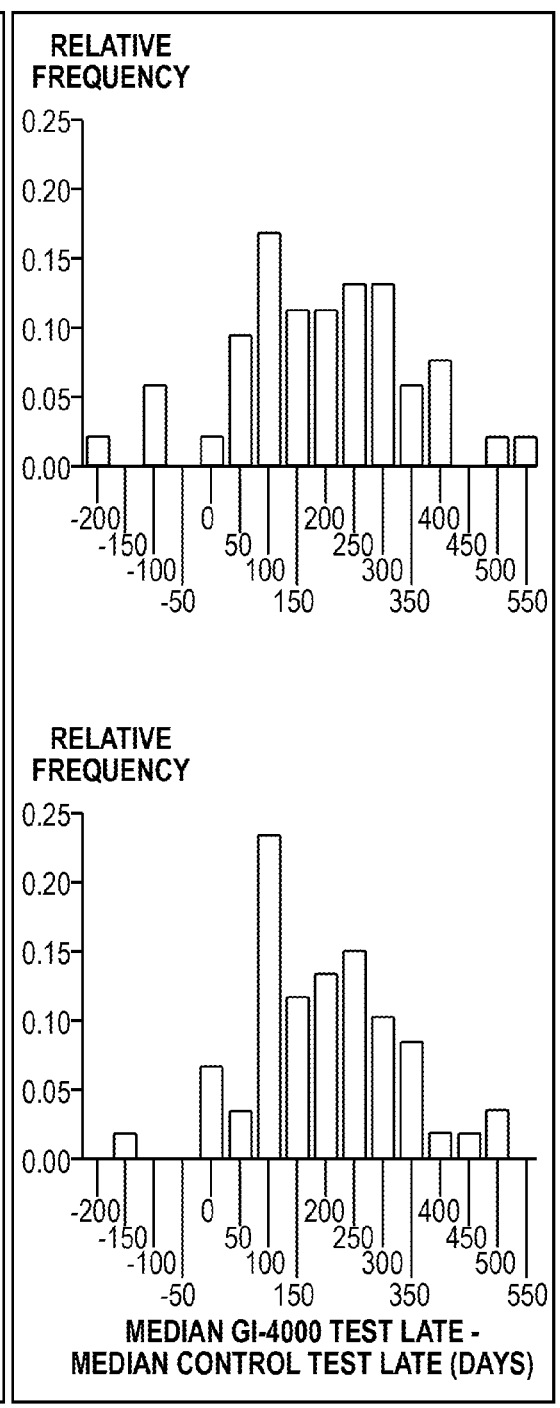
Figure 9A:
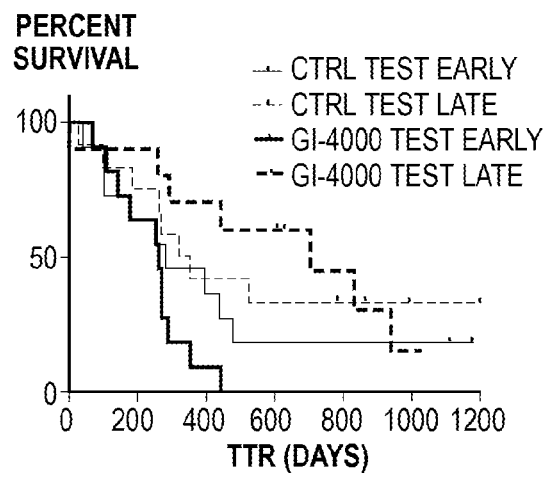
FIGS. 9A-D show Kaplan-Meier plots for four candidate CMC/D classifiers with their associated performance measures. Each of the four classifiers resulted from different splits of the available samples into training and test sets during classifier generation.
Figure 9B:
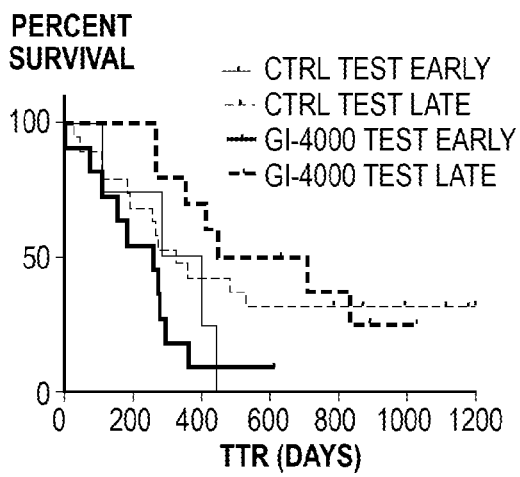
Figure 9C:
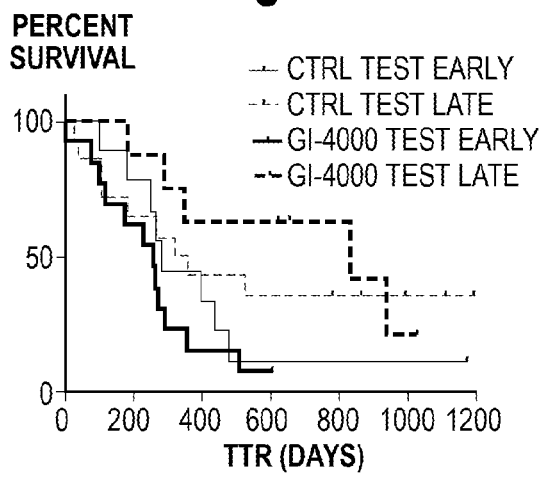
Figure 9D:
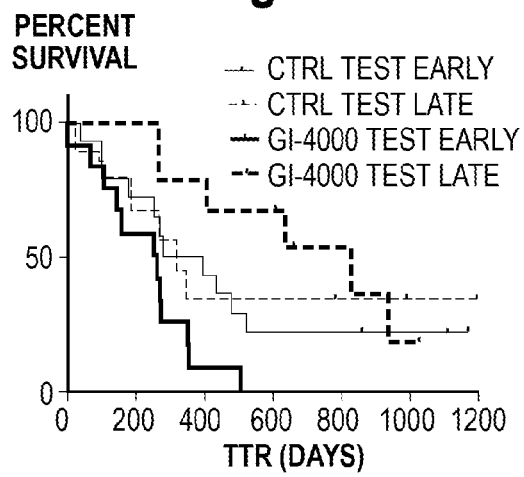

Two other quantities relevant to the performance of the CMC/D classifiers we studied using these training/test set realizations were the ratio of the HRs between Early and Late classifications for the GI-4000 test set relative to the control test set and the difference in median TTR between the Late group for the GI-4000 test set and the control test set. These are shown for the original group labels and the updated group labels in FIG. 8. The center of the distribution of ratio of HRs between Early and Late classifications for the treatment arms gets moves to the right, indicating improved predictive performance of the CMC/D classifiers. The distribution of difference in median TTR between Late groups in the two treatment arms gets narrower with fewer outliers, indicating more reproducible performance across training/test set realizations for this measurement of performance.

These analyses indicate that it is important how the samples are split into training and test sets. While the majority of training/test set splits yields final CMC/D classifiers that have some predictive power for the addition of GI-4000 to gemcitabine, certain splits yield exceptionally good or poor performance. These exceptional results are presumably due to the particulars of the small training and test sets and these classifiers should be avoided as being possibly overfitted to the data. In this project, to avoid overfitting as much as possible, CMC/D classifiers were selected that had "typical" performance within the training/test set splits. The Kaplan-Meier plots for several candidate final CMC/D classifiers of good, but not exceptional, performance are shown in FIG. 9.

The difference between the four final CMC/D classifiers resulting in the data shown in FIG. 9 is the training/test set split realization that produced them. Each classifier had a different training/test set realization. Otherwise, they were all generated using the same methodology. They all use the same 100 mass spectrometry feature values (Example 1 Appendix B), mini-classifiers using values of s=1 and s=2, the same value of K in the KNN classifier for each mini-classifier (K=5), the same filtering criteria, the same number of drop out iterations and even the same seed for the random number generator. The mini-classifiers that pass filtering are different for each training/test set split realization, as are the weights of these mini-classifiers assigned during the logistic regression process. However, to produce them, the only difference in the input to the CMC/D process is the different training/test set split. All other parameters are identical.

Of these four candidate final CMC/D classifiers, the first (top left panel of FIG. 9) was selected as it had solid performance on all of our evaluation criteria and exhibited a small split between control test groups. We do not want the control group to split in the opposite direction much because we want the classifier to show something that is particular to the GI-4000+gemcitabine treatment—i.e. we do not expect that it is biologically reasonable to get a classifier that shows that Early recurrence patients do worse on GI-4000+gemcitabine than Late recurrence patients and have the opposite behavior for the control treatment. We also do not want the control group to separate in the same direction as GI-4000, as then the predictive power between treatments is diminished.

For this classifier (top left panel of FIG. 9) Kaplan-Meier plots are shown for TTR and OS (overall survival) in FIGS. 10A-10D for the GI-4000 test set with the whole of the control arm. (Note that the training portion of the control arm was only used indirectly in classifier training in the filtering of the "mini-classifiers".) Updated outcome data recently provided allowed the reassessment of performance and this is also shown in FIGS. 10A-10D.

Figure 10A:
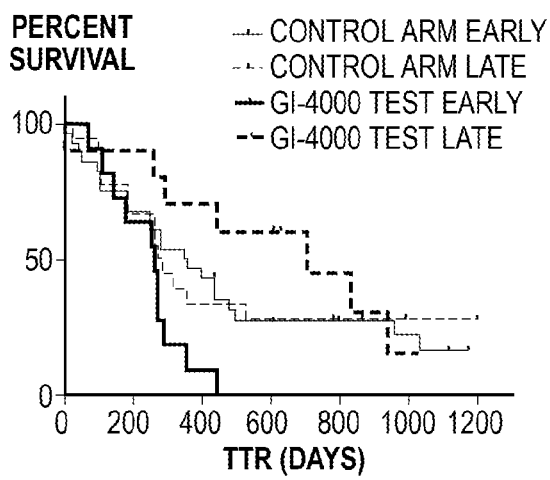
FIGS. 10A-10D shows Kaplan-Meier plots of TTR and overall survival (OS) for the selected CMC/D classifier using original (panels 10A and 10B) and updated outcome data (panels 10C and 10D). Performance measures for the classifier given were calculated using updated outcome data.
Figure 10B:
Figure 10C:
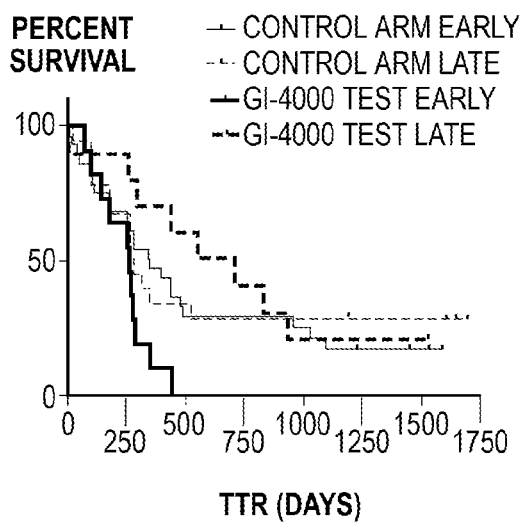
Figure 10D:
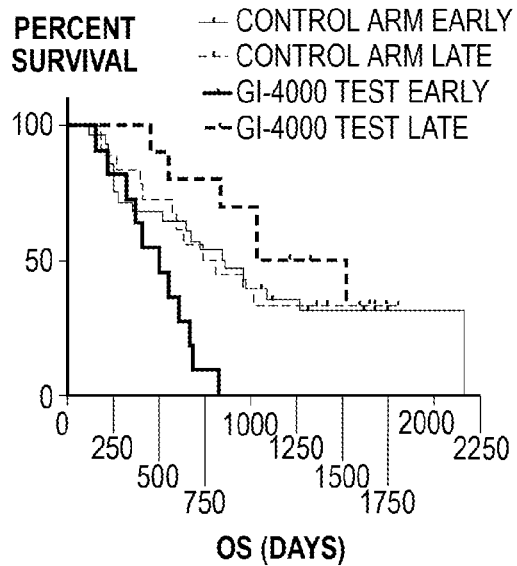

FIGS. 10E-10I are the plots of recurrence free survival (RFS) and overall survival (OS) for patients in the GI-4000+gemcitabine study as shown in FIGS. 10C and 10D, but plotted in pairs for ease of reference. In these Figures, "BDX-001" represents the predictive test described in Example 1. The class label "+" is equivalent to "late" in the above discussion, and is generated for those patients who are predicted to obtain benefit from the combination of GI-4000 and gemcitabine in treatment of pancreas cancer. The class label "–" is equivalent to the class label "early" in the above discussion, and is generated for those patients who are not predicted to obtain benefit from the combination of GI-4000 and gemcitabine. In FIGS. 10G, 10H and 10I, "placebo" means those patients who patients who were given the combination of gemcitabine plus a placebo in the GI-4000+gemcitabine study.

FIG. 10E illustrates that the test of Example 1 identifies a 12.2 month difference in median RFS (mRFS) in the GI-4000+gemcitabine treatment group. Such patients are identified by the classifier generating the "+" or "late" class label for the patient's mass spectrum.

FIG. 10F illustrated that the test of Example 1 identifies a 25.8 month improvement in OS in the GI-4000+gemcitabine treatment group for those patients having the "+" or "late" class label.

FIG. 10G illustrates that there was no difference in OS in the placebo+gemcitabine group in the GI-4000+gemcitabine trial for those having the + or – class label, indicating the predictive power of the test.

FIG. 10H illustrates that the test of Example 1 selects patients treated with GI-4000+gemcitabine that have a better recurrence free survival, and in particular shows that this group shows 11.7 month (21 months vs. 9 months) improvement in mRFS compared to the gemcitabine+placebo.

FIG. 10I illustrates improvement in median overall survival of 16.6 months (42 months vs. 25 months) for those patients treated with GI-4000+gemcitabine as compared to gemcitabine+placebo.

Example 1

Conclusions

We applied newly developed classification techniques, CMC/D, to the GI-4000 data set. This enabled us to split the data into separate training and test sets. To avoid small set bias we evaluated the procedure over many possible splits into training and test sets. An analysis of test set misclassifications allowed us to refine the training set labels resulting in more accurate group definitions of Early and Late.

The resulting CMC/D classifier was predictive for selection of patients benefitting from the addition of GI-4000 to gemcitabine, i.e. it showed clear treatment benefit of GI-4000+gemcitabine over gemcitabine alone in the Late but not the Early group. The median estimated benefit of GI-4000+gemcitabine over gemcitabine in the Late group is over 300 days for TTR, and over 400 days for OS.

We checked that this test is not overfitted to a particular training/test configuration by selecting a test as a final assay which is typical in the distribution of training/test configurations. While it may be possible that another test (classifier) may have been more effective, we believe that the selected test is a good compromise between efficacy and generalization.

As a result of this analysis, we believe that the addition of GI-4000 to gemcitabine is effective in patients selected by the test label Late by our CMC/D classifier. The Late patients represented ~43% (39 of the 90) of the total samples analyzed (see classification Example 1 appendix F).

One further embodiment of this invention is a method of guiding treatment for pancreatic cancer patients, in the form of predicting whether the patient will benefit from the combination of GI-4000+gemcitabine, using a classifier generated in accordance with the described method operating on a mass spectrum of a blood-based sample of the patient, and if the class label produced by the classifier is "Late" or the equivalent, the patient is predicted to benefit from the combination treatment and the treatment is administered. A further embodiment of the method is a method of treating a pancreatic cancer patient comprising the step of administering GI-4000+gemcitabine to the patient, the patient being selected for such treatment by means of a classifier operating on a mass spectrum of a blood based sample of the patient, wherein the classifier is generated by the CMC/D method described herein.

Example 2

Classifier Generation System and Sample Testing System

The CMC/D classifier development methodology can be implemented as a tangible classifier development system in the form of a mass spectrometer (or other measuring instrument) which is used to obtain mass spectral (or other) data from a plurality of samples (e.g., a classifier development set of samples) and a general purpose computer having a processing unit which executes code implementing the CMC/D classification method. In particular, the computer includes a machine-readable memory (e.g., hard disk) storing the measurement data. The computer also stores executable code which performs pre-processing of the measurement data, e.g., background subtraction, spectral alignment and normalization, as described above, and stores integrated intensity values at particular features used for classification, such as for example the integrated intensity values for the features listed in Example 1 Appendix B.

The computer also stores executable code for constructing a multitude of individual mini-classifiers using sets of features from the samples up to a pre-selected feature size (s, integer). In one embodiment, the code includes a KNN classification algorithm (known in the art) which is applied to a feature or features in the mass spectrometry data and compares the feature values to a subset of the development set of samples (e.g., a training set of class-labeled mass spectral data). The KNN algorithm generates a class label based on nearest neighbors in the feature space.

The code then tests the classification accuracy, or some alternative performance metric, of each of the individual mini-classifiers to classify the biological samples in a given set of samples (e.g., the training set) and retains those mini-classifiers whose performance exceeds a pre-defined threshold or is within pre-defined limits to arrive at a filtered set of mini-classifiers.

The code then generates a master classifier by repeatedly conducting a logistic training of the filtered set of mini-classifiers to the classification labels (using equation 1) for the samples using extreme dropout, by randomly selecting a small fraction of the filtered mini-classifiers and conducting logistical training on such selected mini-classifiers. A master classifier can be generated as an average over all the logistic regression trainings of the dropout iterations. In the GI-40000 example above, the master classifier is represented in the computer memory as a weighted combination of the mini-classifiers using a single feature for classification (s=1) and the mini-classifiers using two features for classification (s=2) which passed the filtering criteria.

The master classifier can be evaluated against a test set split or subset of the development set, the evaluation also carried out over multiple different splits of the development set into training and test sets, and a final classifier can be defined by selecting one of the master classifiers resulting from a particular training and test set split, or alternatively by retaining all of the master classifiers from each training and test set split and using a majority vote from each of the master classifiers to assign a label to a sample under test, or from some other combination of the master classifiers resulting from each realization of the test set/training set split, such as a weighted combination of all the master classifiers.

This final classifier is then used for classification of a test sample, e.g., a blood-based sample of a cancer patient, to predict in advance of treatment whether the patient is likely to benefit from the combination of GI-4000+gemcitabine. If the class label assigned to the mass spectrum of the sample is Late, that means the patient is likely to benefit from the addition of GI-4000 to gemcitabine. If the class label is Early, the patient is not likely to benefit from the addition of GI-4000 to gemcitabine and therefore directed to gemcitabine monotherapy or other treatment options for cancer.

The classification system described above can be implemented at a laboratory test center testing samples commercially and providing a service for clinics, hospitals, oncologists and other health care providers with test results as to patient benefit from cancer-targeting drugs. Of course, the classifier development methodology can be used for other purposes, such as diagnostic purposes.

FIG. 11 is a flow chart illustrating the classifier development process described in Examples 1 and 3 in more detail. The classifier development process would be typically implemented in a computing system taking the form of general purpose computer storing a classifier development set of measurement data, e.g., in the form of mass spectrometry data, and executable code implementing the modules shown in the Figure.

As shown in FIG. 11, the process begins with a classifier development set of data 1100, for example a set of mass spectrometry data obtained from a mass spectrometer (not shown) from blood-based samples of human patients. The process shown in the flow chart of FIG. 11 is not limited to any particular form of data, as mentioned earlier, e.g., genomic data (mRNA transcript expression data, protein expression data, etc.). However, the example of mass spectrometry of blood-based samples is suitable for the present discussion and not meant in any way to be limiting.

At step 1102, the groupings (class labels) in the classifier development set 1100 are defined, such as for example "early" and "late" groups 1104 and 1106, respectively. In this example, the "early" group 1104 consists of the set of spectra in the development set 1100 which are associated with patients that had relatively early recurrence of disease after administration of an anti-cancer drug. Conversely, the "late" group 1106 consisted of the set of spectra in the development set 1100 which was associated with relatively late recurrence of disease after administration of the anti-cancer drug. The defining of class labels can be done by a human operator or by machine (computer) by investigation of the clinical data associated with each of the samples. Further considerations in defining the Early and Late groups are described in detail below. The split of the development set 1100 into early and late groups may or may not be into groups with even numbers of samples.

At step 1108, both the early and late sample groups are split into training and test sets. This split at step 1108 is not necessarily into equal groups. We could split in a 2:1 or other ratio. If we had a very large set, we might not want to use a really large training set. If we had very limited numbers of samples, we could use more samples in training set than in the test set. This splitting at 1108 results in two groups: training set 1112 and test set 1110 (each training and test set including both "early" and "late" samples/data from the development set 1100).

As shown in FIG. 11, the training set 1112 is then subject to classifier development steps 1120, 1126 and 1130. In step 1120, a multitude of KNN based mini-classifiers are created, as explained above in detail previously. These mini-classifiers may use only 1 (s=1) or perhaps 2 features (s=2) in the mass spectra data set for classification. As shown in the balloon 1122, the KNN mini-classifiers use subsets of features (integrated intensity values of m/Z features, as shown in box 1124) drawn from the entire feature space. The mass spectra could take the form of the "Deep MALDI" spectra as described in our earlier patent application serial no. U.S. Ser. No. 13/836,436 filed Mar. 15, 2013, also incorporated by reference herein. Alternatively, the mass spectra could take the form of typical "dilute and shoot" spectra from say 2,000 laser shots, or an average of several (e.g., three) 2,000 shot spectra with implementation of spectral filtering at the time of spectra acquisition. The features used for classification in the mini-classifiers are integrated intensity values, namely the area under predefined peak positions within a specified m/Z range. The generation of integrated intensity values for classification in the KNN mini-classifiers is preferably performed after pre-processing steps, such background subtraction, normalization and alignment of the spectra have been performed. These steps, and the implementation of the KNN mini-classifiers, is performed by computer code within a general purpose computer.

At step 1126, a filtering of the KNN mini-classifiers generated at step 1120 is performed, to only save those mini-classifiers that had an acceptable level of performance. This is explained intuitively in FIG. 11. Each mini-classifier is assessed relative to a defined performance metric. In this step, only those mini-classifiers that had good classification performance are retained, as indicated by the plus sign at 1128.

At step 1130, a master classifier is generated from the mini-classifiers that passed the filtering step after performing many logistic regression and drop-out regularization iterations, as explained above. This master classifier could be implemented as an average of the combination of the filtered classifiers after logistic regression and drop-out regularization. The data set forming this master classifier (MC) is indicated at 1132 and is stored in the memory of the computer executing the method shown in FIG. 11. (It will be noted that logistic regression with drop out is a presently preferred approach to a regularized combination method, but persons skilled in the art will appreciate that other approaches could be used, including the specific regularized combination methods discussed in the scientific literature recited previously.)

At step 1134, the performance of the master classifier generated at step 1130 is then tested by subjecting the test set split of the development set data (1110) to classification by the master classifier. (Again, the test set may be subject to pre-processing steps prior to execution of classification algorithm in the master classifier.) The results of the performance of the many master classifiers are evaluated and can be stored and represented for example as a histogram of Hazard Ratio distributions, as shown in FIG. 11 at 1138 or in FIGS. 6 and 7 in the previous description.

The steps 1108, 1110, 1112, 1120, 1126, 1130, 1132 and 1134 are repeated as indicated by the loop 1136 with a different split of the early and late sample sets into different training and test set realizations. The purpose of loop 1136 is to avoid training set/test set split bias. The result of each iteration of the loop 1136 is a different master classifier. The performance of the master classifier is evaluated for each sample the test set (1110) for each realization of the training and test set split.

At step 1136, the classifier performance data (e.g., histograms) from each training/test set split is analyzed. For example, as shown in FIG. 11 at 1138, each realization of the training/test set split produced a master classifier and a histogram of the hazard ratios of the classifications (early/late) produced by the many master classifiers can be created. The distribution of the hazard ratios can be used assess classifier performance, as explained previously. It will be noted that overfitting of a final classifier to the training data is minimized by the regularization step (1132) and selection of either a master classifier from one of the master classifiers having a typical performance, or using an combination approach, e.g., by averaging over all the master classifiers, e.g., using a majority vote algorithm from all the master classifiers, or applying a weighting to all of the master classifiers. Confidence in the final classifier performance estimates in the analysis step 1136 is enhanced by the observation of many master classifiers with similarly good performance.

There may be instances where particular samples (typically a small number) in the training set are often misclassified by a master or final classifier. In this situation, it may be useful to redefine the training labels for such samples, e.g., change or "flip" the label from "Early" to "Late". This is particularly relevant for classification problems where the training labels are hard to define, e.g. in tests for treatment benefit or relative treatment benefit. This is done at step 1142 and the process loops back to step 1102 and the splitting of the development sample set into "early" and "late" groups according to the corrected or new training labels proceeds for some subset of the samples. The process of splitting these groups into training and test set splits at step 1108 and the subsequent steps in the flow chart proceeds in a new iteration, resulting in a new master classifier and evaluation of the new master classifier performance at step 1136 and 1138. Step 1140 is not always necessary, e.g., where there are few or no instances of misclassification, in which case after the analysis step 1136 the processing proceeds directly to step 1144.

At step 1144, the procedure for specifying g a final test label for a sample to be tested is defined. The final test label for a sample can be specified in several ways, for example it can be defined as the result of a majority vote on the classification label of all the final master classifiers from all the training/test set splits. Alternatively, it can be defined as the label produced by a selected master classifier for a given training/test set split that provides typical performance, or alternatively by the use of a statistical analysis of the classification results produced by the master classifier e.g., using the procedures described in the following example.

Testing System

Figure 26:
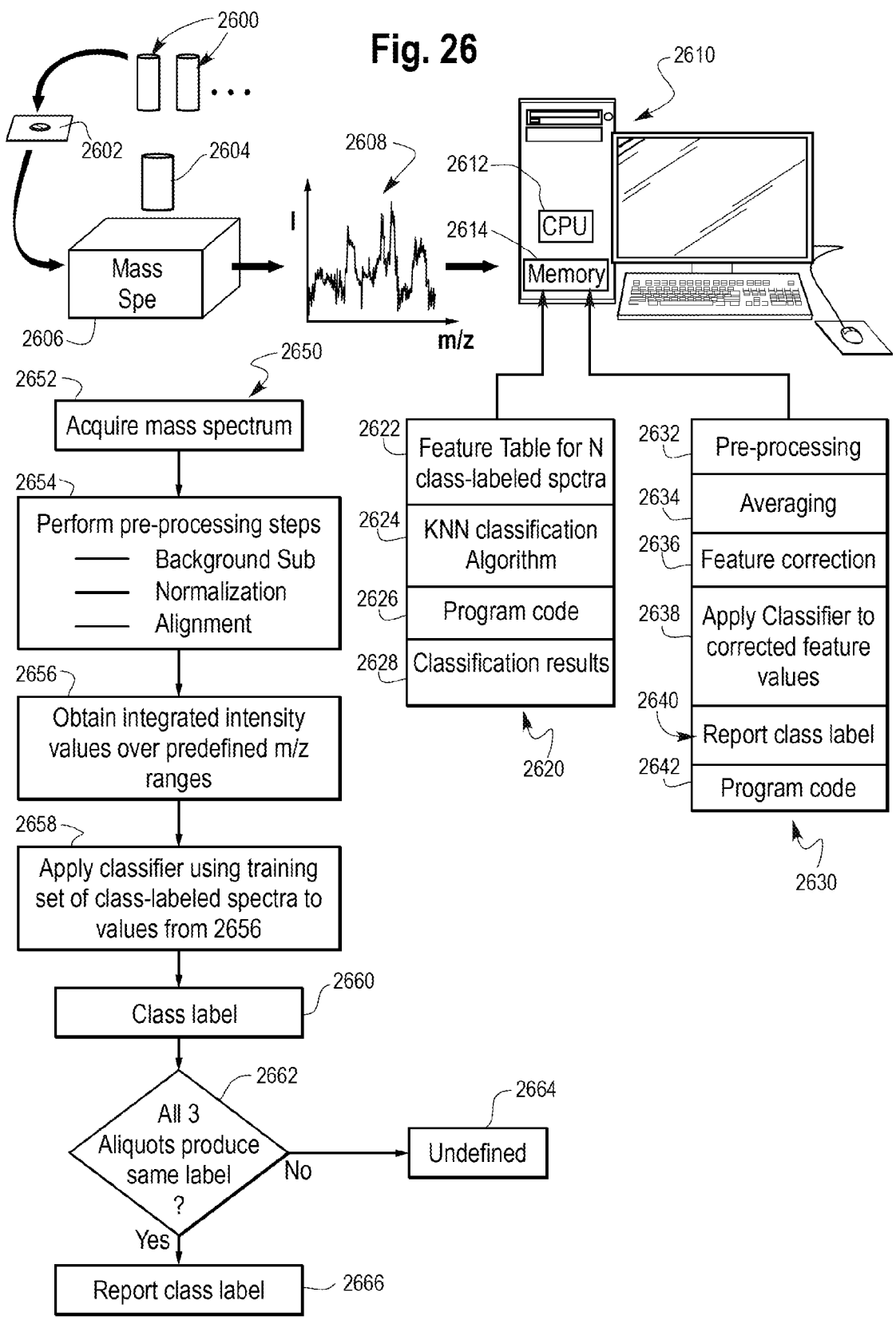
FIG. 26 is an illustration of a system for processing a test sample using a classifier generated in accordance with FIG. 11, including a mass spectrometer and a general purpose computer implementing a classifier coded as machine-readable instructions and a memory storing a training set of class-labeled mass spectrometry data.

FIG. 26 is an illustration of a system for processing a test sample using a classifier generated in accordance with FIG. 11, including a mass spectrometer 2606 and a general purpose computer 2610 implementing a CMC/D classifier 2620 coded as machine-readable instructions and a feature table 2622 forming a training set of class-labeled mass spectrometry data 2622 stored in memory 2614. It will be appreciated that the measurement instrument 2606 and computer 2610 of FIG. 26 could be used to generate the CMC/D classifier in accordance with FIG. 11.

The operation of the system of FIG. 26 will be described in the context of the test of Example 1, but it will be appreciated that the methodology described in this section can be used in other examples.

The system of FIG. 26 obtains a multitude of samples 2600, e.g., blood-based samples (serum or plasma) from cancer patients. The samples 2600 are used to make predictions as to whether the patient is likely to benefit or not benefit from a particular drug or combination of drugs. The samples may be obtained as serum cards or the like in which the blood-based sample is blotted onto a cellulose or other type card. Three aliquots of the sample are obtained. In one possible embodiment (as described below in Example 3 in FIG. 12, a reference sample 2604 may also be used).

The three aliquots of the sample are spotted onto a MALDI-ToF sample "plate" 2602 and the plate inserted into a measuring instrument, in this instance a MALDI-ToF mass spectrometer 2606. The mass spectrometer 2606 acquires a mass spectrum 2608 from each of the three aliquots of the sample. The mass spectra are represented in digital form and supplied to a programmed general purpose compute 2610. The computer 2610 includes a central processing unit 2612 executing programmed instructions. The memory 2614 stores the data representing the mass spectra 2608.

The memory 2614 also stores a master or final CMC/D classifier 2620, which includes a) a training set 2622 in the form of a feature table of N class-labeled spectra, where N is some integer number, in this example class-labeled spectra from patients enrolled in a clinical trial as described earlier, and each sample assigned a class label such as "early", "late", "+", "−", "good", "poor", etc., b) code representing a KNN classification algorithm, c) program code for executing the final classifier generated in accordance with FIG. 11 on the mass spectra of patients, including logistic regression weights and data representing master classifier(s) forming the final classifier, and d) a data structure 2628 for storing classification results, and a final class label for the test sample. The memory 2614 also stores program code 2630 for implementing the processing shown at 2650, including code (not shown) for acquiring the mass spectral data from the mass spectrometer in step 2652; a pre-processing routine 2632 for implementing the background subtraction, normalization and alignment step 2654, a module (not shown) for obtaining integrated intensity values at predefined m/Z positions in the background subtracted, normalized and aligned spectrum (step 2656), and a code routine 2638 for implementing the classifier 2620 using the training set 2622 on the values obtained at step 2656. The process 2658 produces a class label at step 2660. Program code 2642 includes code that makes a check (step 2662) to determine if all three aliquots of the sample produced the same class label. If no, the class label "undefined" or the equivalent is reported. If all three aliquots to the patient sample 2600 produce the same class label, the module 2640 reports the class label as indicated at 2666 (i.e., "early", "late", "+", "−", "good", "poor" or the equivalent).

The program code 2630 can include additional and optional modules, for example a feature correction function code 2632 (described in conjunction with the description of FIG. 12), a set of routines for processing the spectrum from a reference sample 2604 to define a feature correction function, a module storing feature dependent noise characteristics and generated noisy feature value realizations (see FIG. 12) and classifying such noisy feature value realizations, and modules storing statistical algorithms for obtaining statistical data on the performance of the classifier on the noisy feature value realizations. Still other optional software modules could be included as will be apparent to persons skilled in the art.

The system of FIG. 26 can be implemented as laboratory test processing center obtaining a multitude of patient samples from oncologists, patients, clinics, etc., and generating a class label for the patient samples as a fee-for-service. The mass spectrometer 2606 need not be physically located at the laboratory test center but rather the computer 2610 could obtain the data representing the mass spectra of the test sample over a computer network.

Example 3

Generation of CMC/D Classifier from Mass Spectrometry of Patient Blood-Based Samples for Non-Small-Cell Lung Cancer (NSCLC) Patient Selection for EGFR-I Drugs (VS 2.0)

Another example of the generation of a CMC/D classifier and use thereof to guide treatment of NSCLC patients will be described in this section. The generation of the classifier largely follows the method described above Example 1 and in the discussion of FIG. 11 above in Example 2. However, the processing of a test sample to make a prediction using the CMC/D classifier in this example makes use of reference spectra, as well as additional adjustments to the processing of the spectra to take into account restrictions on machine qualification and spectral reproducibility which were presented in this example. The generation of the final classification label for a sample under test also makes use of feature-dependent noise characteristics and other techniques which will be described in greater detail below in conjunction with FIG. 12. Nevertheless, this section will demonstrate a further example of the generation of a CMC/D classifier from mass spectral data and the use thereof to make predictions in advance of treatment on whether a patient is likely to benefit from administration of a drug.

The VeriStrat test described in prior U.S. Pat. No. 7,736, 905 (referred to herein occasionally as "VS 1.0"), among other things, makes a prediction in advance of treatment whether a NSCLC patient is a member of a class, referred to as VeriStrat "Poor", which is not likely to benefit from EGFR-Is such as erlotinib and gefitinib in treatment of NSCLC. The prediction is based on a mass spectrum of a blood-based sample from the patient and the use of a classifier implemented in a computer. The results from recent EGFR-I trials in treatment of NSCLC, known as the TAILOR and DELTA trials, indicate that erlotinib may be the inferior treatment in an EGFR wild type population. Consequently, the use of Tarceva (erlotinib) has fallen outside of front-line treatment for patients whose tumor shows EGFR sensitizing mutations, and as salvage treatment in higher lines.

The test described in the '905 patent does not describe how to make a prediction of whether an EGFR-I such as erlotinib would be a superior treatment over chemotherapy, even in those patients testing VeriStrat "Good" in the VS 1.0 test. Subsequent studies, such as the PROSE study[1] were not designed to show superiority of one treatment over another. Furthermore, while the small number of the VeriStrat "Good" patients in the PROSE study was by far too small to argue for equivalence of erlotinib and chemotherapy treatments, there is also no evidence that one treatment is superior to the other.

[1] See V. Gregorc et al., Randomized Proteomic Stratified Phase III Study of Second-Line Erlotinib Versus Chemotherapy in Patients with Inoperable Non-Small Cell Lung Cancer, presented at ASCO annual meeting June 2013.

The present inventors have been developing and applying our new CMC/D classifier development methodology to this problem. During the development of our approach to probe deeper into the serum proteome, using what we have called "Deep MALDI", we have also developed tools and algorithms to increase our ability to enhance the peak content of standard mass spectral acquisition techniques by combining the spectra from multiple technical replicates of a standard acquisition, such as a standard "dilute and shoot" mass spectral data acquisition used in the VS 1.0 test and described in U.S. Pat. No. 7,736,905. An example of this combination of spectra from multiple technical replicates of standard "dilute and shoot" mass spectral acquisitions is described in this example.

A goal of the recent classification effort was to develop a new test (referred to herein as VeriStrat 2.0 or VS 2.0) that identifies a group of NSCLC patients having more benefit from erlotinib than chemotherapy. This new test, and the method of generating the classifier used in the test, is described in this Example. In one possible implementation of the test, the test is based on standard MALDI-ToF mass spectral acquisition, e.g., 2000 shot "dilute and shoot" spectra. As a classifier development set (FIG. 11, 1100), we had available to us a subset of samples from the original development set and initial validation sets used in generating the VS 1.0 test of the '905 patent. The resulting test as described in this document shows superiority of erlotinib over chemotherapy in a selected subset, while retaining the predictive character of our original VeriStrat test. The test described in this document explains how to identify if a NSCLC patient is a member of this subset of patients that are likely to obtain more benefit from an EGFR-I such as erlotinib than chemotherapy. This subset is associated with the class label "Late" in this following example. The class label could be given some other equivalent name in order to identify such patients, such as "EGFR Benefit", "Positive", "+", or the like. Thus, the particular moniker for a class label is not important.

The test described in this document also features a classification algorithm in which patients identified as Poor or the like are predicted to not benefit from EGFR-Is in treatment of NSCLC cancer. A third class label can be assigned to the patient sample under test, referred to here as "Intermediate", which is associated with patients that are predicted to perform in clinically meaningful terms similarly on either chemotherapy (docetaxel, pemexetred) or an EGFR-I such as gefitinib or erlotinib.

Patient Population and Available Samples

The following cohorts of patients had samples available for this project: sample sets known as "Italian A", "Italian B", "Italian C." Italian A and B were cohorts of patients with advanced NSCLC treated with gefitinib used in the development and validation of the original VeriStrat test. See generally, U.S. Pat. No. 7,736,905; Taguchi et al., JNCI 99: 838-846 (2007). Italian C was a cohort of patients treated in advanced line with a variety of chemotherapy regimens.

The initial plan was to directly create a predictive classifier to identify patients having better outcomes on gefitinib compared with chemotherapy by using all three cohorts of patients. However, as overall the outcomes in the Italian C cohort within the subset of patients for whom progression-free survival (PFS) data were available were generally inferior to those of the Italian A and B cohorts, this method did not work well.

Initial efforts to use all samples to create a classifier identifying patients who had good outcomes on gefitinib therapy produced many classifiers that produced classifications having extremely strong overlap with original VeriStrat classifications, i.e. we were able to produce many classifiers having similar performance and producing very similar sample classification compared to original VeriStrat using CMC/D methodology and different features. This was true even when features in regions of the spectra overlapping with mass spectral features from VeriStrat were excluded from the process.

Therefore, it was decided to restrict the classifier generation process to samples that yielded an original "VeriStrat Good" classification, i.e. to design a classifier that splits the VeriStrat Good samples into patients with better or worse outcomes on EGFR-Is. Finally, as there are reasons to believe that patients with performance status (PS) 2 and patients in fourth line of therapy are generally likely to receive very little benefit from gefitinib therapy, samples from these patients were also not included in classifier development. Other samples from the three cohorts, including VeriStrat Poor samples from the original development set, samples from the Italian C cohort, and samples from patients with PS 2 and in fourth line therapy, were still used in classifier evaluation during the development process. Moreover, in a clinical application of the CMC/D classifier described later on in this section, the training set used for classification included feature values from spectra from patients having a class label VeriStrat Poor.

The list of samples used during classifier development is given in Example 3 Appendix A.

The development of the new CMC/D classifier is depicted in the diagram shown in FIG. 11. The diagram is discussed at length above. Basically, the development sample set (Example 3 Appendix A) was divided into two groups ("Early" and "Late") depending on whether the patient associated with the sample experienced early or late progression of disease after commencement of treatment with an EGFR-I. See FIG. 13, discussed below. The goal of this development is to both generate the class labels identifying patients benefit from a drug (in this example an EGFR-I as compared to chemotherapy) as well as a test to identify patients belonging to this class at the same time. The results of this process are the (new) class labels and a test to assign a patient to one of the classes. Those patients that experienced late progression can be considered for the initial assignment of class labels as those patients that benefitted more from EGFR-I treatment than an alternative such as chemotherapy, and had assigned to their specimen the class label "Late". Those patients that experienced early progression can be considered, as an initial estimation, as those patients that did not benefit more from EGFR-I treatment than chemotherapy, and had assigned to their specimen the class label "Early".

From these two groups of samples, the groups were separated into training and test sets of approximately equal size (FIG. 11, step 1108). The training sets were subject to the CMC/D classifier generation steps 1120, 1126, 1130, 1134 shown in the right hand side of FIG. 11, using features in the MALDI ToF spectrum of their serum samples. The test samples were classified by the resulting master classifier (MC) and the MC performance was evaluated at step 1134 over the test set of samples (1110). The process looped over many training/test set split realizations (250 in this example). Samples subject to misclassification were given redefined training labels, and the CMC/D classification and evaluation steps were repeated (steps 1140, 1142). This label re-definition process was repeated twice in the development of this test. A final classifier was then selected from the MCs, in this instance a majority vote of all 250 classifiers resulting in each of the training/test splits. Alternative constructions for the final classifier are also possible, such as selection of one MC that provides "typical" performance, an average of the 250 final MCs, or otherwise (see FIG. 12 for example).

Spectral Acquisition and Pre-Processing

The mass spectra used in classifier generation in FIG. 11 are acquired by a mass spectrometer from a blood-based sample. The mass spectra are subject to pre-processing steps prior to classification. The steps are described in this section.

a. Generation of Mass Spectra Used During Development

Spectral acquisition of blood-based samples was performed using qualified mass spectrometry machines used for VeriStrat testing (for details see Appendix H) manufactured by Bruker. Machine qualification can be performed using the methods of the patent of J. Röder et al., U.S. Pat. No. 8,467,988, the content of which is incorporated by reference herein.

The spectra were acquired in triplicates of 2,000 acquired shot spectra. In this particular instance, the spectra were filtered at the time of acquisition using Bruker Flexcontrol settings to only acquire spectra with desired qualities. The number of actual shots the sample was subjected to is higher than 2000, and varies from sample to sample and from MALDI spot to MALDI spot. The triplicates of spectra acquired for each sample were aligned and averaged to produce one 6,000 shot spectrum per sample.

b. Background Estimation and Subtraction

The first step in pre-processing the averaged spectra was background estimation and subtraction. The background component of the averaged spectra was estimated using the single window method and a multiplier of 100. The estimated backgrounds were then subtracted from the averaged spectra.

c. Spectral Alignment

In any mass spectra there are slight discrepancies with respect to the translation of time-of-flight numbers to m/Z values. We identified a set of peaks that are present in the vast majority of the mass spectra and rescaled each spectrum's m/Z values such that the sum of the squared deviations of the common peaks in each individual spectrum to the reference set is as small as possible. This process leads to better resolution of close (in m/Z) features.

d. Normalization

In order to obtain features that differentiate between clinical groups, we need to measure the intensity of peaks from different samples and compare their values. The overall amount of ionized protein is not controllable within the MALDI process, and so we can only measure relative peak intensities. To do this we need to normalize the spectra. In order to avoid propagating the variability of peak intensities from peaks that are either intrinsically variable or which correlate to the clinical status of the patient to stable peaks during normalization, care needs to be taken in determining which regions of the spectrum can be used for normalization. The m/Z regions used for normalization were selected using a partial ion current normalization tool. Partial ion current normalization in known in the art and the interested reader is directed to the discussion of normalization procedures in U.S. Pat. No. 7,736,905.

e. Feature Definitions and Feature Tables

In order to define possible candidates for peaks that can differentiate between clinical groups (i.e., m/Z features used in KNN classification) we located peaks in the pre-processed spectra and defined a range in m/Z around each peak's maximum. These ranges in m/Z define features that are used for all further analysis. We selected 76 features as possible candidates for differentiating between groups and calculated the integrated intensity of each of these features for each spectrum. In this way we obtain a feature value for each feature for each spectrum. The tabular listing, rows are spectra, columns are features, of these integrated intensities (feature values) is referred to as the feature table, which is stored in memory of a general purpose computer implementing the method of FIG. 11. Two of the features defined, at m/Z=7616 and 14392 were not used during the CMC/D classifier development process, due to lack of sufficient feature quality (noise) on re-inspection. We observed that some of the samples showed substantial levels of oxidization leading to double peak structures or shift of similar peaks. In order to avoid missing the oxidized version of underlying polypeptides we used very wide feature definitions. The definitions of the 74 m/Z features used in the CMC/D classifier generation process are provided in Example 3 Appendix B.

CMC/D Classifier Development Method

Selection of Early/Late Progression Groups and Training and Test Sets (Steps 1102 and 1108, FIG. 11)

Figure 13:
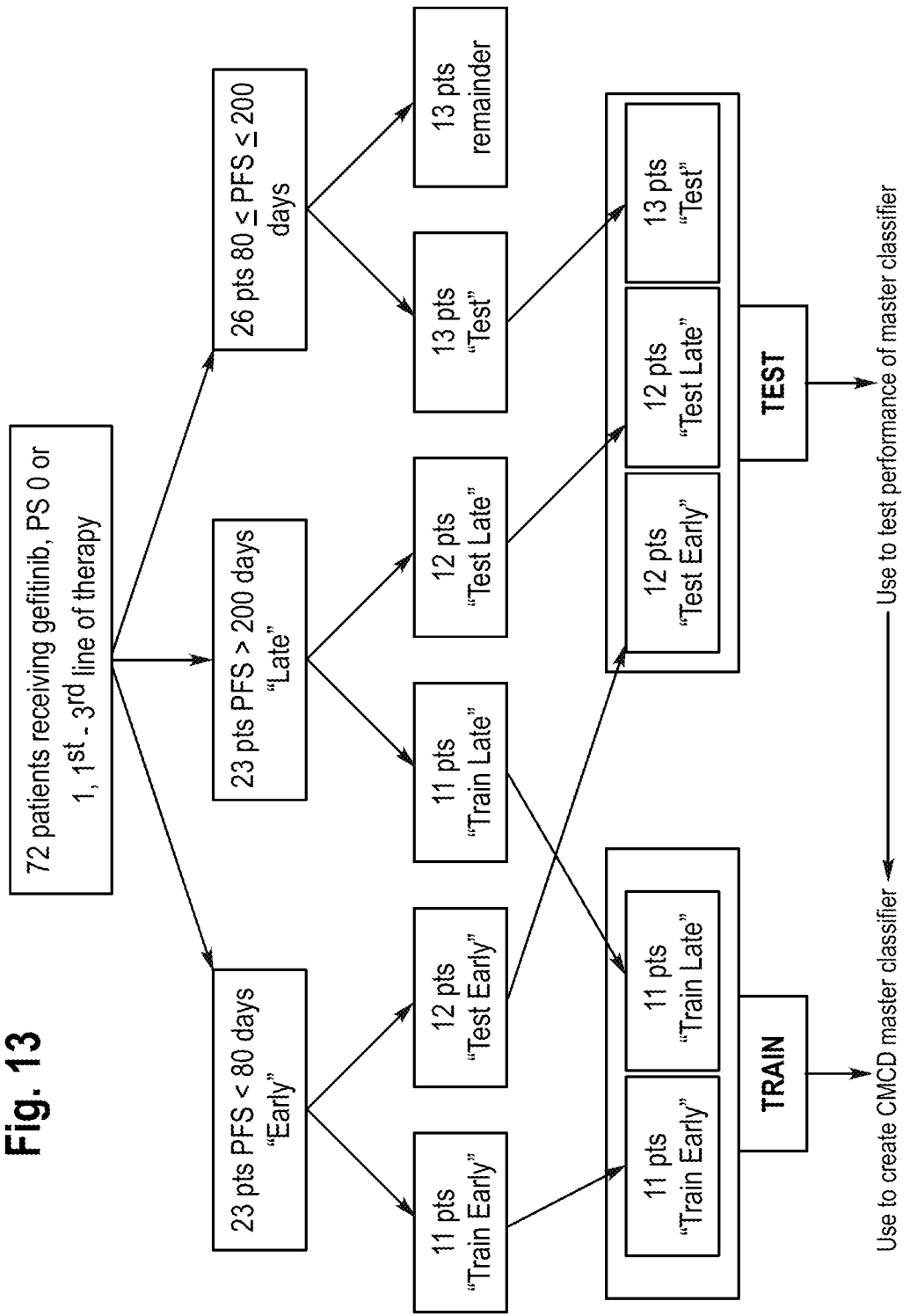
FIG. 13 is an illustration of the initial assignment of class labels and slit into training and test sets in the NSCLC/EGFR-I CMC/D classifier described in Example 3.

From clinical data it is not possible to determine, with certainty, which patients benefit more or less from a given therapy. As a first approximation to defining classes of patients benefitting more or less from treatment with an EGFR-I (i.e., assigning the initial class labels to the samples), in step 1102 (FIG. 11) patients with PFS less than 80 days were defined as "Early" (Early Progression indicative of possible little benefit from therapy) and patients with PFS in excess of 200 days were defined as "Late" (Late Progression indicative of possible greater benefit from therapy). See FIG. 13. This resulted in 23 patients in the "Early" group and 23 patients in the "Late" group. These are listed in Example 3 Appendix C with their assigned class label. These were then split into training (11 "Early" and 11 "Late") and test sets (12 "Early" and 12 "Late"), step 1108 in FIG. 11, stratified by line of therapy and performance status (PS). It is possible that some training/test splits can produce training sets that are particularly good or poor for creation of a classifier and test sets that are particularly easy or difficult to classify. Hence, the stratified training/test split was done randomly 250 times (indicated by the loop 1136 in FIG. 11). Each split provides a training set 1112 leading to generation of a CMC/D master classifier (MC), step 1130 in FIG. 11, the performance of which can be assessed on the corresponding test set. (Step 1134) To provide test sets that are representative of the population in terms of distribution of PFS times, half of the patients with PFS between 80 and 200 days with PS 0 or 1 and in first to third lines of therapy were randomly selected for inclusion in the test set. The initial assignment of class labels and split into training and test set are shown in FIG. 13.

Creation of Mini-Classifiers (Step 1120, FIG. 11)

For a given training set it is possible to create many individual K-nearest neighbor (KNN) classifiers using subsets of the 74 features. These individual KNN classifiers, defined by the samples in the training set and the particular subset of features define a "mini-classifier" (mC). For this project K=5 in the KNN algorithm was fixed throughout.

All mCs were considered that used one of the 74 features (s=1) or a pair of the 74 features (s=2). This gave a total of 2775 mCs for each training set.

Filtering of Mini-Classifiers (Step 1126, FIG. 11)

The mini-classifiers generated in step 1120 are pruned based on filtering by performance of the mCs on the training set. This was done using the ERRORS method of the CMC/D process with Jmin=0.7 and Jmax=0.9. This means that each mC was applied to its training set. The accuracy with which it assigned "Early" and "Late" labels was calculated. If this accuracy was between 0.7 and 0.9, the mC passed filtering and could be used to make the master classifier (MC). If the accuracy lay outside of this range, the mC failed filtering and dropped from the CMC/D process. The number of mCs passing filtering depends on the training set, i.e. the particular training test split realization, but typically was of the order of 1000-1500.

In essence, the ERRORS method assesses the accuracy of the classification given by the mC. In the filtering process each mC is applied to each member of the training set and this gives us a classification for each member of the training set. We know the definition (class label) we have assigned to each member of the training set, so we just calculate the proportion of correct classifications for each mini-classifier. We chose that this accuracy (proportion of correct classifications) had to lie between 0.7 and 0.9.

We intentionally did not push the upper limit up (Jmax) to the perfect classification of 1.0. Firstly, there are not many mini-classifiers that achieve this accuracy, but secondly, and more importantly, we are trying to avoid over-fitting at each stage of the process when generating a classifier. Mini-classifiers that achieve exceptionally high accuracy are likely to be 'special' and not 'typical', resulting from some peculiarities of the training set and features, and not likely to generalize well. So, we chose not to include mini-classifiers that are 'too good' into the master classifier. It is quite interesting to note that when filtering criteria are set too extreme and mini-classifiers that have exceptionally good performance are combined, the overall classifier produced turns out to have poorer performance.

Creation of Master CMC/D Classifier Using Logistic Regression with Drop Out (Step 1130)

The mCs that passed filtering were combined into one master classifier (MC) by training a logistic regression using the Late and Early training set labels with extreme drop out as a regularizer. Ten thousand drop-out iterations were carried out, in each of which 5 mCs were randomly selected and combined using logistic regression. The logistic regression weights for each mC (see equation 1, supra) from each drop-out iteration were averaged to produce the final weights for the logistic combination into a final MC.

CMC/D Classifier Performance Assessment (Step 1134, 1136, FIG. 11)

Figure 14C:
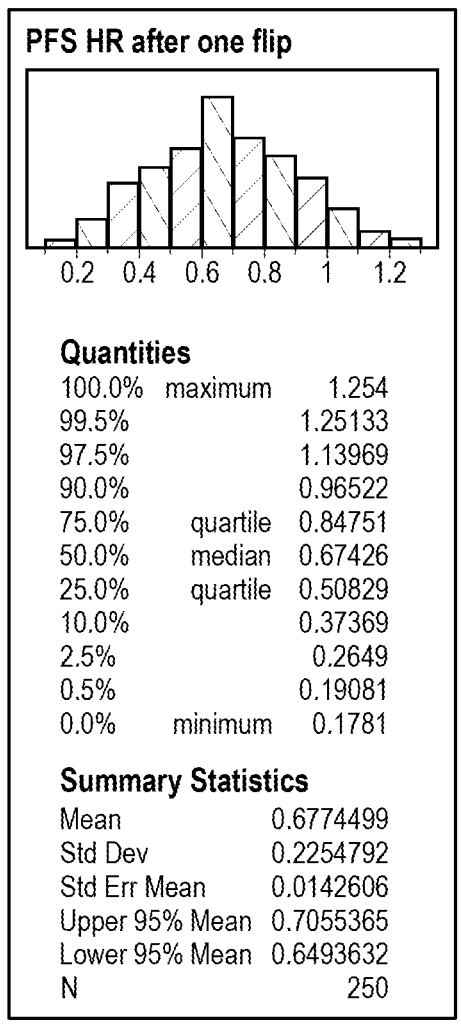

Once the master classifier was created for a given training set realization, it was evaluated by running the classifier on the test set (1110) and on spectra obtained from samples from the Italian C cohort in step 1134. This process was performed for each of the 250 training and test splits. Quantities evaluated included hazard ratio (HR) between "Early" and "Late" classifications of the test set and for the Italian C cohort for overall survival (OS) and PFS and medians for "Early" and "Late" classifications for the test set and Italian C cohort. The HR distributions for PFS and OS generated are shown in the FIGS. 14A-B. In addition, individual classifications of class labeled samples were examined when they were in the test set. Many samples repeatedly were assigned classifications that did not match their PFS-defined labels. These samples were identified and are listed in Table 3.

TABLE 3

| Samples persistently misclassifying Sample ID |
|---|
| ICA_11 |
| ICA_12 |
| ICA_18 |
| ICA_20 |
| ICA_21 |
| ICA_22 |
| ICA_36 |
| ICA_38 |
| ICA_39 |
| ICA_45 |
| ICA_51 |
| ICA_68 |
| ICB_22 |
| ICB_3 |
| ICB_38 |
| ICB_49 |
| ICB_61 |

Refinement of Initial Class Label Assignment (Step 1140, FIG. 11)

The class labels of the samples that persistently misclassified over many training/test splits, listed in Table 1, were flipped ("Early" to "Late" and "Late" to "Early"). This produced a new set of training labels for the CMC/D classifier generation process to be carried out again.

Figure 14D:
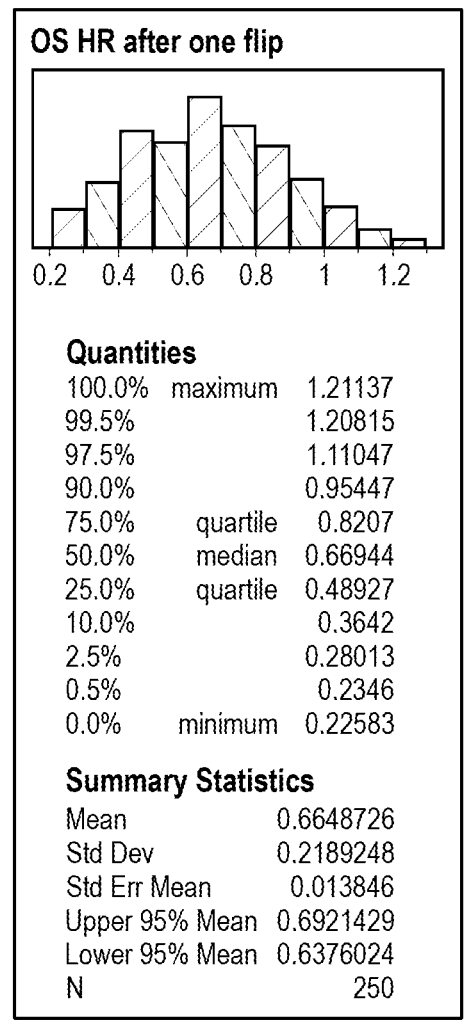
Figure 14E:
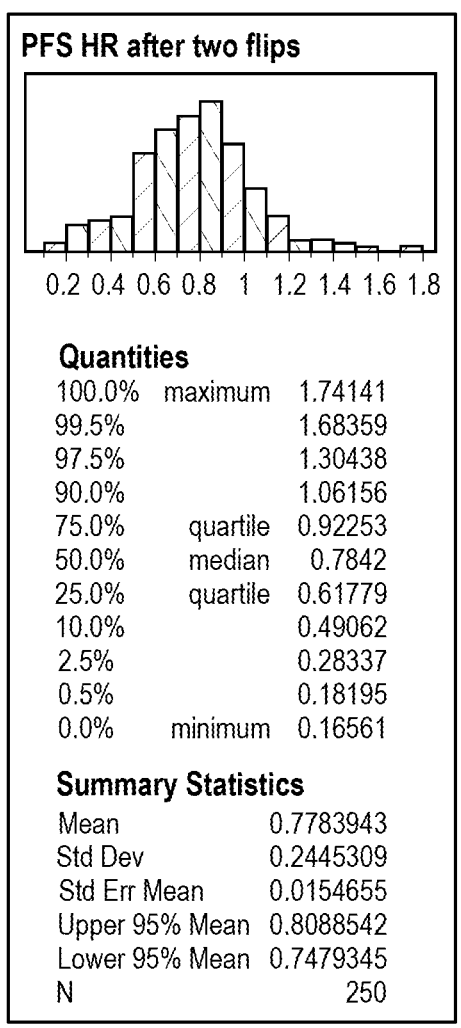

Using the new labels, the "Early" and "Late" samples were again randomized into training and test sets 250 times, as before stratified on line of therapy and PS. Mini-classifiers were created as before and filtered using identical criteria. These filtered mCs were combined using logistic regression with drop-out to create MCs and the performance of the MCs was assessed on the new test sets. The distributions of HRs for PFS and OS generated are shown in the FIGS. 14C and 14D. The distributions of HR for PFS and OS generated after two flips are shown in FIGS. 14D and 14E.

Several samples were identified that persistently misclassified when part of the test set. These are listed in Table 4.

TABLE 4

Samples persistently misclassifying
after first set of class label flips
Sample ID

ICA_20
ICA_21
ICA_38
ICA_39
ICA_45
ICB_12
ICB_40

The class labels of the samples that persistently misclassified after the second running of the CMC/D process, listed in Table 4, were flipped ("Early" to "Late" and "Late" to "Early"). This resulted in a new set of class labels, which were again randomized to training and test groups 250 times, stratified by line of therapy and PS. The whole procedure of creating mCs, filtering, combining to MCs, and assessing performance was repeated a third time. After the third repetition of the process, only 2 samples classified poorly when in the training set and it was decided that no further processing was required.

Figure 14F:
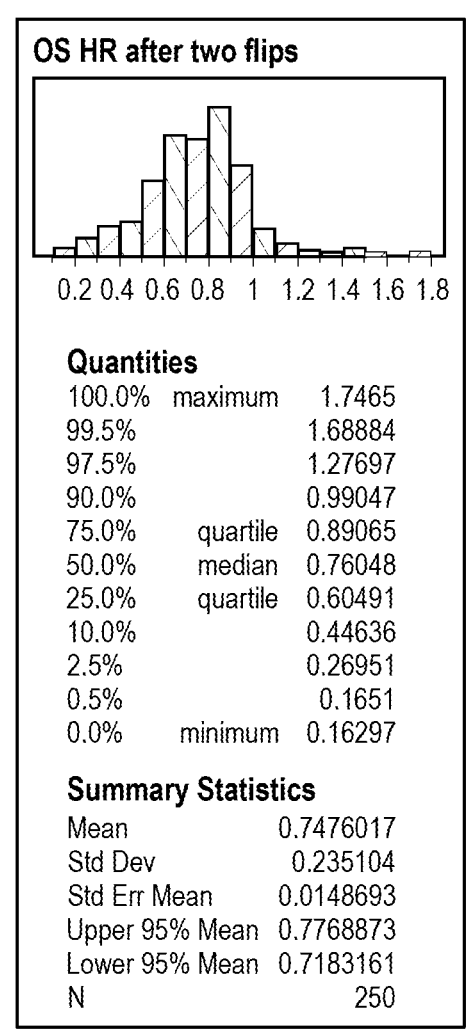

The distribution of MC performance for the 250 training/test splits of the third iteration of the CMC/D process is shown in FIGS. 14E-14F. More than 90% of the training/test split realizations yielded HRs between Early and Late classifications of the test sets that were less than 1, and more than half of the realizations had HRs less than 0.76 for PFS and less than 0.78 for OS. Instead of selecting one of these individual training/test splits for a final test/CMC/D classifier, the final classifier was defined as the majority vote of all 250 MCs for the third CMC/D iteration. This has the advantage of not requiring selection of a master classifier from a particular training/test set spit with the possibility of a particularly beneficial test or training set, and also removing any element of human subjectivity in making a choice and potentially providing a more robust final classifier. The class labels for the final test are defined through this process.

Adjustments to Take Account of Restrictions on Machine Qualification and Spectral Reproducibility The implementation of the final classifier described above to generate a class label for a sample under test implements certain adjustments in the mass spectral data processing to take into account some restrictions on machine qualification and spectral reproducibility that were present when the test was being developed. These adjustments are described in this section. This procedure is also described later on in conjunction with FIG. 12. It will be apparent to persons skilled in that art that these adjustments may not be necessary to generate a CMC/D classifier or implement a predictive test using a CMC/D classifier. The adjustments described in this section arose out of certain limitations of the mass spectrometer we used to generate mass spectra, and also out of the desire to increase the stability of the test.

A. Correction of Variations in m/Z Sensitivity of Mass Spectrometer

Spectra were acquired using Bruker mass spectrometer machines qualified previously to perform the original VeriStrat testing, using procedures described in J. Roder et al., U.S. Pat. No. 8,467,988. While the original VeriStrat test only uses features between 5 kDa and 13 kDa, the test described in this section uses features with higher and lower m/Z positions, in addition to features in this range. Spectrometers qualified for the original VeriStrat test must have adequate reproducibility of the mass spectral features used for the original test, but there are no requirements on m/Z sensitivity outside of this range.

Comparison of reference spectra generated from a reference sample at the same time as the spectra used in the present test development were generated with spectra generated from the same reference sample at a later time, both on previously qualified machines, indicated that, while m/Z sensitivity was similar for features within the 5 kDa to 13 kDa feature range, outside of this range the m/Z sensitivity showed some systematic differences.

To be able to compare spectra generated at different times or on different machines in a qualified setting at a level useful for testing in accordance with this new test, the feature values need to be corrected for these differences in m/Z sensitivity. This can be done using the reference spectra generated from a single reference sample that have been generated in the same batch as spectra used for present test development and subsequent batches of spectra from patient samples to be classified using the new VS 2.0 test. In this example (as shown in FIG. 12 at 1202A and 1202B), the reference samples were serum samples from a healthy human.

Two preparations of a reference sample were run in triplicate with the spectra used for VS2.0 development. These triplicates were averaged using the averaging workflow and pre-processed using the pre-processing workflow (see discussion of FIG. 12, infra). Feature values were generated and the feature values compared between the two preparations. In order to avoid using outlier feature values from one or the other preparation, features were pared down to those for which the feature vales were within 10% of each other for the two preparations. If FV1 is the feature value for a particular feature for preparation 1 of the reference sample (1202A, FIG. 12) and FV2 is the feature value for the same feature for preparation 2 of the reference sample (1202B, FIG. 12), the feature was considered suitable for analysis of relative m/Z sensitivity if:

$$|1-(FV1/FV2)|<0.1 \text{ or } |1-(FV2/FV1)|<0.1. \qquad \text{Eq. 2}$$

The feature values for these features are to be compared with the feature values for the same features generated from preparations of the reference sample in a subsequent batch of samples for VS2.0 testing. If two preparations are available in the subsequent batch, ideally run before and after the samples to be VS2.0 tested, the threshold of Eq. 2 should be met also for the features that can be used for m/Z sensitivity comparison within the second batch. If more than 2 preparations of reference sample are available, Eq.2 can be generalized to use the information available from the increased number of spectra so that the standard deviation of the feature values can be compared with the average feature value for each feature and features can be used for which the ratio of the standard deviation to the average are below a set threshold, such as 0.1.

Once a subset of the features are identified of suitable reproducibility, the variation in the m/Z sensitivity from the VS2.0 development batch of samples to any subsequent batch of samples can be examined in a plot of the ratio of the average feature values of the reference spectra in the development batch (AVO) to the average feature values of the reference spectra in the subsequent batch (AVN) as a function of m/Z. Such a plot is illustrated in FIG. 15.

Figure 15:
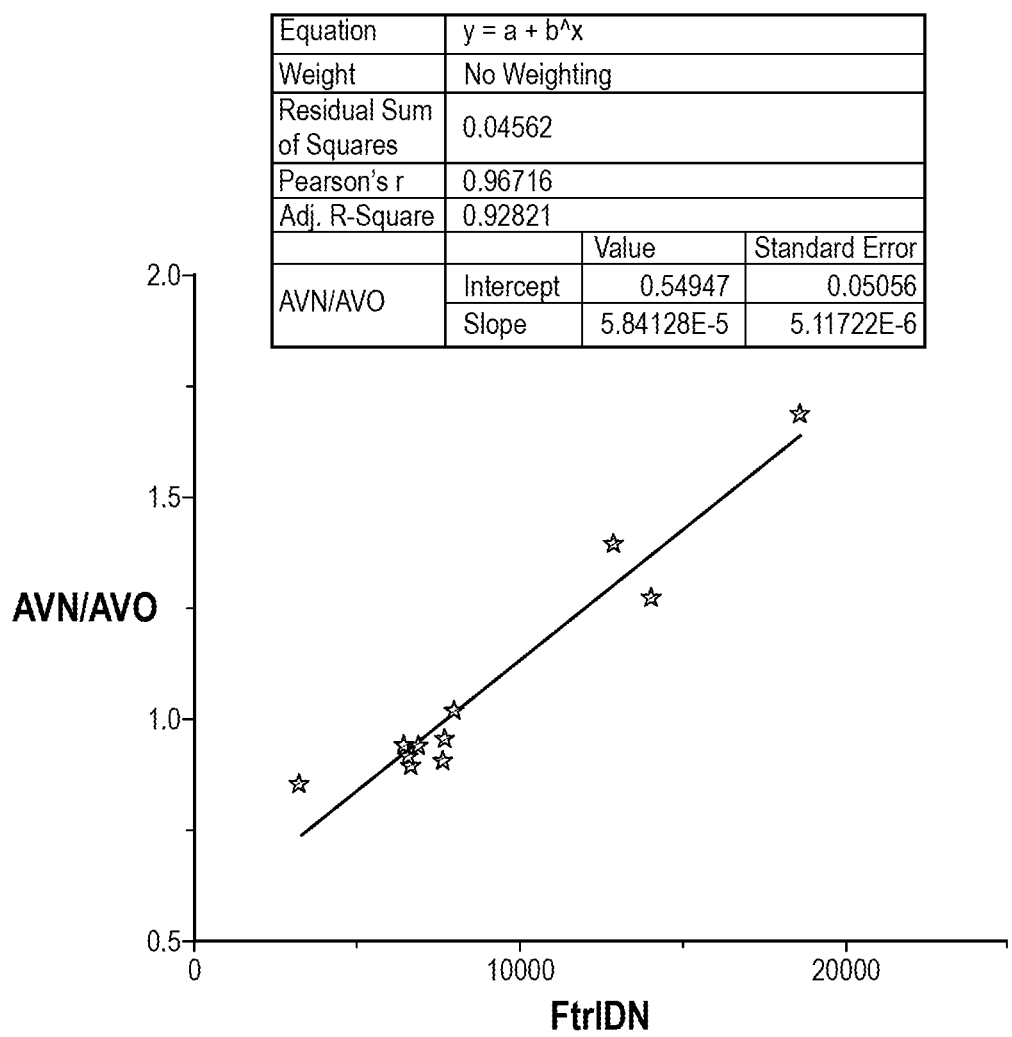
FIG. 15 is a plot of feature value ratio between the development set and a subsequent back of spectra for features passing the concordance criterion of Equation 1 obtained from the same reference sample.

A systematic variation in m/Z sensitivity can be seen in FIG. 15, with the development batch having lower sensitivity at higher m/Z and higher sensitivity at lower m/Z than the subsequent batch. To allow for a correction for this systematic difference in m/Z sensitivity, a straight line was fitted to the data in FIG. 15 and the slope and intercept determined. This gives a function with which each feature value obtained for any sample in the subsequent batch can be corrected to make it comparable with the feature values obtained for samples in the VS2.0 development batch.

B. Analysis of Stability of VS2.0 Classifications to Noise Inherent in the Acquisition of Mass Spectral from Serum Samples Via the VS1.0 Sample Handling and Spectral Acquisition Process VS1.0 is a highly reproducible test, with reproducibility of classifications in excess of 95%. One method of gaining reproducibility within the test is the use of the triplicate spotting of the sample for spectral generation and comparison of the triplicate labels before generation of the VS1.0 classification. As the triplicate spectra from a sample are averaged for the VS2.0 test, the redundancy of VS1.0 is lost and this approach cannot be extended to VS2.0. However, a method of in-silico generation of multiple replicates for a given test sample has been developed which allows for a simulation of the effect of the sample- and MALDI-spot-dependent, non-systematic irreproducibility (noise) inherent in the process of VS1.0 sample preparation, spotting and spectral generation.

To characterize the noise for each feature two runs of the Italian A, B, and C sample sets performed on mass spectrometers newly qualified for VS1.0 were compared. For each VS2.0 feature the feature values for each sample were compared across the two runs. This produced a concordance plot for each VS2.0 feature. For each concordance plot, a linear regression was used to fit a straight line to the feature value data. To characterize the noise around this fit, the residuals of the linear regression were examined. The noise was assigned to be predominantly additive or predominantly multiplicative. For additive noise, the noise strength was defined to be the standard deviation of the residuals. For multiplicative noise, each residual was divided by the corresponding feature value and the standard deviation of this quantity was defined to be the noise strength. The noise types and noise strengths for the VS2.0 features estimated in this way are given in Example 3 Appendix D.

Having characterized the noise for each feature by its type and strength, $\sigma$, noisy realizations of each feature for each sample, with measured feature value, F, could be generated via:

$$\text{additive noise: } F_{noisy} = F + \sigma\epsilon \qquad \text{Eq. (3)}$$

$$\text{multiplicative noise: } F_{noisy} = F(1 + \sigma\epsilon) \qquad \text{Eq. (4)}$$

where $\epsilon$ is a Gaussian random number with zero mean and unit standard deviation.

To investigate the stability of the VS2.0 classification under noise for a particular test sample, 160 noisy realizations of the feature table for each sample were generated using Eq. (3), Eq. (4) and the noise parameters for each filter given in Example 3 Appendix D. Each noisy realization was classified using the 250 MCs generated during the final iteration of the CMC/D process outlined above. This produced 250 classifications of "Early" or "Late" for each noisy realization of the sample, i.e. 40,000 "Early" or "Late" classifications per sample. Let the total number of "Early" classifications across the 250 master classifiers be $N_{Early}^i$ and the total number of "Late" classifications across the 250 master classifiers be $N_{Late}^i$, where $1 \leq i \leq 160$. By definition, $0 \leq N_{Early}^i \leq 250$, $0 \leq N_{Late}^i \leq 250$, and $N_{Early}^i + N_{Late}^i = 250$, for all i.

A noise effect estimator was defined as:

$$\text{Noise Effect Estimator} = \text{standard deviation of } N_{Early}^i / \qquad \text{Eq.(5)}$$

$$\left(\left|\sum_i N_{Early}^i - \sum_i N_{Late}^i\right| / 320\right)$$

$$= \text{sqrt}\left(\sum_i (N_{Early}^i)^2 - \left(\sum_i N_{Early}^i\right)^2\right) /$$

$$\left(\left|\sum_i N_{Early}^i - \sum_i N_{Late}^i\right| / 320\right)$$

$$= \text{sqrt}\left(\sum_i (N_{Early}^i{}^2) - \left(\sum_i N_{Early}^i\right)^2\right) /$$

$$\left(\left|\sum_i N_{Early}^i - 20000\right| / 160\right)$$

This "noise effect estimator" compares the variability in the number of "Early" master classifier classifications with the difference in the total numbers of "Early" and "Late" master classifier classifications. If the noise realizations produce a low variability in the number of "Early" classifications compared with the typical difference between the number of "Early" and "Late" master classifications for a realization, the noise effect estimator will be small. If the noise realizations produce a variability in the number of "Early" classifications large compared with the typical difference between the number of "Early" and "Late" master classifications for a realization, the noise effect estimator will be large.

Samples for which the difference in number of "Early" and "Late" master classifier classifications is large can tolerate substantial variability before producing a change in returned VS2.0 classification, whereas samples for which this difference is small are subject to changes in returned overall classification with only small variability. Hence, the noise effect estimator defined in Eq.5 provides a measure of how susceptible a sample is to classification label change.

Applying this procedure to two runs of the Italian A, B, and C sample sets to calculate the noise effect estimator for each sample revealed reliable classifications could be returned for samples by returning the VS2.0 classifier classification only for samples with a noise effect estimator below a threshold of 0.5. Above this threshold there is substantial uncertainty in returning a classification label for a sample under test and an Intermediate/Unknown classification label should be reported.

Application of the Final Classifier to Samples in the Development Set

Figure 16A:
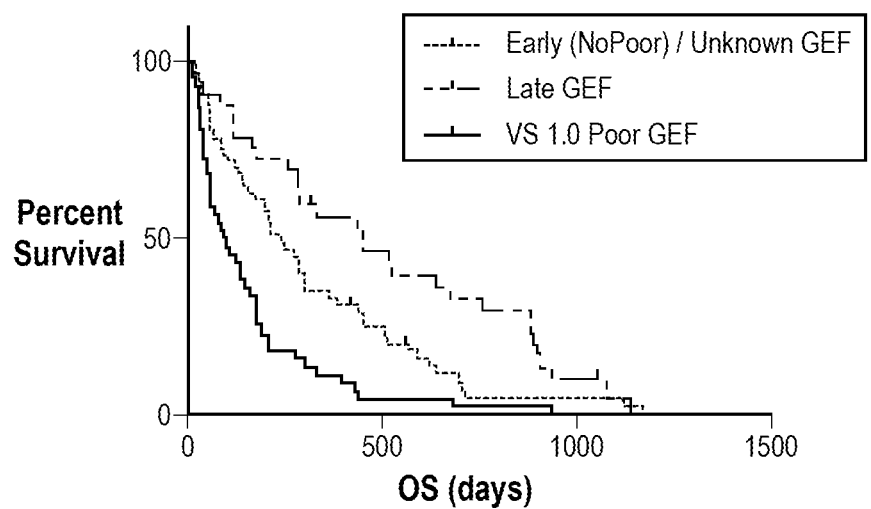
FIGS. 16A-16D are Kaplan-Meier curves showing the time-to-event outcomes of patients in the NSCLC/EGFR-I CMC/D classifier development set with labels assigned from development set spectra.
Figure 16B:
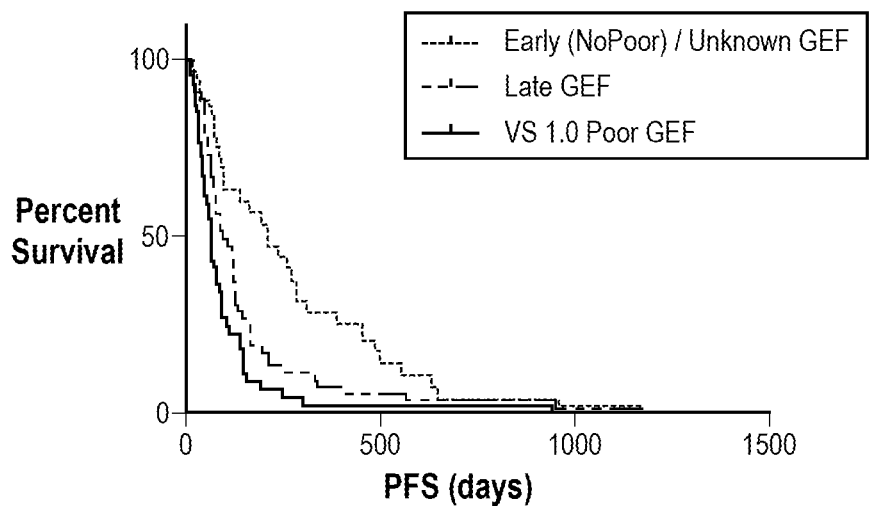
Figure 16C:
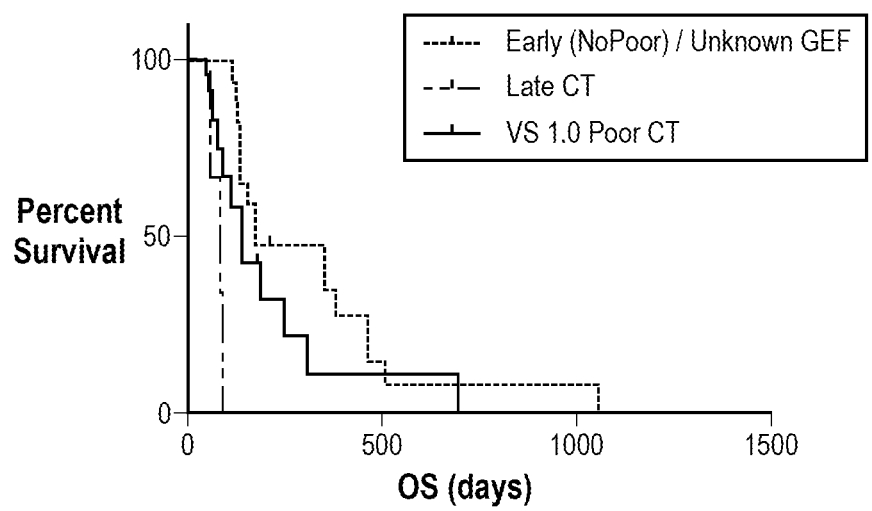
Figure 16D:
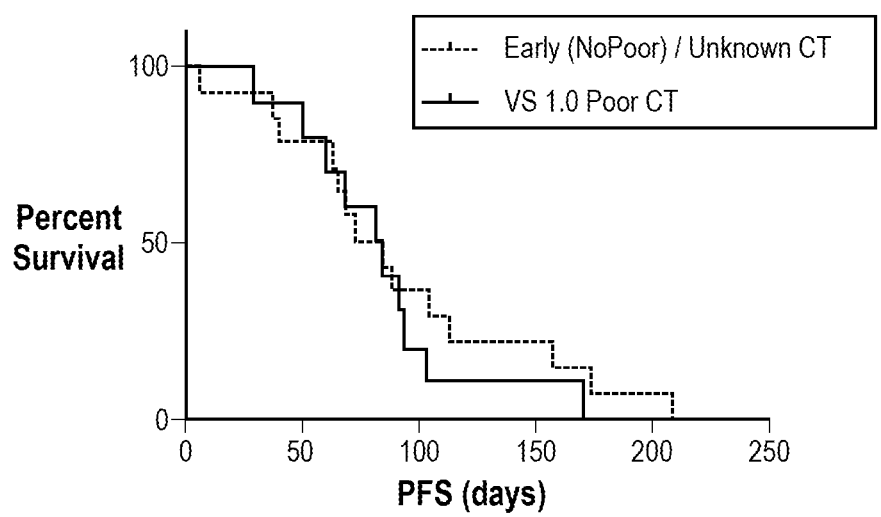

The VS2.0 final classifier was applied to all samples in the development sample set. Note that this includes samples included in training of the classifier. The VS2.0 classifications of the development set samples are given in Example 3 Appendix E. Notice that all samples with a VS1.0 classification of Poor were assigned a label of Early. OS and PFS are plotted for patients in the development set grouped according to: Late, Unknown and Early (excluding VS1.0 Poor) and VS 1.0 Poor in FIG. 16. Note that several patients in the Italian C cohort had OS data, but no PFS data. FIG. 16 is a plot of time-to-event outcomes of patients in the development set with labels assigned from development set spectra; FIG. 16A: OS for gefitinib-treated patients, FIG. 16B: PFS for gefitinib-treated patients, FIG. 16C: OS for chemotherapy-treated patients and FIG. 16D PFS for chemotherapy-treated patients. By comparing FIGS. 16A and 16C, it is noted that those patients whose sample tested Late obtained greater benefit from gefitininb than chemotherapy, as indicated by the overall survival curves for these patients. Survival statistics related to the plots in FIG. 16 are presented in Tables 5 and 6

TABLE 5

Medians associated with FIG. 16

| Endpoint | Group | n | Median (days) | 95% CI (days) |
|---|---|---|---|---|
| OS | Late GEF | 32 | 457 | 259-680 |
| OS | Early/Unknown GEF | 53 | 243 | 144-304 |
| OS | VS1.0 Poor GEF | 44 | 96.5 | 60-162 |
| PFS | Late GEF | 32 | 208 | 90-287 |
| PFS | Early/Unknown GEF | 53 | 92 | 69-122 |
| PFS | VS1.0 Poor GEF | 44 | 61.5 | 43-83 |
| OS | Late CT | 3 | 80 | 55-92 |
| OS | Early/Unknown CT | 17 | 172 | 132-383 |
| OS | VS1.0 Poor CT | 12 | 141 | 60-250 |
| PFS | Early/Unknown CT | 14 | 78.5 | 40-113 |
| PFS | VS1.0 Poor CT | 10 | 82.5 | 29-93 |

TABLE 6

Hazard Ratios and p values associated with FIG. 16

| Endpoint | Comparison | log-rank p | Cox HR (95% CI) | CPH p value |
|---|---|---|---|---|
| OS | GEF: Early/Unk vs Late | 0.025 | 0.59 (0.37-0.94) | 0.027 |
| OS | GEF: Poor vs Late | <0.001 | 0.30 (0.18-0.49) | <0.001 |
| OS | GEF: Poor vs Early/Unk | <0.001 | 0.49 (0.33-0.75) | <0.001 |
| PFS | GEF: Early/Unk vs Late | 0.018 | 0.58 (0.37-0.91) | 0.018 |
| PFS | GEF: Poor vs Late | <0.001 | 0.36 (0.22-0.60) | <0.001 |
| PFS | GEF: Poor vs Early/Unk | 0.025 | 0.64 (0.42-0.95) | 0.029 |
| OS | CT: Poor vs Early/Unk | 0.217 | 0.61 (0.28-1.35) | 0.221 |
| PFS | CT: Poor vs Early/Unk | 0.477 | 0.74 (0.31-1.72) | 0.479 |

Samples from Italian A, B and C were rerun twice. (In the last run only the VS1.0 Good samples were rerun and a few samples were omitted due to lack of remaining sample volume.) The results across the three runs are summarized in Example 3 Appendix F.

The sensitivity corrections together with the in-silico noise analysis led to good reproducibility of actionable labels. Of the 93 samples run in the last run 16 were labeled Late, 35 were labeled Early, and 42 were labeled Unknown. The samples labeled as Late in the third run they were either labeled as Late or Unknown in the previous runs. The samples labeled as Early in the third run were either labeled as Early or as Unknown in the previous runs. 24 of the 35 samples labeled as Early in the third run were labeled as Early in all three runs. 14 of the 16 samples labeled as Late in the third run were labeled as Late in all three runs. 20 of the 42 samples labeled as Unknown in the third run were labeled as unknown in all three runs. While the large proportion of Unknowns is undesirable, it does appear that if we call a label of Early (Late) from a VS2.0 analysis, this sample would be characterized as Early (Late) in another run, or be called Unknown.

Application of the Final CMC/D Classifier to Samples from the PROSE Study

Testing Procedure: Blinding

The final CMC/D classifier described above was subject to a test on mass spectra obtained from available samples from the PROSE study under a validation protocol. Mass spectra were provided to analysts blinded to their clinical data. The spectra were analyzed as described above and the resulting classifications (Example 3 Appendix G) were generated. An un-blinding key was then provided and a statistical analysis was carried out.

Testing Procedure: m/Z Sensitivity Correction Calculation

Figure 17:
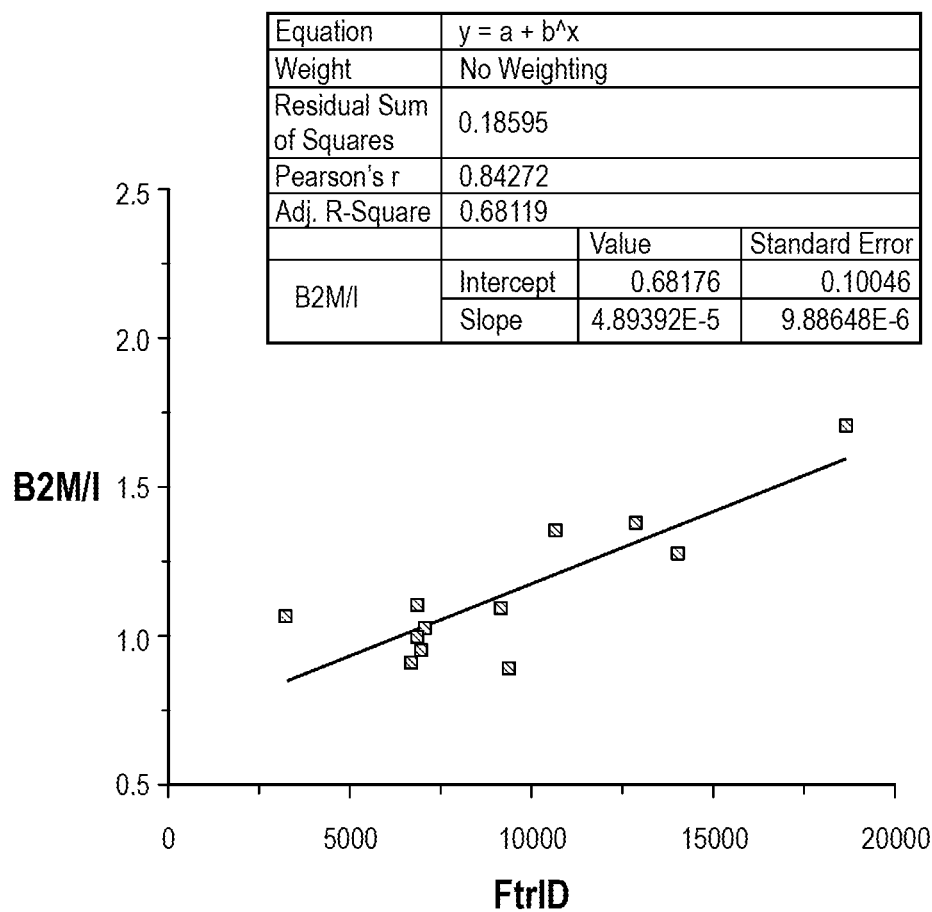
FIG. 17 is a plot of the regression curve for sensitivity correction for the NSCLC/EGFR-I CMC/D classifier applied to the PROSE sample set.

The serum P2 (reference) spectra generated together with the PROSE spectra were analyzed to provide the necessary m/z sensitivity correction. As the PROSE samples spanned 5 batches, one preparation of serum P2 was collected with each batch. With 5 separate preparations, the CV calculation approach (outlined above) was used. The regression curve for PROSE data is shown in FIG. 17. From this curve, Y axis intercept and slope values were obtained as indicated in the inset to FIG. 17.

Statistical Analysis of Results

The VS2.0 classifications obtained for the samples from the PROSE trial are listed in Example 3 Appendix G. Only samples from patients in the PROSE primary analysis population were considered for statistical analysis. For patient 01_044 and patient 01_080, two samples were available. The results for the sample with the standard labeling, rather than the sample labeled as 'second_sample', were used for the statistical analysis. Two samples were also available for patient 06_010, but both had VS2.0 classification of Early. No samples were Available for patient 01_050, patient 03_006, patient 06_004, patient 06_021, patient 11_043, patient 11_048, and patient 12_014.

Hence samples were available from 256 of the 263 patients in the PROSE per-protocol population: 148 were classified as Early, 39 as Late, and 69 as Unknown. All of the samples classified as Late were associated with patients with VS1.0 Good classification. Only two of the patients classified in the PROSE primary analysis as VS1.0 Poor were classified as Unknown; all others were classified as Early. Of the 148 patients classified as Early, 73 had VS1.0 classification of VS Good and 75 had VS1.0 classification of VS Poor.

Patient characteristics by VS2.0 classification are shown in Table 7.

TABLE 7

Patient characteristics by VS2.0 classification within VS1.0 Good population

| | | Late (N = 39) | Early/Unknown (N = 140) | p value |
|---|---|---|---|---|
| Histology | Adeno | 27 (69%) | 93 (67%) | 0.100 |
| | Squamous | 2 (5%) | 24 (17%) | |
| | BAC | 2 (5%) | 1 (1%) | |
| | Large | 2 (5%) | 8 (6%) | |
| | NOS | 2 (5%) | 4 (3%) | |
| | Other/Missing | 4 (10%) | 10 (7%) | |
| Gender | Male | 26 (67%) | 94 (67%) | >0.99 |
| | Female | 13 (33%) | 46 (33%) | |
| Smoking Status | Never | 7 (18%) | 23 (16%) | 0.968 |
| | Former | 23 (59%) | 82 (58%) | |
| | Current | 9 (23%) | 35 (25%) | |
| PS | 0 | 24 (62%) | 81 (58%) | 0.491 |
| | 1 | 15 (38%) | 52 (37%) | |
| | 2 | 0 (0%) | 7 (5%) | |
| EGFR mutation | Mutation | 5 (16%) | 7 (7%) | 0.159 |
| | WT | 24 (75%) | 84 (86%) | |

Figure 18A:
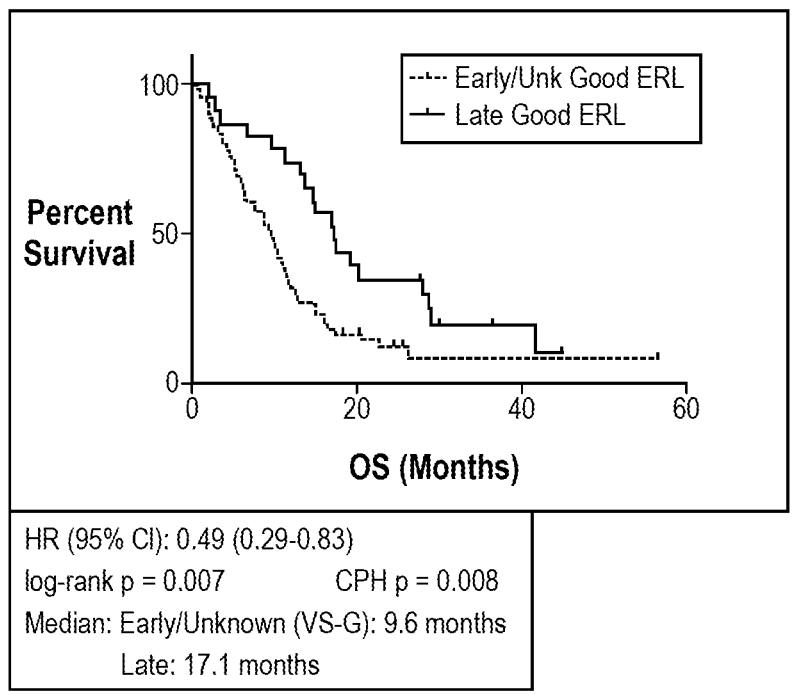
FIGS. 18A and 18B are Kaplan-Meier plots of overall survival for the groups Late and Early/Unknown (those patients testing VeriStrat Good in the original VeriStrat test) for patients treated with erlotinib (FIG. 18A) and chemotherapy (FIG. 18B).
Figure 18B:
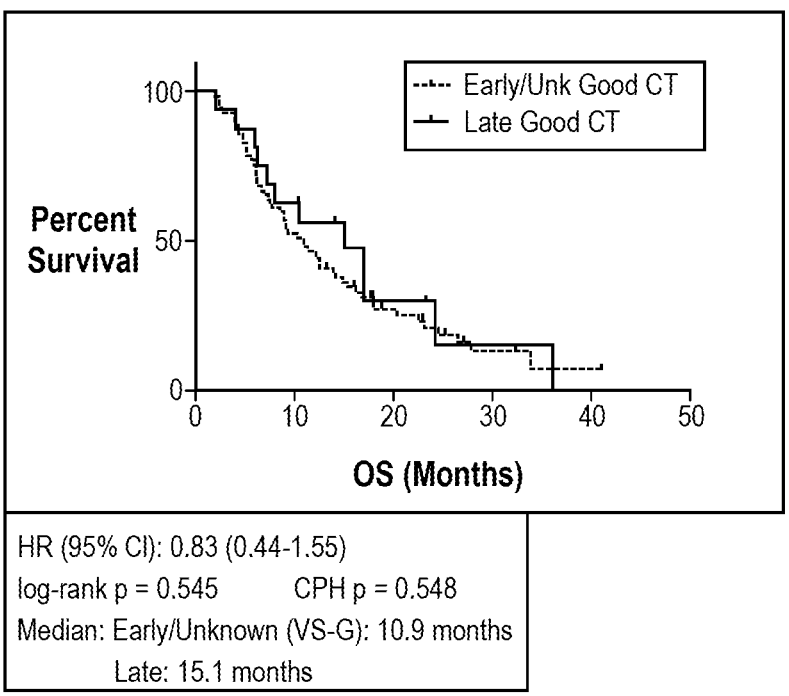
Figure 19A:
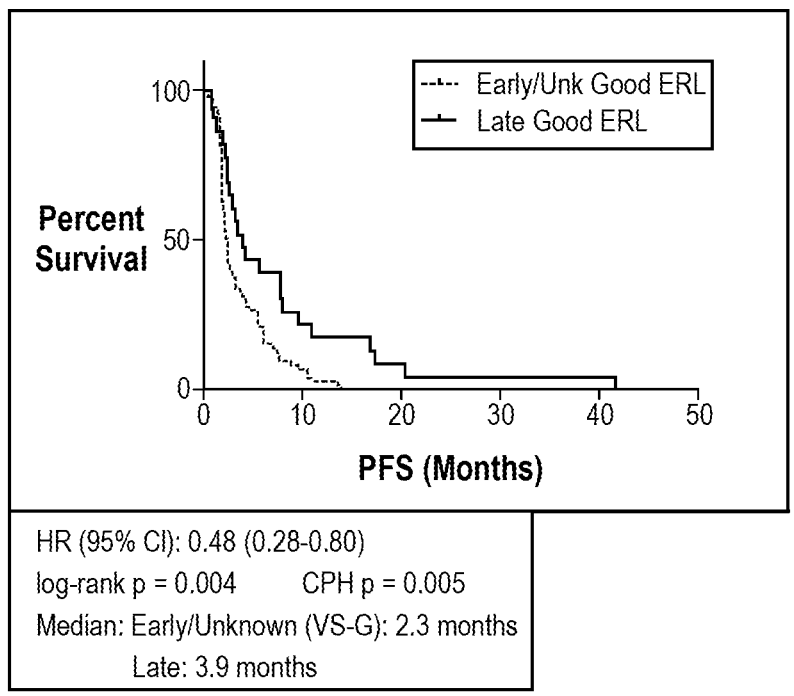
FIGS. 19A and 19B are Kaplan-Meier plots of progression-free survival for the groups Late and Early/Unknown (those patients testing VeriStrat Good in the original VeriStrat test) for patients treated with erlotinib (FIG. 19A) and chemotherapy (FIG. 19B).
Figure 19B:
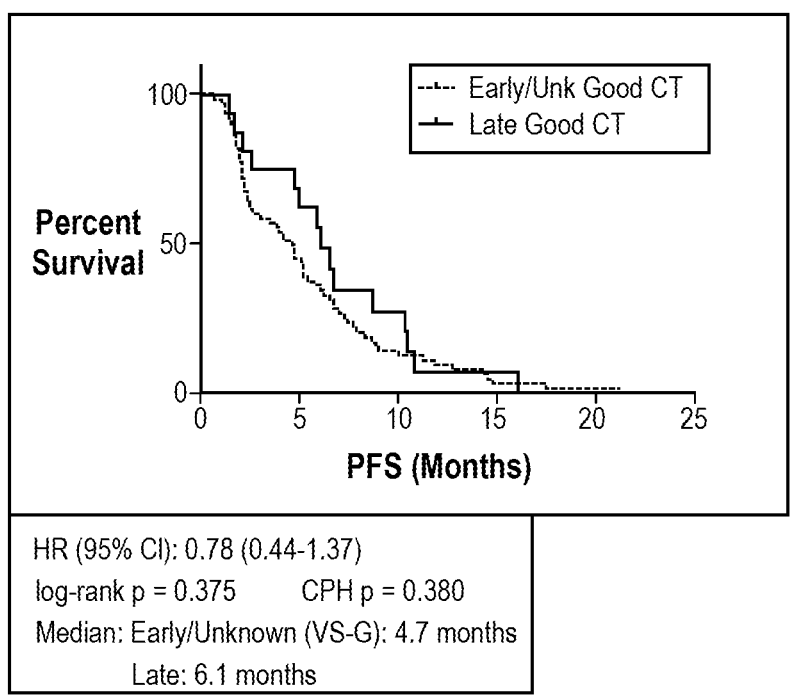

FIG. 18 shows the OS results for the classification groupings Late and Early/Unknown (VS1.0 Good) by treatment, with FIG. 18A showing the data for the erlotinib treatment group and FIG. 18B showing the data for the chemotherapy treatment group. FIG. 19 shows the PFS results for the classification groupings Late and Early/Unknown (VS1.0 Good) by treatment, with FIG. 19A showing the data for the erlotinib treatment group and FIG. 19B showing the data for chemotherapy treatment group.

The results of a multivariate analysis of the VS1.0 Good population are shown in Table 8. VS2.0 result of Late or Early/Unknown remains significant when adjusted for possible confounding factors.

TABLE 8

Multivariate analysis of VS1.0 Good population

| Endpoint | Covariate | HR (95% CI) | p value |
|---|---|---|---|
| OS | Treatment: CT vs ERL | 1.12 (0.85-1.65) | 0.320 |
|  | VS2.0: Early/Unknown vs Late | 0.59 (0.39-0.89) | 0.012 |
|  | Gender: Male vs Female | 0.83 (0.57-1.20) | 0.316 |
|  | PS: 0-1 vs 2 | 1.87 (0.86-4.08) | 0.114 |
|  | Smoking Status: Never vs Ever | 1.23 (0.75-2.00) | 0.411 |
| PFS | Treatment: CT vs ERL | 1.43 (1.05-1.93) | 0.023 |
|  | VS2.0: Early/Unknown vs Late | 0.57 (0.39-0.83) | 0.004 |
|  | Gender: Male vs Female | 1.06 (0.75-1.48) | 0.759 |
|  | PS: 0-1 vs 2 | 1.30 (0.60-2.81) | 0.500 |
|  | Smoking Status: Never vs Ever | 1.31 (0.85-2.02) | 0.230 |

Figure 20:
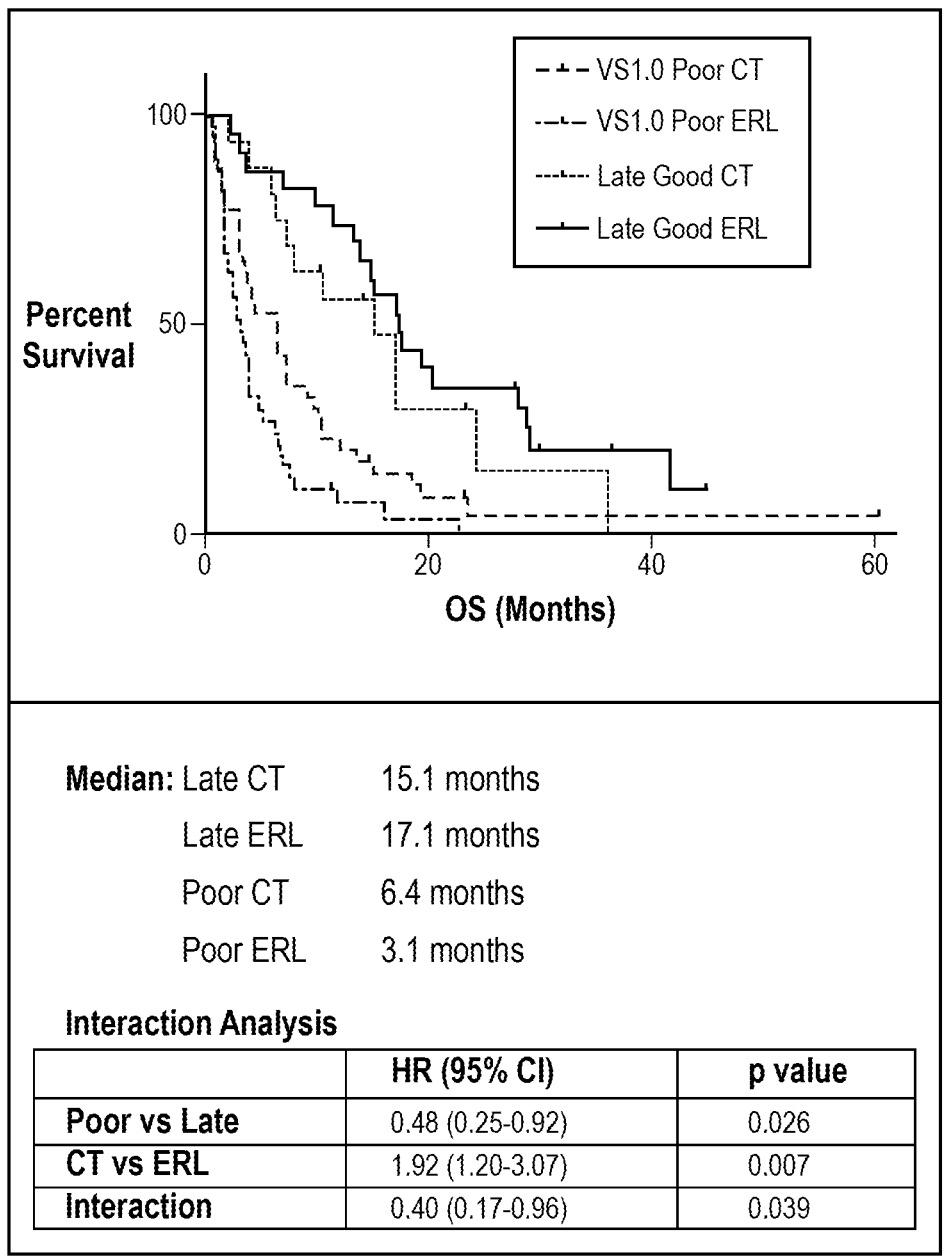
FIG. 20 is a Kaplan-Meier plot of overall survival for patients classified as VeriStrat Poor and Late by treatment for Example 3.

FIG. 20 shows the Kaplan-Meier plots of OS for the groups VS1.0 Poor and Late by treatment along with the results of the analysis of interaction between classification, VS1.0 Poor and Late, and treatment.

Figure 21:
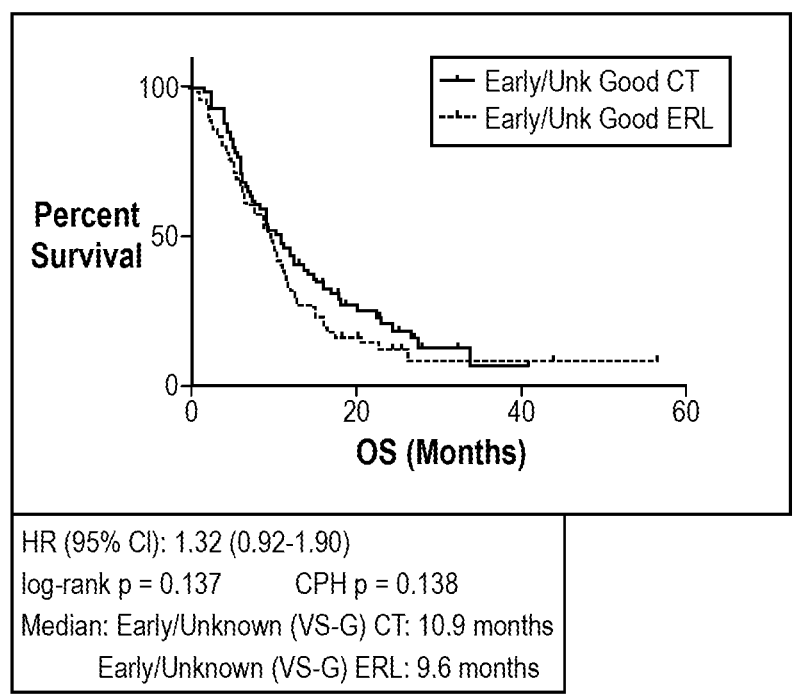
FIG. 21 is a Kaplan-Meier plot of OS within the VeriStrat Good Early/Unknown group by treatment for Example 3.

FIG. 21 compares outcomes between chemotherapy and erlotinib within the VS1.0 Good Early/Unknown group.

Figure 22A:
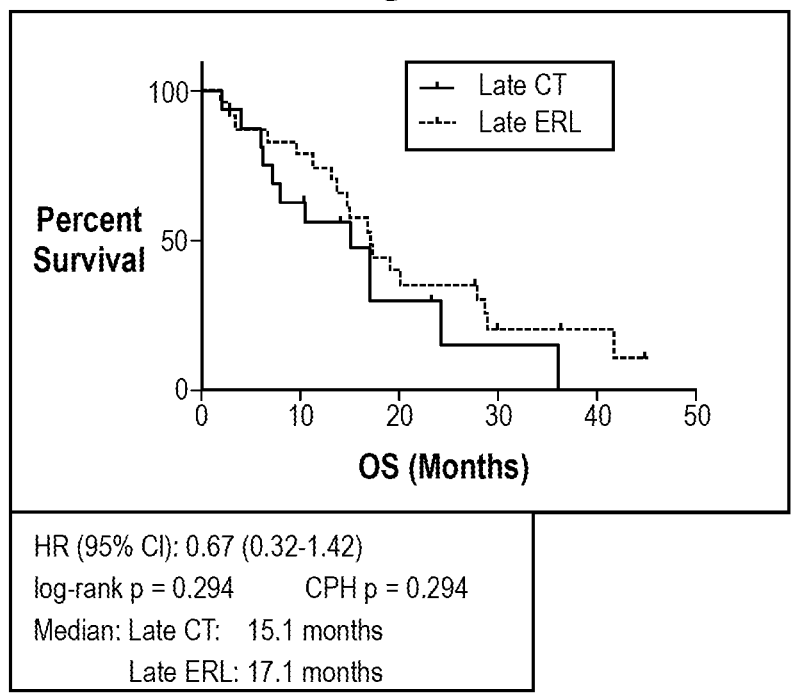
FIG. 22A is a Kaplan-Meier plot of OS within the late group by treatment.
Figure 22B:
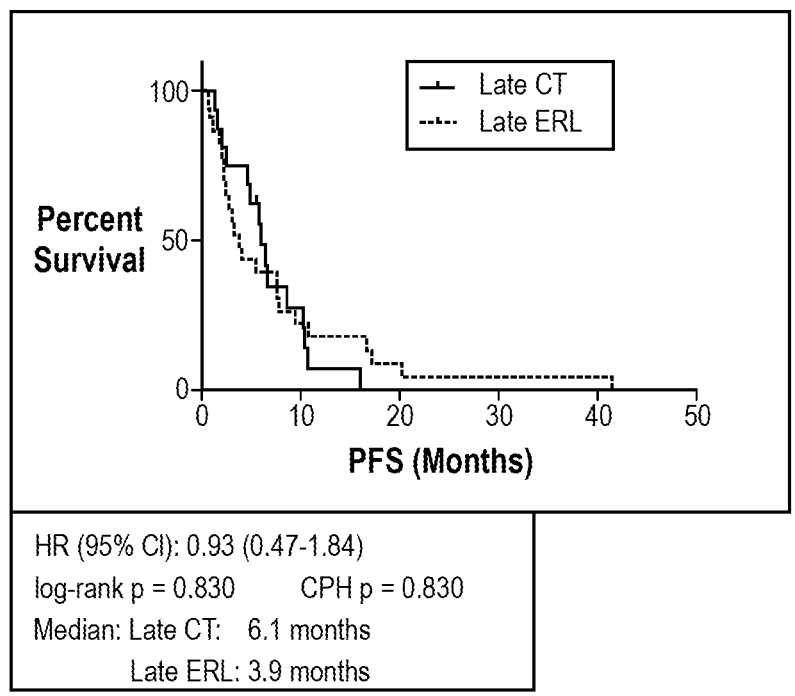
FIG. 22B is a Kaplan-Meier plot of PFS within the late group by treatment.

A comparison of outcomes within the Late group by treatment is shown in FIG. 22. Note that in FIG. 22A, those patients classified as Late and receiving erlotinib had a median overall survival time of 17.1 months, two months greater than those patients receiving chemotherapy.

The medians for OS and PFS for each group are summarized for each treatment arm, along with their 95% confidence interval and the number of patients in each group in Table 8.

TABLE 8

Medians for OS and PFS by group and treatment arm

| Endpoint | Group | n | Median (months) | 95% CI (months) |
|---|---|---|---|---|
| OS | Late CT | 16 | 15.1 | 6.2-24.2 |
| OS | VS1.0 Poor CT | 40 | 6.4 | 3.3-7.4 |
| OS | Early/Unknown (VS1.0 Good) CT | 69 | 10.9 | 7.4-14.1 |
| OS | Late ERL | 23 | 17.1 | 13.1-27.9 |
| OS | VS1.0 Poor ERL | 37 | 3.1 | 2.0-4.0 |
| OS | Early/Unknown (VS1.0 Good) ERL | 71 | 9.6 | 6.3-11.0 |
| PFS | Late CT | 16 | 6.1 | 2.6-10.4 |
| PFS | VS1.0 Poor CT | 40 | 2.8 | 1.9-4.5 |
| PFS | Early/Unknown (VS1.0 Good) CT | 69 | 4.7 | 2.5-5.4 |
| PFS | Late ERL | 23 | 3.9 | 2.4-7.8 |
| PFS | VS1.0 Poor ERL | 37 | 1.7 | 1.5-2.2 |
| PFS | Early/Unknown (VS1.0 Good) ERL | 71 | 2.3 | 2.0-2.8 |

Example 3

Conclusions

The test described in this section (VS 2.0) is a truly multivariate test utilizing 74 features derived from a mass spectrum of a blood-based sample to identify a group of 2nd line NSCLC patients having superior performance on erlotinib over chemotherapy. The development of this test has validated the CMC/D classifier development methodology. VS2.0 separates the group we previously identified as "Good" in the original VeriStrat test group into two sub-groups, "VS2.0 Early" or "Early" and "VS2.0 Late" or "Late", albeit with a substantial group of unidentifiable patients, described here as "VS2.0 Unknowns", due to limitations of spectral acquisition.

In its current implementation, this test (VS2.0) relies on spectral acquisitions on machines qualified for our original VeriStrat test. As VS2.0 requires feature values from m/z ranges outside of the VS1.0 validation regime, special care needs to be taken to correct for differences in m/z dependent sensitivity by utilizing reference samples. Label stability is assessed using in-silico sensitivity analysis, which leads to a substantial numbers of VS2.0 Unknowns. The reproducibility of assigned VS2.0 labels in terms of assigning only sure labels has been assessed by three runs of the development set, and is very high. For clinical use of VS2.0 we analyzed three groups: VS2.0 Late, VS2.0 Early and Unknowns in the VS1.0 good population, and VS1.0 Poors which classify almost uniformly as VS2.0 Early.

VS2.0 was qualified (clinically validated) in a blinded analysis of the PROSE samples. The available number of samples in the VS2.0 Late group limited the significance of this qualification in some aspects. Comparing overall survival in VS2.0 Lates to VS2.0 Early/unknowns in the VS1.0 Good group shows that VS2.0 splits the VS1.0 good group into a well and poor performing group under erlotinib treatment, while there is little evidence for such a split in the chemotherapy arm. Unfortunately the sample size was too small to achieve statistical significance for a superiority of erlotinib over chemotherapy. VS2.0 retains the predictive power of VS1.0 (VS2.0 Late vs. VS1.0 Poor by treatment) even though the sample size was halved. The results on PFS are similar than in OS.

The successful development of VS2.0 validates the correlational approach to test development, and the CMC/D methodology in general. The parallel iterative development of training labels and a test to identify such patients has worked surprisingly well. The measures inherent in CMC/D to avoid overfitting have been proven valid, and been extended to include majority votes over training/test split MCs further reducing ambiguity in test/final classifier selection. VS2.0 utilizes around 60% of observable peaks in the summed spectra we used (3 replicates of a 2,000 shot spectrum) with no clear favorite features. Hence, while the present example makes use of the particular features noted in Example 3 Appendix B, these specific features are not believed to be essential or critical and well performing tests could be based on a subset of these features or possibly additional features, e.g., discovered by spectra obtained from a greater number of shots.

In terms of commercial use VS2.0 provides a tool to identify a group of patients for which one can be reasonably certain that erlotinib is at least equivalent to chemotherapy, and likely to be superior. Medians of 17 months overall survival in a second line setting are spectacular, and might lead to changes in treatment regime in 2nd line NSCLC. Again, we were able to define the class labels "Early" and "Late" (or the equivalent) that enable this prediction as a part of this process.

Use of VS 2.0 CMC/D Classifier in a Testing Environment (FIG. 12)

The application of the CMC/D classifier as described in Example 3 to classify a blood-based sample from a NSCLC patient will be described in this section in conjunction with FIG. 12. As explained above, if the class label assigned to the test sample is "Late" or the equivalent, the class label predicts that the NSCLC patient providing the sample is more likely to benefit from an EGFR-I such as erlotinib or gefitinib as compared to chemotherapy. A class label of Poor or the equivalent indicates that the patient is not likely to be benefit from an EGFR-I in treatment of the cancer. A class label of Intermediate/Unknown indicates that the patient is likely to obtain benefit that is similar in clinically meaningful terms from chemotherapy or an EGFR-I.

The workflow showing use of the CMC/D classifier generated in accordance with FIG. 11 on a mass spectrum of a test sample is shown in FIG. 12. The process begins with providing three blood-based samples to a mass spectrometer: a test sample 1200 from a patient for whom the test is being performed, and two reference samples shown as Reference Sample 1 and Reference Sample 2, items 1202A and 1202B, respectively. These two reference samples are two aliquots from the reference blood-based sample from a healthy human patient. The reference samples 1202A and 1202B are used in this embodiment in order to correct for m/z sensitivity variations over m/z ranges that are outside of previously qualified m/z ranges for the particular mass spectrometer that was used in the VS 1.0 test. It is possible that with appropriately qualified machines the use of reference samples 1 and 2 may not be necessary.

At step 1204, mass spectrometry on the three samples 1200, 1202A and 1202B is performed using a MALDI-ToF mass spectrometer. Each sample is subject to 2000 shot "dilute and shoot" MALDI-ToF mass spectrometry in the instrument three times with spectral acquisition filtering (see the above discussion). The resulting three 2000 acquired shot spectra for each of the three samples are transferred from the mass spectrometer to machine-readable memory of a general purpose computer implementing the workflow of FIG. 12.

Figure 23:
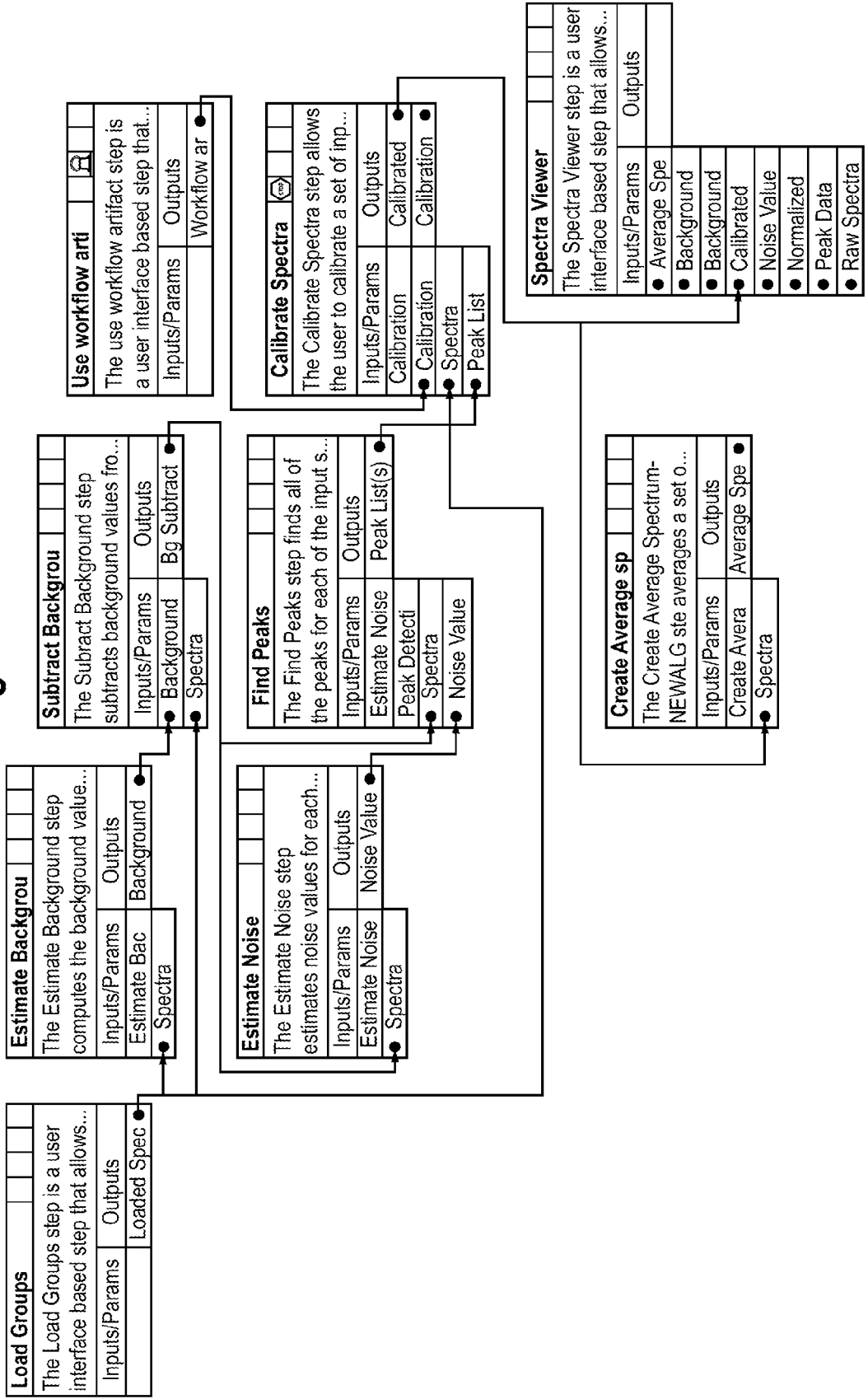
FIG. 23 is an illustration of the averaging workflow module 1206 of FIG. 12.

A software module Averaging Workflow 1206 is then invoked to perform an averaging of the triplicate spectra obtained at step 1204, indicated at step 1208. The averaging workflow is shown in FIG. 23. Basically, this module estimates peaks in the spectra that are used for alignment, performs an alignment of the raw spectra, and then computes the average values of the aligned spectra from the three replicates from each of the three samples.

Figure 24:
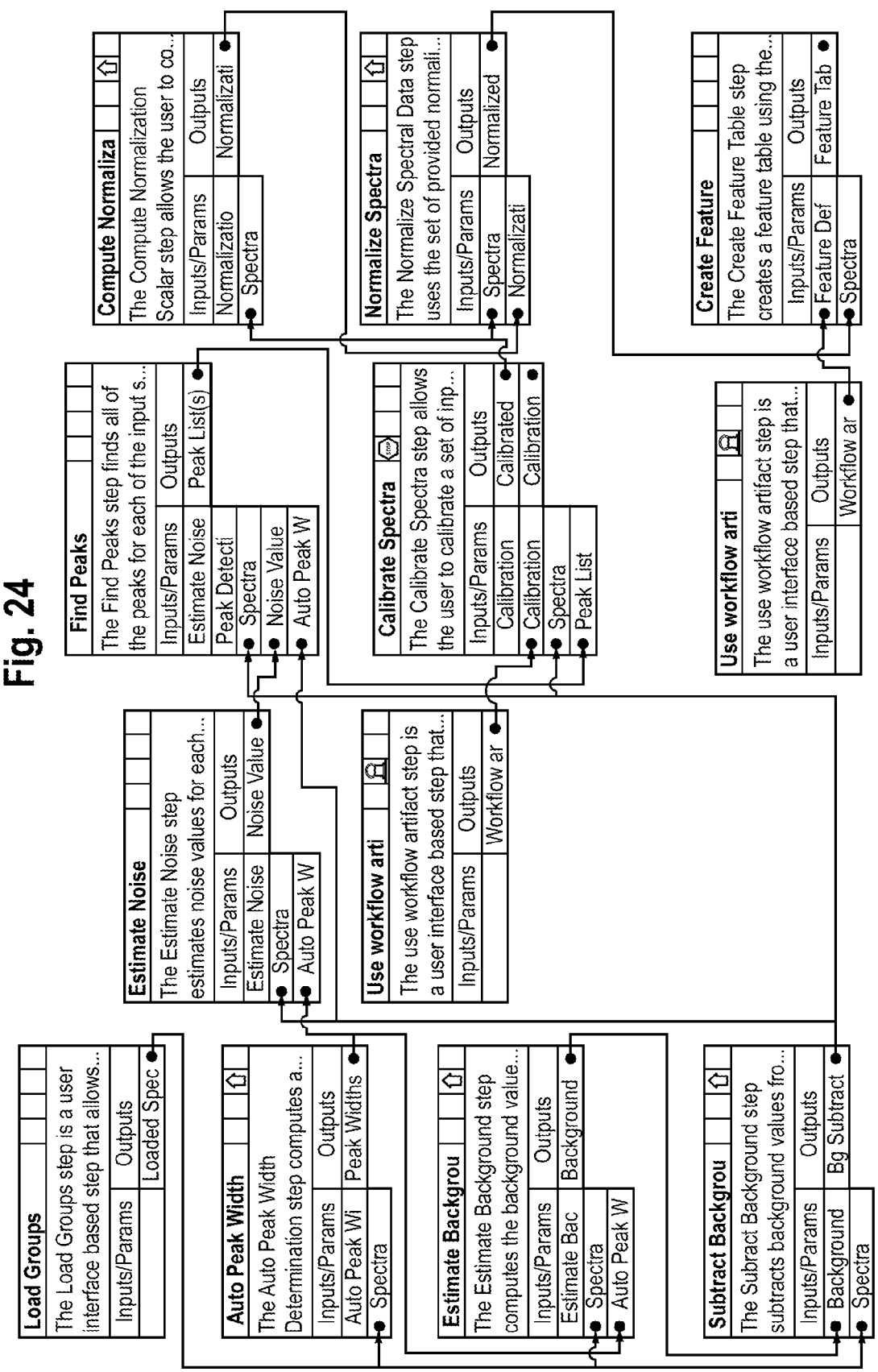
FIG. 24 is an illustration of the pre-processing workflow module 1212 of FIG. 12.

A Pre-processing Workflow module 1212 (FIG. 24) is then invoked to perform pre-processing of the averaged spectra and to generate feature values (a feature table) for use in classification as indicated at step 1214. The step includes background subtraction and estimation, peak detection and alignment, partial ion current normalization, and calculation of feature values (integrated intensity values) over pre-defined m/Z ranges. The ranges are listed in Example 3 Appendix B.

As indicated at 1216, the feature values for the two reference samples (1202A and 1202B) generated at step 1214 are provided to a module 1218 which checks to see if the reference values are concordant. Basically, in module 1218, a comparison of the reference feature values are performed. This involves the following:
1. Calculate parameter $\delta_F$=min (|1−(FVpre/FVpost)|, |1−(FVpre/FVpost)|) for all feature values F obtained at step 1214. The idea here is to run one reference sample (1202A) before the test sample 1200 (or at the beginning of a batch of test samples), and obtain the set of feature values from the reference sample i.e. $FV_{Pre}$, and then run another preparation of the reference sample 1202B after the test sample 1202 (or at the end of the batch of test samples), and obtain the set of feature values from the reference sample again i.e. $FV_{Post}$.
2. Select those features where $\delta_F$ is <0.1, Add those feature values to a list of feature values (list L).
3. Compare the list of features L selected at 2 with the list of feature values, L', obtained from the same steps 1-2 from the reference samples run with the development set of samples used to generate the CMC/D classifier (i.e., the list of features in Example 3 Appendix B.)
4. If list L contains the feature at m/Z positions 3219 and 18634, these feature values are considered concordant.

If the concordance test (4.) fails, the process goes back to the beginning and the spectra acquisition of the test sample and the two reference samples is redone. If the concordance test (4.) succeeds, the processing proceeds to the define feature correction function step 1222 using the standard set of feature values 1220. These are the feature values for the two preparations of the reference sample (1201A and 1202B) that were run with the development set samples when the original spectra were generated (i.e., at time of generation of the CMC/D classifier). It can be a list of all the feature values, but some do not pass the concordance criteria that we have set up between the two preparations, and so these features would never be used in practice and would be excluded from the list. We look for features that are consistent (concordant) between the two preparations of the reference sample run with the development set spectra and also concordant for the pre- and post-reference spectra. Then, we calculate the averages of the original samples and the averages of the pre- and post-samples for these features. We work out the ratio of these two and plot it as a function of m/Z. A linear regression of the graph of ratios is generated and the Y axis intercept and slope are returned. See the discussion of FIG. 15, supra.

At step 1224, the Y axis intercept and slope from step 1222 are feature value correction function parameters a and b, respectively, from the linear regression plot. These values are applied to the test sample feature values generated at step 1214. This correction can be expressed as follows:

$$FV_{Corrected} = FV_{estimated}/(a+bm_z)$$

At step 1224, these corrected feature values are stored in memory. The corrected feature values are used in two separate processing branches: steps 1228 and in step 1232.

In step 1228, the data set representing the final CMC/D classifier 1226 generated in accordance with the procedure of FIG. 11 is applied to the corrected test sample feature values. In this example, the final CMC/D classifiers is the set of 250 master classifiers generated in each of the test and training sample splits realizations from the classifier generation sample set 1100 (FIG. 11) and created at step 1134 of FIG. 11. The result of this application of the master classifier to the corrected feature values is a test sample classification label, as indicated at 1229.

As indicated in FIG. 12 at 1232, the corrected feature values generated at step 1224 are also sent to a module 1232 which generates new feature value realizations ("noise realizations") making use of pre-defined feature-dependent noise characteristics 1230. Basically, this module 1232 uses noise parameters a, obtained from the development sample set (FIG. 11, 1100) to generate 160 noise realizations:

Additive noise realizations:

$$FVN_i = FV_{corrected,i} + \epsilon_i$$

Multiplicative noise realizations:

$$FVN_i = FV_{corrected,i} * (1+\epsilon_i)$$

where $\epsilon_i$ is a Gaussian random number (N) with zero mean and unit standard deviation characterized by the expression N (0, $\sigma_i$) where $\sigma_i$ are noise parameters determined from the development set as described previously.

The resulting "noise" feature values generated in step 1232 are in the form of a feature table. All the feature values are provided as workflow artifacts. The results of this process are stored in convenient form, such as Excel spreadsheets.

Figure 25:
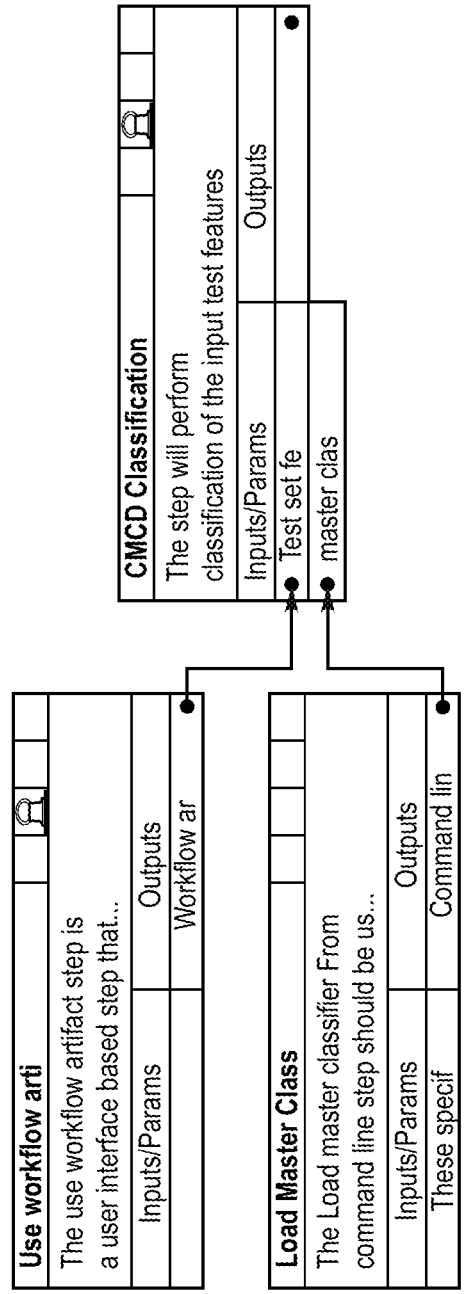
FIG. 25 is an illustration of the modules 1228 and 1234 of FIG. 12 that apply the master classifier to the corrected test sample feature values and the noisy feature value realizations.

At step 1234, the data set representing the master classifier (1226, described above) is applied to the noisy feature values generated in step 1232. See FIG. 25. This results in a table of master classifier results (# of class labels of each type). In this particular example, where the master classifier takes the form of 250 master classifiers resulting from 250 training/test set splits (as explained above), there are 250 class labels generated for each noise realization. The master classifier results for the noise realizations are collated as indicated at step 1236 so that statistical data on the classification results can be obtained as indicated as 1238. In this step 1236 we generate the ratio R (referred to as the "noise effect estimator") which is related to the standard deviation of the difference between the number of Late and Early classifications. This is done over all the noisy realizations of the feature table. The particulars of this statistical analysis and computation of ratio R is as follows:

let $N_{Early}^i$=# of Early classifications across the 250 master classifiers (MCs) calculated for each noise realization, i, for the test sample ($1 \leq i \leq 160$ in this example since there are 160 different noise realization). Compute sum over all i, $\Sigma_i N_{Early}^i$.

let $N_{Late}^i$=# of Late classifications across the 250 master classifiers (MCs) calculated for noise realization, i, for the test sample ($1 \leq i \leq 160$). Compute sum over all i, $\Sigma_i N_{late}^i$.

So, $0 \leq N_{Early}^i \leq 250$ and $0 \leq N_{Late}^i \leq 250$ for all i.

And $N_{Early}^i + N_{Late}^i = 250$, for all noise realizations i.

$$\text{Noise Effect Estimator} = R$$

$$= \text{standard deviation of } N_{Early}^i /$$

$$\left(\left|\sum_i N_{Early}^i - \sum_i N_{Late}^i\right| / 320\right)$$

$$= \text{sqrt}\left(\sum_i (N_{Early}^i)^2 - \left(\sum_i N_{Early}^i\right)^2\right) /$$

$$\left(\left|\sum_i N_{Early}^i - \sum_i N_{Late}^i\right| / 320\right)$$

$$= \text{sqrt}\left(\sum_i (N_{Early}^i{}^2) - \left(\sum_i N_{Early}^i\right)^2\right) /$$

$$\left(\left|\sum_i N_{Early}^i - 20000\right| / 160\right)$$

The denominator in R, ($|\Sigma_i N_{Early}^i - \Sigma_i N_{Late}^i|/320$), gives a measure of the average difference between the numbers of Earlys and Lates that we get across the 160 noise realizations. If this number is small then the majority vote classification was close, and if it is big, it was a one-sided vote. In essence, the ratio R compares the variability in the MC labels with how one-sided it is, which is important because we want to know whether the variability we measure in noise parameter $\epsilon$ is likely to lead to an unreliable majority vote classification. That is, we do not mind a variability of say 10, if we average 220 Earlys and 30 Lates over all the 250 MCs, but we do mind a variability of 10 if we average 130 Earlys and 120 Lates over all the 250 MCs.

The final classification label for the test sample (1200, FIG. 12) is generated at step 1240. This classification will only be performed on samples with a VS1.0 classification of Good. The final classification label which is reported is as follows:

1. If the ratio R determined in step 1236 is >0.5, return the label Intermediate (or the equivalent). The patient whose sample has the Intermediate label associated with it is predicted to obtain a similar clinically meaningful benefit from chemotherapy and EGFR-Is. Note that this is regardless of the class label produced by the master classifier on the corrected feature values (1129).

2. If the ratio R determined in step 1236 is $\leq 0.5$,

A. return the Late label if the test sample label generated at 1229 is Late.

B. return the Early label if the test sample label generated at 1229 is Early.

A test sample with the Late label associated with it is predicted to obtain greater benefit from EGFR-Is as compared to chemotherapy for treatment of NSCLC cancer.

In one possible embodiment the Intermediate label is deemed to comprise those patients in which the noise effect estimator >0.5 (1. above) plus the Earlys ($\leq$=0.5 noise effect estimator and Early label). They are combined because this is clinically useful (they consists essentially of those patients leftover if you decide to give the Lates EGFR-Is and those testing as VS1.0 Poor chemotherapy. The result that the outcomes may be similar on chemotherapy and TKIs was concluded for this combined group (noise effect estimator >0.5 (1. above) plus the Earlys ($\leq$=0.5 noise effect estimator and Early label), not either group separately.

Example 4

CMC/D Classifier Generation from Genomic Data and its Use to Predict Early Relapse in Breast Cancer Patients Another example of generating a CMC/D classifier will be described in Example 4 in which the measurement data for a set of samples used in classifier development is in the form of genomic data, i.e., gene expression data. In this particular example, the data set we used for classifier development is a dataset that has been studied in the paper: Venet D, Dumont J E, Detours V (2011), "Most Random Gene Expression Signatures Are Significantly Associated with Breast Cancer Outcome" PLoS Comput Biol 7(10): e1002240.

The dataset studied here (referred to as "NKI cohort", "NKI-295") is included as a part of the Supporting Information accompanying the paper by Venet et al. This dataset has been created by microarray gene expression profiling in fresh-frozen breast cancer tissue samples taken from 295 consecutive patients who were treated at the hospital of the Netherlands Cancer Institute (described in the paper of M. J. van de Vijver et al., NEJM, 2002, v 347, p 1999-2009). All patients were treated by mastectomy or breast conserving surgery. RNA was isolated from snap-frozen tumor tissue and used to derive complementary RNA (cRNA). The microarrays included approximately 25,000 human genes and were synthesized by inkjet technology. The dataset includes additional clinical data, as well as data on overall survival (OS) and recurrence-free survival (RFS), i.e. survival free of distant metastases. A detailed description of the dataset can be found in the paper by M. J. van de Vijver et al. We work primarily with the RFS data (e.g. when defining "Early" and "Late" groups), but also perform survival analysis for overall survival (OS) data. The dataset contains 13,108 features (fluorescence measurements of distinct mRNA transcripts) that correspond to measurements of gene expression for the corresponding genes.

The clinical problem we investigated is whether we could use the CMC/D methodology described in this document using the gene expression data from breast cancer tumor samples to create a classifier that can predict the risk of recurrence. Ideally, such prediction could be used to guide treatment (radiotherapy or systemic adjuvant therapy: chemotherapy, hormonal therapy) following the breast cancer surgery. Patients with high risk of recurrence could be guided to more aggressive treatment, patients with low risk of recurrence could have less aggressive and less toxic treatment. A classifier that predicts risk of recurrence takes gene expression data as input. The output is binary: either "Early", i.e. early recurrence, i.e. high risk of recurrence, or "Late", i.e. late recurrence or no recurrence at all.

There are several known "genetic signatures" that have been proposed for predicting the risk of recurrence in breast cancer. One fairly well-known signature is the "70-gene signature" that became the basis of the commercial test known as "MammaPrint", which has been proposed in L. J. van't Veer et al, "Gene expression profiling predicts clinical outcome of breast cancer", Nature, 2002, v 415, p 530-536. This test is also believed to be the subject of several patents, including U.S. Pat. No. 7,171,311 ("Methods of assigning treatment to breast cancer patients"), U.S. Pat. No. 7,514, 209 ("Diagnosis and prognosis of breast cancer patients") and U.S. Pat. No. 7,863,001 ("Diagnosis and prognosis of breast cancer patients").

As described in the Venet et al. article, there are many other possible tests using the same genomic data resulting in very similar classification and clinical utility, but using different gene sets. One is prompted to ask the question: how is this possible? Are all features biologically meaningless? Are the combinations of genes all saying the same thing? We wanted to know what our CMC/D classifier development process tells us about this problem, and whether we could use our methodology on this data to generate a new classifier for predicting breast cancer recurrence. As demonstrated in this example, we were able to generate a classifier that is not only generalizable but has predictive power for relapse of breast cancer.

In conducting this work, we obtained the public genomic data set referred to in the Venet et al. article, split the data into classifier development and validation cohorts, developed the CMC/D classifier using the development cohort and tested its performance on the validation cohort. The data set contained 13,108 features (mRNA transcript expression levels), which presented a feature selection problem (discussed below) and our classifiers were based on subsets of 400 or fewer of the most statistically significant features. We have defined early and late initial training labels from the RFS data in the data.

In our first try at classifier development, we used 100 splits of the development sample set into training and test set realizations to define 100 master classifiers, using the methodology described at length in conjunction with FIG. 11. We started with the early/late class definitions, selected 400 features from the 13,108 available features (using t-test or SAM, typical for genomic problems), used classification error for mini-classifier filtering, and performed label flips for mis-classified samples until convergence. This process worked fine for the development set. Classifier performance was measured using a modified majority vote (MMV). MMV, and its rationale, is described in some detail later in this Example. However, when we applied the final classifier to the validation cohort we saw different performance in terms of Hazard ratios for RFS between the development and validation cohorts, in other words, our initial CMC/D classifier did not generalize as well as we would desire.

Figure 27:
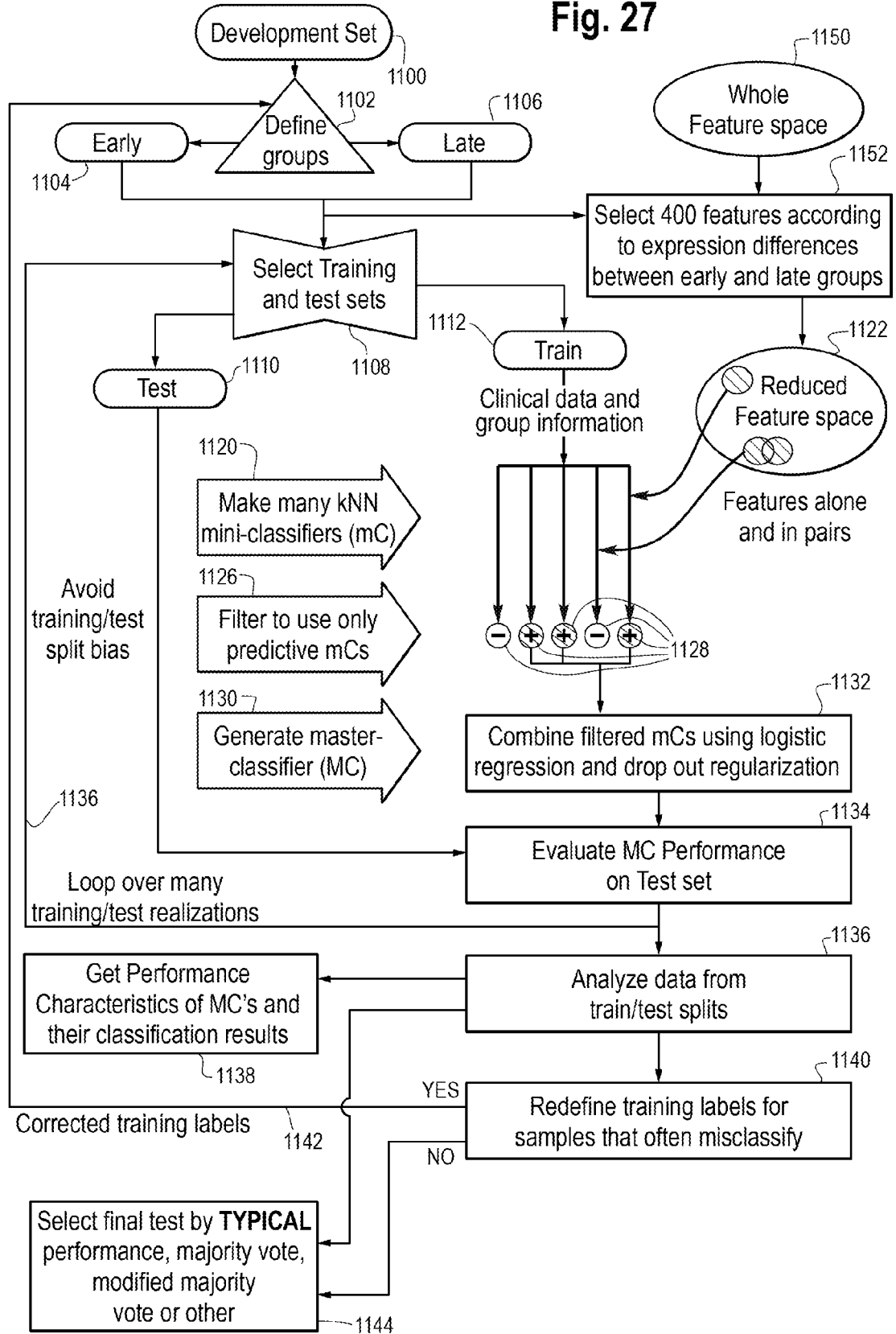
FIG. 27 is a detailed low chart showing a method for generating a CMC/D classifier from genomic measurement data and initial group/class label assignments associated with the samples in a classifier development sample set, similar to FIG. 11.
Figure 28:
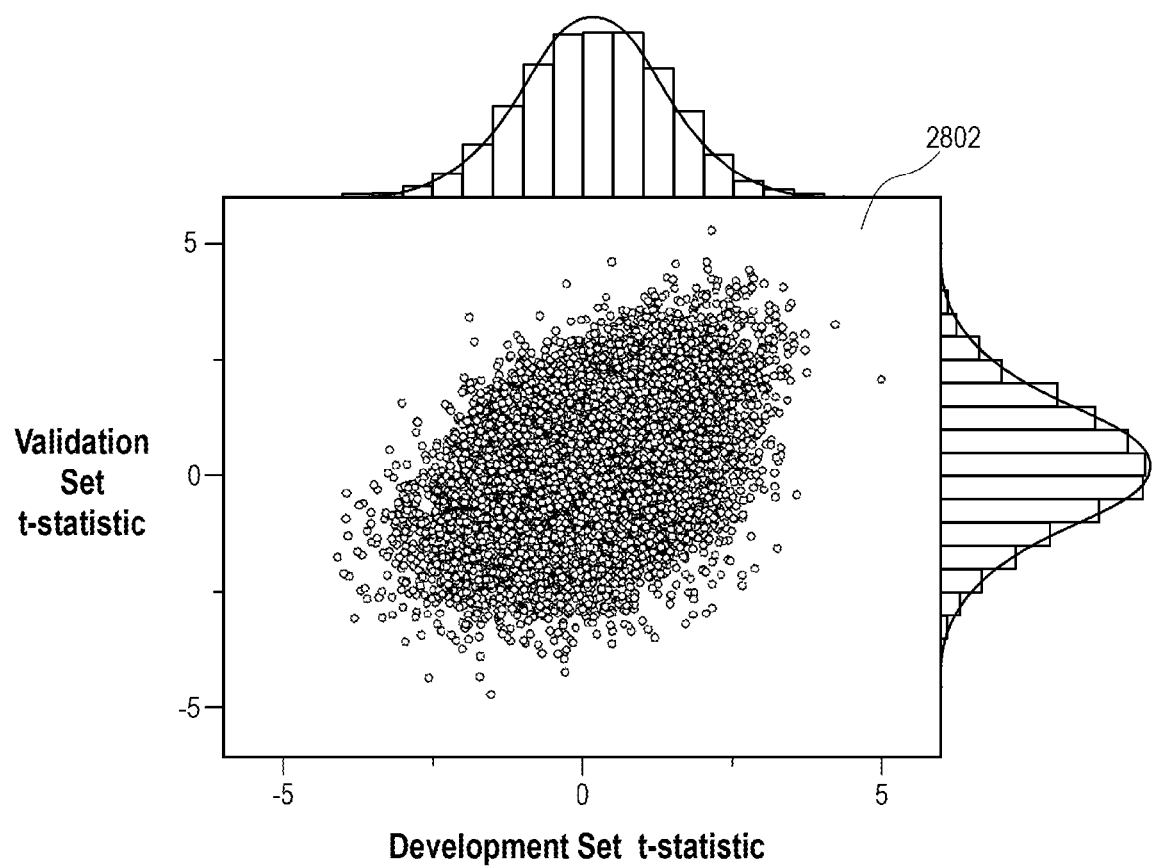
FIG. 28 is a plot of the relationship of the development set t-statistic and validation set t-statistic in the genomic Example 4 after an initial run of the classifier development method of FIG. 27 and before reselection of features and flipping of training labels for misclassified samples.

We discovered a solution to the generation problem: that the feature significance depends on the class labels, and that we could achieve better generalization of the classifier by reselecting features during the iterations of the classifier development when we redefined the class labels for samples that often misclassified (see FIG. 27, step 1152). We discovered that the expression differences rely on class labels for the Early and Late groups. It is known from statistics for class groups A and B, that features can be ordered by normalized expression differences, e.g., by means of the t-statistic: $t \sim (\text{mean }(A) - \text{mean }(B))/(\text{pooled standard deviation})$. If the group membership is incorrect, such expression differences become meaningless. To study this, we created a graph of the t-statistic of the development cohort and the validation cohort (shown in FIG. 28) for the first attempt of generating our CMC/D classifier. The graph shows that there was very little correlation between the expression ordering of features for the development and validation cohorts and the initial feature selection was not useful.

Figure 29:
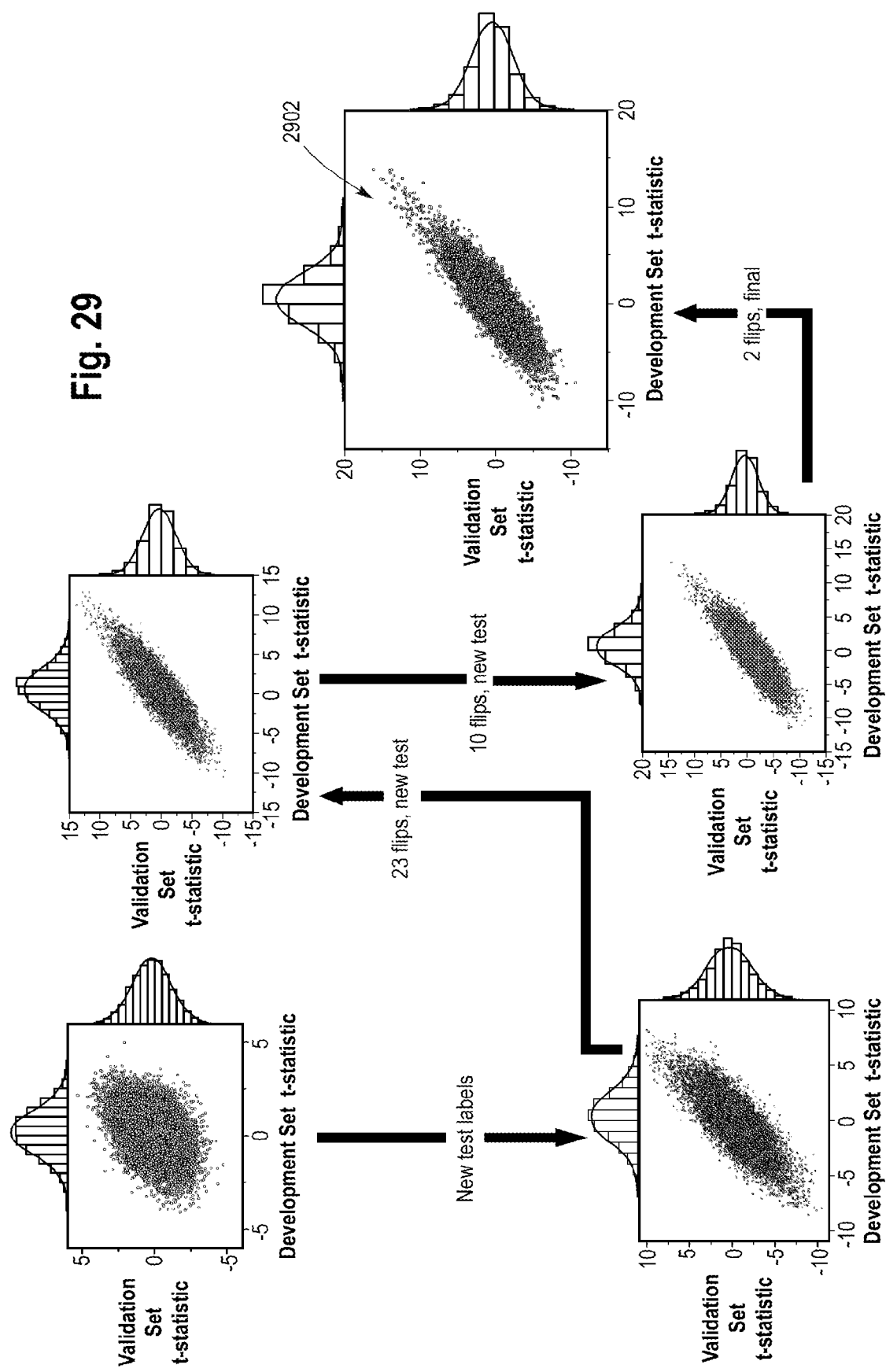
FIG. 29 is a series of plots of the relationship of the development set t-statistic and validation set t-statistic in the genomic Example 4 showing convergence of the t-statistic with successive iterations of the method with training label flips for misclassified samples and new selection of features in the data with each iteration of the method. Note that, with improved classification group label assignments and selection of new features in each iteration of the method, the expression differences (as indicated by the shape of the t-statistic plot) become similar in the development and validation cohorts.

We discovered that, with reselection of features during the label flipping step and definition of early and late groups during classifier development, we could get the CMC/D classifier to converge to a classifier and set of features which was generalizable, i.e., with improved group label assignments and refined feature selection the t-statistic of expression differences becomes similar in the development and validation cohorts. This convergence is shown in FIG. 29 as a sequence of plots of t-statistics between the development and validation cohorts for a series of CMC/D classifiers during successive iterations with flipped class labels for misclassified samples and new selection of features. Note the change in scale in the final plot on the right hand side of FIG. 29. FIG. 29 shows that on the positive expression side of the right hand plot differentiating features emerge, which indicates that the class labels are consistent with the molecular data. Moreover, the Hazard ratios of RFS and OS in the development and validation cohorts converge to agreement during this iterative process, as indicated below:

| Flip iteration | RFS Develop | RFS Validation | OS Develop | OS Validation |
| --- | --- | --- | --- | --- |
| Original | 7.38 | 3.752 | 11.73 | 5.678 |
| After 1 | 3.451 | 3.277 | 5.878 | 4.954 |
| After 2 | 3.050 | 3.540 | 5.066 | 5.115 |
| After 3 | 2.814 | 3.568 | 4.346 | 5.333 |

The conclusions that we draw from this exercise is that we have solved the multiple classifier problem outlined in Venet et al. One needs to adjust the training labels iteratively during classifier development and feature select according to the "correct" (revised) training labels. We reached a unique feature set that produces a generalized classifier for early breast cancer recurrence prediction. Perhaps there is a unique molecular signature in the Venet et al. data after all. We further note that enhancements to the filtering of the mini-classifiers during CMC/D classifier development improves performance somewhat. These aspects, as well as feature selection techniques, will be described in the following more detailed explanation.

CMC/D Classifier Development

In this example, we applied our CMC/D approach to develop several such classifiers, and studied their performance. The methodology we used is shown in FIG. 27; it is similar to the methodology described above in Examples 1-3 except that we were using gene expression data and not mass spectrometry data. Furthermore, during iterations of the classifier development we reselected features (step 1152) from the available feature space (1150) of 13,108 features and did k-NN classification with the mini-classifiers in the reduced feature space (1122) in step 1120.

As is usual for the classifier that classifies each sample into either "Early" (high-risk) or "Late" (low-risk) group, performance of the classifier is characterized by the hazard ratio (HR) between the groups, and by the corresponding survival curves (Kaplan-Meier plots).

Apart from performance, an important characteristic of the classifier is how well it generalizes to the new (previously unseen) data. Ideally, performance on the new data should be similar to performance measured on the data used to develop the classifier. Classifiers that generalize poorly are prone to overfitting, i.e. they show high performance on the development data, but significantly lower performance on the new data. In order to be able to study how well the classifier generalizes, we split the Venet et al. public data set into Cohort1 (development cohort, the development sample set 1100 in FIG. 27) and Cohort2 (a validation cohort). In particular, we split the data into Cohort1 (development cohort) and Cohort2 (validation cohort) as follows:
1) split the data (295 samples) into "RFS censored" and "RFS uncensored" subsets
2) in both subsets, order by RFS
3) in both ordered subsets, use 1-2-1-2-... pattern to assign samples to Cohort1 or Cohort2.
Thus, we used a stratified splitting of the sample set, the goal being to obtain two cohorts that are very similar with respect to the RFS. Resulting Cohort1 includes 148 patients. Cohort2 includes 147 patients.

The way we build classifiers for the gene expression data using the CMC/D approach is very similar to how we do it for the mass spectral data and is explained in great detail above. Here is the general outline of the approach, described with reference to FIG. 27. We split the public genomic data set into a development set cohort 1100 (Cohort1) and a validation cohort (Cohort2). The classification groups are defined for each sample in the two cohorts (step 1102). Classifier development proceeds on the development set cohort as follows. The development cohort is split into the training set and the test set (step 1108). We generate many such splits (called realizations; in this study we use 100 realizations) as indicated by the loop 1136. This way we can make sure that our classifier does not depend on the peculiarities of a particular split.

For each realization, we build a "master classifier" MC as follows. First, we make a large number of "mini-classifiers" (step 1120), which are k-NN classifiers using 1 feature or 2 features selected from the data for the samples. For 400 features (mRNA transcripts), which is how many we typically use in this example, there are 400 possible mini-classifiers based on 1 feature, plus 79,800 possible mini-classifiers based on 2 features. Thus, we have 80,200 possible mini-classifiers. For each mini-classifier, we estimate performance, using a "training set" part of the realization. Then mini-classifiers are filtered (step 1126): we only keep the mini-classifiers which show performance that satisfies given criteria, which are listed as "Filtering parameters" in the following table:

| Study # | Clinical Question | Filtering Parameters | # features used |
|---|---|---|---|
| 1 | Predicting breast cancer recurrence | 0.85 < classification accuracy < 1.0 | 400, as selected by t-test between original Early and Late in Cohort1 |
| 2 | Predicting breast cancer recurrence | 0.85 < classification accuracy < 1.0 | 400, as selected by t-test between original Early and Late in Cohort2 |
| 4 | Predicting breast cancer recurrence | 6 < hazard ratio < 20 | 400, as re-selected by t-test after each flip, using t-test between Early and Late, in Cohort1 |
| 5 | Predicting breast cancer recurrence | 6 < hazard ratio < 20 | 100, as re-selected by t-test after each flip, using t-test between Early and Late, in Cohort1 |
| 6 | Predicting breast cancer recurrence | 3 < hazard ratio < 10, and 0.7 < error in true early recurrence group < 1.0 | 400, as re-selected by t-test after each flip, using t-test between Early and Late, in Cohort1 |

In the above table, study # refers to different CMC/D classifier generation exercises using different numbers of features, or different filtering options for selection of filtered mini-classifiers (FIG. 27, step 1126). Typically, from 10% to 30% of mini-classifiers pass filtering. Then the "Master Classifier" is constructed using logistic regression with extreme drop-out (FIG. 27, step 1130). The output of the mini-classifiers serves as the input of logistic regression. When computing parameters of logistic regression, we use dropout: namely, we do many dropout iterations, each time we randomly use only a small number (Leave-in number) of mini-classifiers. These parameters are typically as follows:

| Master classifier parameters | |
|---|---|
| Leave-in number | 4 |
| Number of drop-out iterations | 20000 |

Eventually, as indicated in step 1132 the master classifier MC is constructed by averaging the parameters of logistic regression that come out of all the drop-out iterations. "Early" and "Late" classification labels are assigned using the threshold 0.5 for the output of logistic regression.

Classification of new samples (i.e., the final classifier as selected in step 1144) is achieved by majority vote of master classifiers resulting from all training set/test set realizations (in our case, majority vote of 100 master classifiers).

Iterative Label Flips

We also perform iterative development of the classifier by doing label flips (redefined training labels in step 1140). Namely, first we develop a master classifier using the original "Early" and "Late" labels as derived from the RFS data (50 samples with the shortest RFS are "Early", 50 samples with the longest RFS are "Late"). Then, in step 1140 we do a "label flip" by replacing original labels by the labels assigned by the classifier (only those samples which are misclassified get new labels). Then we re-develop the classifier (repeat steps 1108, 1120, 1126, 1128, 1130, and selection of new features in step 1152). We iterate this procedure several times, until we get close to convergence, namely almost all labels stay the same. The general observation is that for this dataset, one observes some decrease in performance in the course of label flip iterations, but generalizability improves, namely performance, as measured by the hazard ratio between "Early" and "Late" groups, becomes similar for the development cohort (Cohort1) and the validation cohort (Cohort2).

Feature Selection and Statistical Significance of Features

While the CMC/D framework that we use here is the same as in case of mass spectrometry data, the single most important difference is that in gene expression data there are so many possible genomic features (in this case, 13,108, the whole feature space 1150 in FIG. 27) available for use, that we have to deal with feature selection. In this exercise we selected 400 features in the kNN mini-classifiers. As an additional exercise, we repeated the classifier development for the 100 most significant features. We found that with 100 features the classifier performance was somewhat worse than when the classifier was trained using 400 features. Features can be either selected once and for all before the creation of the classifier, or they can be re-selected at each label-flip iteration using the labels assigned by the classifier as indicated at step 1152 in FIG. 27. The main observation is that in the latter case statistical significance of features increases dramatically, as well as the correlation of statistical significance of features between Cohort1 and Cohort2. Hence, for the genomic data in this example the use of label flip and reiteration of the master classifier steps in conjunction with re-selection of features is considered a preferred embodiment.

In developing the classifier and repeating the iterations with the flipping of class labels for misclassified samples, we noticed successive iterations sometimes tended to result in an increasing imbalance in the number of Early and Late class members, i.e., the number of members in the Early group was getting progressively larger and the number of members in the Late group was getting progressively smaller. We tried a new strategy: when we performed the label flips we kept the number members in the Early and Late groups balanced. In particular, after the classifier assigns 'Early' and 'Late' labels, we determine the size of resulting 'Early' and 'Late' groups. If the size of the 'Early' group is greater than 50, we move several samples with the longest RFS from 'Early' to 'intermediate'. If the size of the 'Early' group is less than 50, we move several 'intermediate' samples which classify as 'Early' and have the shortest RFS, from 'intermediate' to 'Early'. If the size of the 'Late' group is greater than 50, we move several samples with the shortest RFS from 'Late' to 'intermediate'. If the size of the 'Late' group is less than 50, we move several 'intermediate' samples which classify as 'Late' and have the longest RFS, from 'intermediate' to 'Late'. Thus we rebalance the groups so that after the flip we have 50 'Early' and 50 'Late'.

Figure 32B:
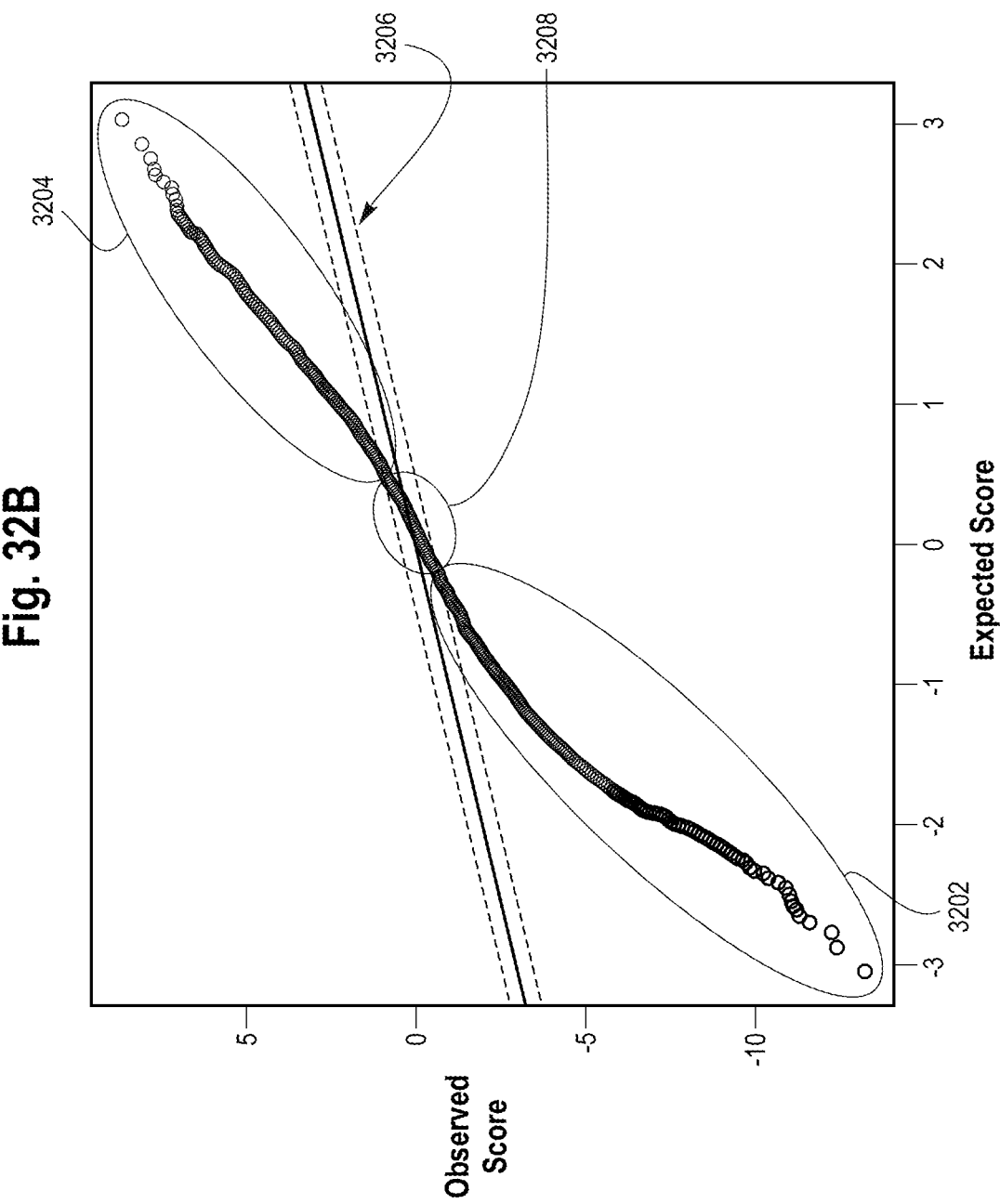

During each successive iteration of the classifier generation process, we select a new set of 400 features from the available set of 13,108 features, using statistical measures of significance of features such as t-test. Another method to measure statistical significance is SAM (significance analysis of microarrays). Background information on this technique is described in the paper of V. Tusher et al., "Significance analysis of microarrays applied to ionizing radiation response" PNAS Apr. 24, 2001 v. 98 n. 9 pp. 5116-5121, the content of which is incorporated by reference herein. FIG. 32A shows the SAM plot for Cohort1 and the original definitions of Early and Late groups. FIG. 32B shows the SAM plot for Cohort1 using HR filtering and group size rebalancing after 3 label flip iterations. Basically, the points in regions 3202 and 3204 (that are outside the strip 3206) correspond to statistically significantly up- or down-regulated features. The points 3208 inside the strip 3206 correspond to features that do not show statistically significant up- or down-regulation. By comparing FIGS. 32A and 32B, one observes that after the flips more features become statistically significantly different between "Early" and "Late" groups, and more strongly so.

Results

Figure 30:
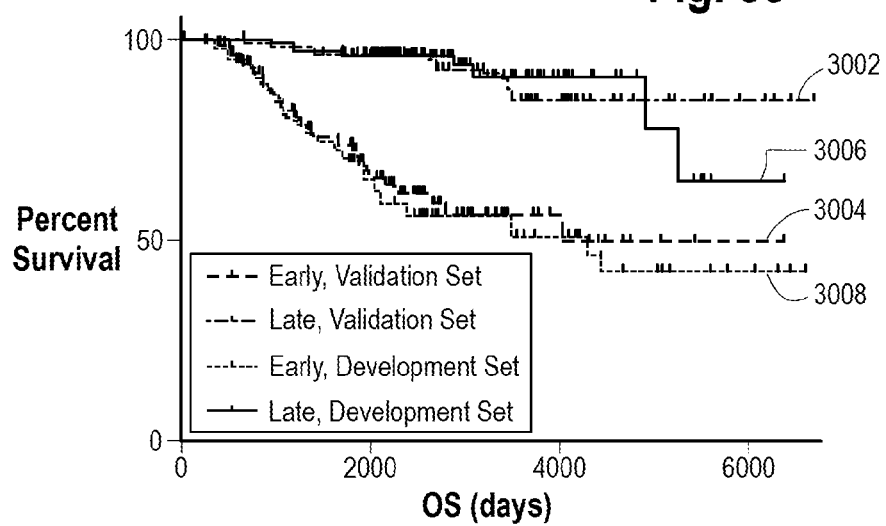
FIG. 30 is a plot of Kaplan-Meyer survival curves for the patients genomic example 4 showing the ability of the final CMC/D classifier of Example 4 to predict wither a patient is likely to have early relapse of breast cancer when their genomic data is classified as Early.

FIG. 30 is a plot of the Kaplan-Meyer overall survival curves showing the ability of the classifier we developed to separate those patients having improved overall survival (class label Late) from those patients that have relatively poor overall survival, i.e., increased risk of relapse of the breast cancer (class label Early). In FIG. 30, the Kalan-Meyer plots for the development sample set (Cohort1) and the validation sample set (Cohort2) are shown superimposed on the same plot. As indicated by the closeness of the plots 3002 and 3006 (Late group), and 3004, 3008 (Early group), the classifier we developed using the development sample set is not overfitted; i.e., it provides the same results to the new data in the validation sample set. The statistics are as follows:

Cohort 1: Hazard Ratio 4.346 95% CI of ratio 2.401 to 7.863
Cohort 2: Hazard Ratio 5.333 95% CI of ratio 2.863 to 10.60

We note that the Kaplan-Meyer plots of FIG. 30 are similar to the Kaplan-Meyer plots shown at page 2004 of the van de Vijver et al. NEJM paper.

Methods of Analysis of Results from the CMC/D Master Classifiers

Within the CMC/D process, each training/test split realization produces one master classifier (MC) generated from the combination of mini-classifiers (mCs) through logistic regression with dropout regularization. The output of this logistic regression is, in the first instance, not a binary label but a continuous probability taking values between 0 and 1. Applying a cutoff (e.g. 0.5, but any choice is possible) to these MC probabilities, we can turn them from a continuous variable into a binary label. So, each MC produces a classification label for a given sample. However, this step is not essential, and one can choose not to apply a cutoff here, but instead to retain the information in the continuous probability variable.

Having obtained the outputs from the MCs (either in terms of binary labels via use of a cutoff or in terms of probabilities), these need to be combined ("bagged" in learning theory language) across the MCs to produce a single binary classification for a particular sample. The way the CMC/D process is implemented means that when a sample is used in the training set of the MC for a realization, the sample almost always classifies correctly (in terms of binary labels after implementation of a cutoff or in terms of probabilities close to target of 0 for one class and 1 for the other class). Hence, use of a simple majority vote over all MCs can produce an artificially good assessment of classifier performance for samples that are used in the training set for some of the MCs. To avoid this, we can use a modified majority vote (MMV) to obtain a classification for samples used directly in the development of the classifier. This procedure is a majority vote over the MC outputs only when the sample is not included in the training set of the MC. (For samples never used in training the MCs, the majority vote and MMV are identical.) This MMV can be used after implementation of a cutoff by taking a majority vote of the classifications produced by all MCs for which the sample is not included in the training set. If, instead, we want to avoid the use of a cutoff at this point and work with the MC probability outputs, the average of the probabilities across the MCs for which the sample is not included in the training set can be calculated. Taking the latter approach, the MMV produces another, averaged, continuous variable that can take values between 0 and 1, an average probability of being in a particular class. This can be converted into a binary classification label via implementation of a cutoff after averaging over MCs.

Direct averaging of the probabilities provides some advantages. If we obtain an average probability for each sample, it is possible to assess simultaneously the performance of the whole family of classifiers that can be produced by imposing different cutoffs on the average probability. This can be done by using the standard receiver operating characteristic (ROC) curve approach. See http://en.wikipedia.org/wiki/Receiver_operating_characteristic for background information. For a particular choice of cutoff on the average probabilities, classification labels are generated for all samples and these labels can be compared with the known class labels to calculate the sensitivity and specificity of the classifier defined by this cutoff. This can be carried out for many values of the cutoff and the results plotted in terms of sensitivity versus 1-specificity (the ROC curve). Overall performance of the family of classifiers can be characterized by the area under the curve (AUC). The ROC curve can be inspected and a particular cutoff selected that best suits the target performance desired for the classifier, in terms of sensitivity and specificity.

Figure 31:
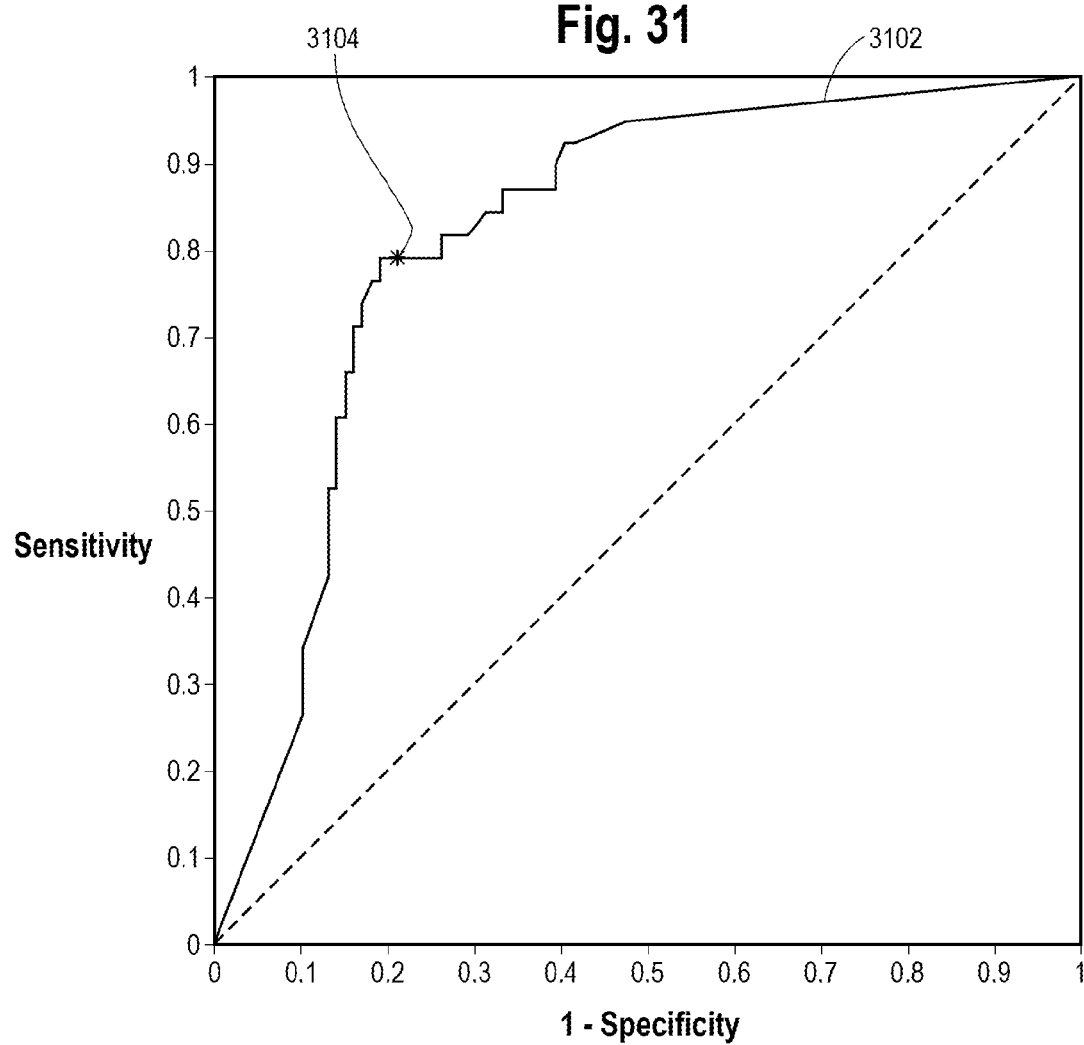
FIG. 31 is a receiver operating characteristic (ROC) curve produced using the average master classifier (MC) probabilities for the mRNA breast cancer early relapse classification problem of Example 4.

To give an example of these approaches, CMC/D was applied to a genomic dataset of mRNA data obtained from breast cancer patients who had undergone surgery. The aim was to produce a classifier able to identify patients relapsing before five years after surgery (Early Relapse). Two hundred and fifty features (gene expressions) were selected from the over 13,000 available features on the basis of a t-test between the development set classes of Early Relapse (patients relapsing before 5 years) or No Early Relapse (patients not relapsing before 5 years). The CMC/D process was implemented using 200 training/test set splits (realizations). Using a cutoff of 0.5 on each MC probability output, 200 MC class labels were calculated for each patient and the modified majority vote procedure used to generate a classification. This produced a CMC/D classifier with 79% sensitivity and 79% specificity for identification of breast cancer relapse before 5 years. Using the MC probability outputs, average probabilities were obtained for each sample and the ROC curve calculated, shown in FIG. 31.

The solid curve (FIG. 31, 3102) shows the possible performances (in terms of sensitivity and specificity) for the family of classifiers that can be defined by applying a cutoff to the average MC probabilities. The AUC is 0.82, indicating considerable classification power for this family of classifiers (AUC=0.5 indicates random classification and AUC=1 is perfect classification.) The star symbol 3104 in FIG. 31 indicates the performance of the CMC/D classifier obtained from applying a cutoff of 0.5 to the individual MC probabilities. This ROC curve allows us to select a cutoff to obtain an Early Relapse classifier most appropriate to the particular clinical need. For example, if it is essential to have a high sensitivity, perhaps so that a very high proportion of at-risk patients receive appropriate medical interventions to prevent early relapse, a point on the ROC curve with high sensitivity can be selected at the expense of specificity (perhaps sensitivity=0.9 and specificity=0.6). Alternatively, if the only medical intervention has a high risk of serious side effects, it might be more appropriate to select a point on the ROC curve corresponding to higher specificity (perhaps sensitivity=0.8 and specificity=0.8).

Further Considerations

In summary of the above methods, we have demonstrated several examples of generation of a new type of classifier, referred to CMC/D herein, to make predictions, among other things, of whether a patient is likely to benefit from anti-cancer drugs. We have also demonstrated that the methodology can be conducted in the situation where the class labels for a development sample set (e.g., Early and Late) are assigned at the same time as the classifier is generated. Examples 1, 3, and 4 make use of separation of a development sample set into training and test sets, construction of many individual mini-classifiers, filtering of the mini-classifiers, and combining the mini-classifiers by means of a regularized combination method, such as logistic regression and extreme drop-out regularization. Redefinition of the class labels in the course of generating the classifier has also been described. A final classifier can take several possible forms, for example an average of the master classifiers after logistic regression and drop-out regularization over multiple splits of the development set into training and test sets, or a combination of all master classifiers from all training and test set splits, e.g., using a majority vote of the combination, a selection of one particular master classifier representing typical performance, or any one of the above, further taking into account statistical analysis of the voting of the master classifier on the feature values that are modified to simulate noise in the data. Therefore, there is considerable flexibility in the particular design of the final classifier and the scope of the present disclosure is intended to cover all such designs.

Furthermore, while the present examples of classifier development have been given in the context of making predictions of patient benefit from certain drugs, it will be apparent that the CMC/D classifier could be used to make other types of classifications, such as for example, whether a patient is a member of a class A or class B, where class A and B have a diagnostic or other meaning. The types of data sets and class labels associated with the data set are not particularly important. As a further example, the CMC/D classifier could be used to make classifications of test samples in completely different fields beyond medicine. It would also be a natural extension to the CMC/D method to use, for example, protein expression levels, genomic data, either separately or in combination as an input data set in the form of measurement data/features derived from multiple different assessments of a single patient sample or even derived from different sample modalities from a single patient.

With regards to genomic data (gene expression, protein expression, mRNA transcript expression or other) it will be appreciated that the precise nature of the feature values of genomic data it not particularly important. The version of genomic data from the Venet et al. paper that we are using in Example 4 is based on fluorescent measurements, but in all likelihood these measurements also went through some preprocessing and possibly calibration and normalization steps that are gene chip-specific and usually done with the software that comes with the gene chip, and are probably not raw measurements. We understand that the data set represents Venet et al.'s best effort to translate raw fluorescence measurements to sensible numbers characterizing the amount of mRNA. Other physical quantities besides fluorescence measurements could be used, for example mass measurements.

The appended claims are offered as further descriptions of the disclosed inventions.

EXAMPLE 1 APPENDICES

Example 1 Appendix A

Samples Used in this Project

| Treatment Arm | Sample ID |
|---|---|
| Control | 14 |
| Control | 15 |
| Control | 58 |
| Control | 59 |
| Control | 62 |
| Control | 63 |
| Control | 65 |
| Control | 68 |
| Control | 70 |
| Control | 72 |
| Control | 74 |
| Control | 75 |
| Control | 77 |
| Control | 84 |
| Control | 85 |
| Control | 88 |
| Control | 89 |
| Control | 90 |
| Control | 91 |
| Control | 116 |
| Control | 119 |
| Control | 120 |
| Control | 121 |
| Control | 122 |
| Control | 130 |
| Control | 135 |
| Control | 136 |
| Control | 138 |
| Control | 503 |
| Control | 506 |
| Control | 510 |
| Control | 512 |
| Control | 516 |
| Control | 517 |
| Control | 521 |
| Control | 524 |
| Control | 525 |
| Control | 527 |
| Control | 529 |
| Control | 530 |
| Control | 533 |
| Control | 535 |
| Control | 537 |
| Control | 538 |
| Control | 543 |
| Control | 546 |
| GI-4000 | 57 |
| GI-4000 | 61 |
| GI-4000 | 66 |
| GI-4000 | 67 |
| GI-4000 | 71 |
| GI-4000 | 81 |
| GI-4000 | 83 |
| GI-4000 | 87 |
| GI-4000 | 115 |
| GI-4000 | 117 |
| GI-4000 | 118 |
| GI-4000 | 123 |
| GI-4000 | 125 |
| GI-4000 | 126 |
| GI-4000 | 131 |
| GI-4000 | 508 |
| GI-4000 | 509 |
| GI-4000 | 511 |
| GI-4000 | 515 |
| GI-4000 | 534 |
| GI-4000 | 536 |
| GI-4000 | 542 |
| GI-4000 | 128 |
| GI-4000 | 531 |
| GI-4000 | 56 |
| GI-4000 | 60 |
| GI-4000 | 64 |
| GI-4000 | 69 |
| GI-4000 | 73 |
| GI-4000 | 78 |
| GI-4000 | 80 |
| GI-4000 | 86 |
| GI-4000 | 132 |
| GI-4000 | 137 |
| GI-4000 | 502 |
| GI-4000 | 504 |
| GI-4000 | 513 |
| GI-4000 | 519 |
| GI-4000 | 523 |
| GI-4000 | 526 |
| GI-4000 | 528 |
| GI-4000 | 532 |
| GI-4000 | 539 |
| GI-4000 | 544 |

Example 1 Appendix B

Features Used in CMC/D Classifiers

| Feature Number | Center of Feature (m/Z) |
|---|---|
| 1 | 3108 |
| 2 | 3130 |
| 3 | 3217 |
| 4 | 3236 |
| 5 | 3246 |
| 6 | 3266 |
| 7 | 3368 |
| 8 | 3428 |
| 9 | 3463 |
| 10 | 3723 |
| 11 | 3841 |
| 12 | 3893 |
| 13 | 3935 |
| 14 | 4135 |
| 15 | 4186 |
| 16 | 4207 |
| 17 | 4289 |
| 18 | 4444 |
| 19 | 4458 |
| 20 | 4469 |
| 21 | 4567 |
| 22 | 4624 |
| 23 | 4686 |
| 24 | 4789 |
| 25 | 4855 |
| 26 | 4962 |
| 27 | 4997 |
| 28 | 5020 |
| 29 | 5066 |
| 30 | 5104 |
| 31 | 5136 |
| 32 | 5193 |
| 33 | 5391 |
| 34 | 5571 |
| 35 | 5718 |
| 36 | 5734 |
| 37 | 5762 |
| 38 | 5776 |
| 39 | 5841 |
| 40 | 5862 |
| 41 | 5907 |
| 42 | 6171 |
| 43 | 6772 |
| 44 | 6893 |
| 45 | 6982 |

| Feature Number | Center of Feature (m/Z) |
|---|---|
| 46 | 7041 |
| 47 | 7240 |
| 48 | 7385 |
| 49 | 7690 |
| 50 | 8357 |
| 51 | 8762 |
| 52 | 8894 |
| 53 | 8912 |
| 54 | 8992 |
| 55 | 9566 |
| 56 | 9664 |
| 57 | 9707 |
| 58 | 9750 |
| 59 | 9863 |
| 60 | 10000 |
| 61 | 10071 |
| 62 | 10091 |
| 63 | 10201 |
| 64 | 11380 |
| 65 | 11402 |
| 66 | 11432 |
| 67 | 11466 |
| 68 | 11488 |
| 69 | 11521 |
| 70 | 11544 |
| 71 | 11620 |
| 72 | 11676 |
| 73 | 11699 |
| 74 | 11723 |
| 75 | 11744 |
| 76 | 11883 |
| 77 | 11901 |
| 78 | 12837 |
| 79 | 12856 |
| 80 | 12955 |
| 81 | 12976 |
| 82 | 13062 |
| 83 | 13145 |
| 84 | 13264 |
| 85 | 13306 |
| 86 | 13706 |
| 87 | 13735 |
| 88 | 13782 |
| 89 | 13901 |
| 90 | 14031 |
| 91 | 14112 |
| 92 | 14138 |
| 93 | 14281 |
| 94 | 22988 |
| 95 | 23021 |
| 96 | 23221 |
| 97 | 28038 |
| 98 | 28232 |
| 99 | 28439 |
| 100 | 28805 |

Example 1 Appendix C

Samples from the GI-4000 Arm Assigned to Each TTR Group (Early, Late, Intermediate)

| Group | Sample ID |
|---|---|
| Early | 57 |
| Early | 61 |
| Early | 66 |
| Early | 67 |
| Early | 71 |
| Early | 81 |
| Early | 83 |
| Early | 87 |
| Early | 115 |
| Early | 117 |
| Early | 118 |
| Early | 123 |
| Early | 125 |
| Early | 126 |
| Early | 131 |
| Early | 508 |
| Early | 509 |
| Early | 511 |
| Early | 515 |
| Early | 534 |
| Early | 536 |
| Early | 542 |
| Intermediate | 128 |
| Intermediate | 531 |
| Late | 56 |
| Late | 60 |
| Late | 64 |
| Late | 69 |
| Late | 73 |
| Late | 78 |
| Late | 80 |
| Late | 86 |
| Late | 132 |
| Late | 137 |
| Late | 502 |
| Late | 504 |
| Late | 513 |
| Late | 519 |
| Late | 523 |
| Late | 526 |
| Late | 528 |
| Late | 532 |
| Late | 539 |
| Late | 544 |

Example 1 Appendix D

Samples from the Control Arm Assigned to Training and Test Sets

| Training/Test Set | Sample ID |
|---|---|
| Training | 14 |
| Training | 15 |
| Training | 58 |
| Training | 65 |
| Training | 72 |
| Training | 75 |
| Training | 85 |
| Training | 89 |
| Training | 116 |
| Training | 120 |
| Training | 122 |
| Training | 130 |
| Training | 135 |
| Training | 136 |
| Training | 517 |
| Training | 525 |
| Training | 527 |
| Training | 529 |
| Training | 533 |
| Training | 535 |
| Training | 538 |
| Training | 543 |
| Training | 546 |
| Test | 59 |
| Test | 62 |
| Test | 63 |
| Test | 68 |
| Test | 70 |
| Test | 74 |

Example 1 Appendix E (continued)

| Training/Test Set | Sample ID |
|---|---|
| Test | 77 |
| Test | 84 |
| Test | 88 |
| Test | 90 |
| Test | 91 |
| Test | 119 |
| Test | 121 |
| Test | 138 |
| Test | 503 |
| Test | 506 |
| Test | 510 |
| Test | 512 |
| Test | 516 |
| Test | 521 |
| Test | 524 |
| Test | 530 |
| Test | 537 |

Example 1 Appendix E

Samples from the GI-4000 Arm Assigned to Each TTR Group (Early, Late, Intermediate) after Update of Labels

| | |
|---|---|
| Early | 57 |
| Early | 60 |
| Early | 61 |
| Early | 66 |
| Early | 67 |
| Early | 81 |
| Early | 83 |
| Early | 87 |
| Early | 115 |
| Early | 117 |
| Early | 118 |
| Early | 123 |
| Early | 131 |
| Early | 132 |
| Early | 502 |
| Early | 509 |
| Early | 511 |
| Early | 513 |
| Early | 515 |
| Early | 534 |
| Early | 536 |
| Early | 542 |
| Intermediate | 128 |
| Intermediate | 528 |
| Late | 56 |
| Late | 64 |
| Late | 69 |
| Late | 71 |
| Late | 73 |
| Late | 78 |
| Late | 80 |
| Late | 86 |
| Late | 125 |
| Late | 126 |
| Late | 137 |
| Late | 504 |
| Late | 508 |
| Late | 519 |
| Late | 523 |
| Late | 526 |
| Late | 531 |
| Late | 532 |
| Late | 539 |
| Late | 544 |

Example 1 Appendix F

Classification of Samples by Selected Master Classifier

| Sample ID | Classification |
|---|---|
| 14 | Early |
| 15 | Early |
| 57 | Early |
| 58 | Early |
| 60 | Early |
| 61 | Early |
| 62 | Early |
| 65 | Early |
| 66 | Early |
| 67 | Early |
| 68 | Early |
| 70 | Early |
| 72 | Early |
| 75 | Early |
| 81 | Early |
| 83 | Early |
| 85 | Early |
| 87 | Early |
| 89 | Early |
| 90 | Early |
| 115 | Early |
| 116 | Early |
| 118 | Early |
| 119 | Early |
| 121 | Early |
| 123 | Early |
| 125 | Early |
| 130 | Early |
| 131 | Early |
| 132 | Early |
| 136 | Early |
| 138 | Early |
| 502 | Early |
| 509 | Early |
| 511 | Early |
| 513 | Early |
| 515 | Early |
| 516 | Early |
| 521 | Early |
| 524 | Early |
| 527 | Early |
| 528 | Early |
| 529 | Early |
| 533 | Early |
| 534 | Early |
| 535 | Early |
| 536 | Early |
| 537 | Early |
| 538 | Early |
| 542 | Early |
| 546 | Early |
| 56 | Late |
| 59 | Late |
| 63 | Late |
| 64 | Late |
| 69 | Late |
| 71 | Late |
| 73 | Late |
| 74 | Late |
| 77 | Late |
| 78 | Late |
| 80 | Late |
| 84 | Late |
| 86 | Late |
| 88 | Late |
| 91 | Late |
| 117 | Late |
| 120 | Late |
| 122 | Late |
| 126 | Late |
| 128 | Late |
| 135 | Late |

-continued

| Sample ID | Classification |
|---|---|
| 137 | Late |
| 503 | Late |
| 504 | Late |
| 506 | Late |
| 508 | Late |
| 510 | Late |
| 512 | Late |
| 517 | Late |
| 519 | Late |
| 523 | Late |
| 525 | Late |
| 526 | Late |
| 530 | Late |
| 531 | Late |
| 532 | Late |
| 539 | Late |
| 543 | Late |
| 544 | Late |

EXAMPLE 3 APPENDICES

Example 3 Appendix A

Samples Used in Classifier Development

| Sample ID |
|---|
| ICA_1 |
| ICA_10 |
| ICA_11 |
| ICA_12 |
| ICA_13 |
| ICA_14 |
| ICA_15 |
| ICA_17 |
| ICA_18 |
| ICA_19 |
| ICA_2 |
| ICA_20 |
| ICA_21 |
| ICA_22 |
| ICA_23 |
| ICA_24 |
| ICA_25 |
| ICA_26 |
| ICA_27 |
| ICA_28 |
| ICA_29 |
| ICA_3 |
| ICA_30 |
| ICA_31 |
| ICA_32 |
| ICA_34 |
| ICA_35 |
| ICA_36 |
| ICA_38 |
| ICA_39 |
| ICA_4 |
| ICA_40 |
| ICA_41 |
| ICA_42 |
| ICA_43 |
| ICA_44 |
| ICA_45 |
| ICA_46 |
| ICA_47 |
| ICA_48 |
| ICA_49 |
| ICA_5 |
| ICA_50 |
| ICA_51 |
| ICA_52 |

-continued

| Sample ID |
|---|
| ICA_54 |
| ICA_55 |
| ICA_56 |
| ICA_57 |
| ICA_58 |
| ICA_59 |
| ICA_6 |
| ICA_60 |
| ICA_61 |
| ICA_63 |
| ICA_64 |
| ICA_65 |
| ICA_67 |
| ICA_68 |
| ICA_69 |
| ICA_7 |
| ICA_70 |
| ICA_8 |
| ICB_1 |
| ICB_10 |
| ICB_11 |
| ICB_12 |
| ICB_13 |
| ICB_14 |
| ICB_15 |
| ICB_16 |
| ICB_17 |
| ICB_18 |
| ICB_19 |
| ICB_2 |
| ICB_20 |
| ICB_21 |
| ICB_22 |
| ICB_23 |
| ICB_24 |
| ICB_25 |
| ICB_26 |
| ICB_27 |
| ICB_28 |
| ICB_29 |
| ICB_3 |
| ICB_30 |
| ICB_31 |
| ICB_32 |
| ICB_33 |
| ICB_34 |
| ICB_35 |
| ICB_36 |
| ICB_37 |
| ICB_38 |
| ICB_39 |
| ICB_4 |
| ICB_40 |
| ICB_41 |
| ICB_42 |
| ICB_43 |
| ICB_44 |
| ICB_45 |
| ICB_46 |
| ICB_47 |
| ICB_48 |
| ICB_49 |
| ICB_5 |
| ICB_50 |
| ICB_51 |
| ICB_52 |
| ICB_53 |
| ICB_54 |
| ICB_55 |
| ICB_56 |
| ICB_57 |
| ICB_58 |
| ICB_59 |
| ICB_6 |
| ICB_60 |
| ICB_61 |
| ICB_62 |

| Sample ID |
| --- |
| ICB_63 |
| ICB_64 |
| ICB_65 |
| ICB_66 |
| ICB_67 |
| ICB_8 |
| ICB_9 |
| ICC_1 |
| ICC_10 |
| ICC_11 |
| ICC_12 |
| ICC_13 |
| ICC_14 |
| ICC_15 |
| ICC_16 |
| ICC_17 |
| ICC_18 |
| ICC_19 |
| ICC_2 |
| ICC_20 |
| ICC_21 |
| ICC_22 |
| ICC_23 |
| ICC_24 |
| ICC_25 |
| ICC_26 |
| ICC_27 |
| ICC_28 |
| ICC_29 |
| ICC_3 |
| ICC_30 |
| ICC_31 |
| ICC_32 |
| ICC_4 |
| ICC_5 |
| ICC_6 |
| ICC_7 |
| ICC_8 |
| ICC_9 |

Example 3 Appendix B

Features Used in CMC/D Classifiers

| Center | Left | Right |
| --- | --- | --- |
| 3218.7386 | 3206.9871 | 3230.49 |
| 3315.4528 | 3302.6206 | 3328.285 |
| 4409.1599 | 4400.38 | 4417.94 |
| 4466.5671 | 4453.3297 | 4479.805 |
| 4715.9166 | 4700.9233 | 4730.91 |
| 4790.6135 | 4764.6789 | 4816.548 |
| 4862.7438 | 4846.8049 | 4878.683 |
| 5740.33 | 5689.9468 | 5790.713 |
| 5851.6323 | 5796.3864 | 5906.878 |
| 5945.9151 | 5914.4425 | 5977.388 |
| 6291.0333 | 6276.175 | 6305.892 |
| 6436.5097 | 6410.7103 | 6462.309 |
| 6531.4679 | 6517.0148 | 6545.921 |
| 6647.2276 | 6606.9751 | 6687.48 |
| 6835.523 | 6823.2312 | 6847.815 |
| 6859.0262 | 6849.9761 | 6868.076 |
| 6887.3988 | 6871.2103 | 6903.587 |
| 6942.638 | 6907.3833 | 6977.893 |
| 7044.8902 | 7019.7662 | 7070.014 |
| 7195.2294 | 7176.9942 | 7213.465 |
| 7388.9278 | 7374.8799 | 7402.976 |
| 7567.903 | 7548.4521 | 7587.354 |
| 7663.6716 | 7641.9244 | 7685.419 |
| 7765.1134 | 7750.9304 | 7779.296 |
| 7940.7116 | 7914.2368 | 7967.187 |
| 8019.8659 | 7975.8313 | 8063.901 |
| 8222.2092 | 8194.6538 | 8249.765 |
| 8582.8611 | 8556.6564 | 8609.066 |
| 8633.3793 | 8615.0091 | 8651.75 |
| 8696.8649 | 8673.0916 | 8720.638 |
| 8771.1565 | 8751.5705 | 8790.742 |
| 8819.6486 | 8800.1977 | 8839.1 |
| 8874.8945 | 8858.5504 | 8891.239 |
| 8934.0576 | 8900.4238 | 8967.692 |
| 9023.3426 | 9004.2969 | 9042.388 |
| 9147.2069 | 9108.5753 | 9185.839 |
| 9296.8707 | 9269.4504 | 9324.291 |
| 9359.8159 | 9331.8553 | 9387.777 |
| 9440.8613 | 9401.8245 | 9479.898 |
| 9584.3116 | 9553.2442 | 9615.379 |
| 9654.0106 | 9619.7014 | 9688.32 |
| 9731.9492 | 9696.4243 | 9767.474 |
| 9939.5604 | 9899.9833 | 9979.138 |
| 10641.5484 | 10617.64 | 10665.46 |
| 10828.7631 | 10808.2317 | 10849.29 |
| 11395.5404 | 11375.4141 | 11415.67 |
| 11440.1153 | 11427.013 | 11453.22 |
| 11512.9211 | 11464.564 | 11561.28 |
| 11699.0553 | 11597.2083 | 11800.9 |
| 11884.9193 | 11831.2943 | 11938.54 |
| 12112.5217 | 12062.4086 | 12162.63 |
| 12449.5353 | 12424.2762 | 12474.79 |
| 12577.8361 | 12557.5686 | 12598.1 |
| 12615.0568 | 12600.6529 | 12629.46 |
| 12727.1157 | 12712.9328 | 12741.3 |
| 12864.8928 | 12838.1478 | 12891.64 |
| 13125.0484 | 13107.6237 | 13142.47 |
| 13312.3983 | 13293.3526 | 13331.44 |
| 13577.2816 | 13556.615 | 13597.95 |
| 13749.638 | 13693.4466 | 13805.83 |
| 13883.9032 | 13816.0952 | 13951.71 |
| 13982.3733 | 13959.5455 | 14005.2 |
| 14048.2902 | 14021.0049 | 14075.58 |
| 14096.9174 | 14079.0874 | 14114.75 |
| 14156.3507 | 14130.146 | 14182.56 |
| 14484.7195 | 14462.432 | 14507.01 |
| 14777.5634 | 14759.4632 | 14795.66 |
| 17268.0853 | 17235.6355 | 17300.54 |
| 17401.8418 | 17364.907 | 17438.78 |
| 17607.8848 | 17577.5456 | 17638.22 |
| 18634.4067 | 18591.1403 | 18677.67 |
| 21071.3078 | 21030.6796 | 21111.94 |
| 22316.6349 | 22129.9002 | 22503.37 |
| 23220.6291 | 22951.4507 | 23489.81 |

Example 3 Appendix C

Initial Class Labels for First Stage of Classifier Development

| Sample ID | Class Label |
| --- | --- |
| 36HSR | Early |
| 38HSR | Early |
| 39HSR | Early |
| 40HSR | Early |
| 45HSR | Early |
| 51HSR | Early |
| 56HSR | Early |
| 63HSR | Early |
| 68HSR | Early |
| ICB_03 | Early |
| ICB_06 | Early |
| ICB_10 | Early |
| ICB_12 | Early |
| ICB_13 | Early |
| ICB_22 | Early |
| ICB_26 | Early |

| Sample ID | Class Label |
|---|---|
| ICB_34 | Early |
| ICB_38 | Early |
| ICB_40 | Early |
| ICB_43 | Early |
| ICB_45 | Early |
| ICB_60 | Early |
| ICB_63 | Early |
| 10HSR | Late |
| 11HSR | Late |
| 12HSR | Late |
| 13HSR | Late |
| 14HSR | Late |
| 17HSR | Late |
| 18HSR | Late |
| 19HSR | Late |
| 1HSR | Late |
| 20HSR | Late |
| 21HSR | Late |
| 22HSR | Late |
| 2HSR | Late |
| 4HSR | Late |
| 7HSR | Late |
| 8HSR | Late |
| ICB_05 | Late |
| ICB_28 | Late |
| ICB_31 | Late |
| ICB_41 | Late |
| ICB_57 | Late |
| ICB_61 | Late |
| ICB_64 | Late |

Example 3 Appendix D

Noise Type and Noise Strength for VS2.0 Features

| m/Z Center of Feature | Noise Type | Noise Strength |
|---|---|---|
| 3218.7386 | additive | 0.449589 |
| 3315.4528 | additive | 0.705299 |
| 4409.1599 | additive | 0.372679 |
| 4466.5671 | additive | 0.558918 |
| 4715.9166 | multiplicative | 0.215793 |
| 4790.6135 | additive | 0.871467 |
| 4862.7438 | multiplicative | 0.224417 |
| 5740.33 | multiplicative | 0.219152 |
| 5851.6323 | multiplicative | 0.250464 |
| 5945.9151 | multiplicative | 0.671156 |
| 6291.0333 | additive | 0.204162 |
| 6436.5097 | additive | 1.674129 |
| 6531.4679 | additive | 0.19534 |
| 6647.2276 | additive | 3.511696 |
| 6835.523 | additive | 0.369546 |
| 6859.0262 | additive | 0.216011 |
| 6887.3988 | additive | 0.449448 |
| 6942.638 | additive | 1.17939 |
| 7044.8902 | additive | 0.435487 |
| 7195.2294 | additive | 0.222608 |
| 7388.9278 | additive | 0.163982 |
| 7567.903 | multiplicative | 0.156163 |
| 7663.6716 | multiplicative | 0.195681 |
| 7765.1134 | additive | 0.319943 |
| 7940.7116 | additive | 0.419978 |
| 8019.8659 | additive | 0.356489 |
| 8222.2092 | additive | 0.431253 |
| 8582.8611 | additive | 0.347085 |
| 8633.3793 | additive | 0.268113 |
| 8696.8649 | multiplicative | 0.274013 |
| 8771.1565 | additive | 0.692564 |
| 8819.6486 | multiplicative | 0.38203 |
| 8874.8945 | additive | 0.514021 |
| 8934.0576 | multiplicative | 0.29018 |
| 9023.3426 | additive | 0.416469 |
| 9147.2069 | multiplicative | 0.233822 |
| 9296.8707 | multiplicative | 2.007367 |
| 9359.8159 | multiplicative | 0.15884 |
| 9440.8613 | multiplicative | 0.155807 |
| 9584.3116 | multiplicative | 0.280165 |
| 9654.0106 | multiplicative | 0.200748 |
| 9731.9492 | multiplicative | 0.200652 |
| 9939.5604 | multiplicative | 0.240092 |
| 10641.5484 | additive | 0.246795 |
| 10828.7631 | additive | 0.374312 |
| 11395.5404 | additive | 0.511211 |
| 11440.1153 | multiplicative | 0.240577 |
| 11512.9211 | multiplicative | 0.316491 |
| 11699.0553 | multiplicative | 0.402835 |
| 11884.9193 | multiplicative | 0.190473 |
| 12112.5217 | multiplicative | 1.367853 |
| 12449.5353 | multiplicative | 2.019671 |
| 12577.8361 | multiplicative | 0.163202 |
| 12615.0568 | multiplicative | 0.50929 |
| 12727.1157 | multiplicative | 0.212812 |
| 12864.8928 | multiplicative | 0.116047 |
| 13125.0484 | additive | 0.143445 |
| 13312.3983 | additive | 0.144914 |
| 13577.2816 | additive | 0.136992 |
| 13749.638 | additive | 1.208693 |
| 13883.9032 | additive | 2.503822 |
| 13982.3733 | additive | 0.517253 |
| 14048.2902 | additive | 1.393395 |
| 14096.9174 | additive | 0.595363 |
| 14156.3507 | additive | 0.837603 |
| 14484.7195 | additive | 0.22863 |
| 14777.5634 | additive | 0.091024 |
| 17268.0853 | additive | 0.353217 |
| 17401.8418 | additive | 0.574893 |
| 17607.8848 | additive | 0.142937 |
| 18634.4067 | additive | 0.133441 |
| 21071.3078 | additive | 0.133543 |
| 22316.6349 | additive | 1.392056 |
| 23220.6291 | additive | 0.776561 |

Example 3 Appendix E

VS2.0 Classifications of Development Set Samples

| Sample ID | OverallClassification | VS1.0 Classification |
|---|---|---|
| ICA_1 | Late | Good |
| ICA_10 | Late | Good |
| ICA_11 | Early | Good |
| ICA_12 | Early | Good |
| ICA_13 | Late | Good |
| ICA_14 | Late | Good |
| ICA_15 | Late | Good |
| ICA_17 | Late | Good |
| ICA_18 | Early | Good |
| ICA_19 | Late | Good |
| ICA_2 | Late | Good |
| ICA_20 | Late | Good |
| ICA_21 | Late | Good |
| ICA_22 | Early | Good |
| ICA_23 | Early | Good |
| ICA_24 | Early | Poor |
| ICA_25 | Early | Good |
| ICA_26 | Early | Good |
| ICA_27 | Late | Good |
| ICA_28 | Early | Good |
| ICA_29 | Early | Good |
| ICA_3 | Early | Poor |
| ICA_30 | Early | Poor |
| ICA_31 | Early | Good |
| ICA_32 | Early | Good |
| ICA_34 | Late | Good |

| Sample ID | OverallClassification | VS1.0 Classification |
|---|---|---|
| ICA_35 | Early | Good |
| ICA_36 | Late | Good |
| ICA_38 | Early | Good |
| ICA_39 | Early | Good |
| ICA_4 | Late | Good |
| ICA_40 | Early | Good |
| ICA_41 | Late | Good |
| ICA_42 | Early | Good |
| ICA_43 | Early | Poor |
| ICA_44 | Late | Good |
| ICA_45 | Early | Good |
| ICA_46 | Early | Good |
| ICA_47 | Early | Poor |
| ICA_48 | Late | Good |
| ICA_49 | Early | Poor |
| ICA_5 | Late | Good |
| ICA_50 | Late | Good |
| ICA_51 | Late | Good |
| ICA_52 | Early | Poor |
| ICA_54 | Early | Poor |
| ICA_55 | Late | Good |
| ICA_56 | Early | Good |
| ICA_57 | Early | Poor |
| ICA_58 | Early | Poor |
| ICA_59 | Early | Poor |
| ICA_6 | Early | Poor |
| ICA_60 | Early | Poor |
| ICA_61 | Early | Poor |
| ICA_63 | Early | Good |
| ICA_64 | Early | Poor |
| ICA_65 | Early | Poor |
| ICA_67 | Early | Good |
| ICA_68 | Late | Good |
| ICA_69 | Early | Poor |
| ICA_7 | Late | Good |
| ICA_70 | Early | Good |
| ICA_8 | Late | Good |
| ICB_1 | Early | Poor |
| ICB_10 | Early | Good |
| ICB_11 | Early | Poor |
| ICB_12 | Late | Good |
| ICB_13 | Early | Good |
| ICB_14 | Early | Good |
| ICB_15 | Early | Good |
| ICB_16 | Late | Good |
| ICB_17 | Late | Good |
| ICB_18 | Early | Poor |
| ICB_19 | Early | Poor |
| ICB_2 | Late | Good |
| ICB_20 | Early | Poor |
| ICB_21 | Early | Good |
| ICB_22 | Late | Good |
| ICB_23 | Early | Poor |
| ICB_24 | Early | Poor |
| ICB_25 | Early | Poor |
| ICB_26 | Early | Good |
| ICB_27 | Early | Poor |
| ICB_28 | Late | Good |
| ICB_29 | Early | Poor |
| ICB_3 | Late | Good |
| ICB_30 | Early | Poor |
| ICB_31 | Late | Good |
| ICB_32 | Early | Poor |
| ICB_33 | Early | Poor |
| ICB_34 | Early | Good |
| ICB_35 | Early | Poor |
| ICB_36 | Late | Good |
| ICB_37 | Early | Poor |
| ICB_38 | Late | Good |
| ICB_39 | Early | Good |
| ICB_4 | Early | Poor |
| ICB_40 | Late | Good |
| ICB_41 | Late | Good |
| ICB_42 | Early | Poor |
| ICB_43 | Early | Good |
| ICB_44 | Early | Poor |
| ICB_45 | Early | Good |
| ICB_46 | Early | Poor |
| ICB_47 | Late | Good |
| ICB_48 | Early | Good |
| ICB_49 | Late | Good |
| ICB_5 | Late | Good |
| ICB_50 | Late | Good |
| ICB_51 | Early | Poor |
| ICB_52 | Late | Good |
| ICB_53 | Early | Poor |
| ICB_54 | Early | Good |
| ICB_55 | Early | Poor |
| ICB_56 | Early | Poor |
| ICB_57 | Late | Good |
| ICB_58 | Early | Poor |
| ICB_59 | Early | Poor |
| ICB_6 | Early | Good |
| ICB_60 | Early | Good |
| ICB_61 | Early | Good |
| ICB_62 | Early | Good |
| ICB_63 | Early | Good |
| ICB_64 | Late | Good |
| ICB_65 | Early | Good |
| ICB_66 | Early | Poor |
| ICB_67 | Late | Good |
| ICB_8 | Early | Poor |
| ICB_9 | Late | Good |
| ICC_1 | Early | Poor |
| ICC_10 | Early | Good |
| ICC_11 | Late | Good |
| ICC_12 | Early | Poor |
| ICC_13 | Early | Poor |
| ICC_14 | Early | Good |
| ICC_15 | Early | Poor |
| ICC_16 | Early | Poor |
| ICC_17 | Late | Good |
| ICC_18 | Early | Poor |
| ICC_19 | Early | Good |
| ICC_2 | Early | Poor |
| ICC_20 | Early | Poor |
| ICC_21 | Late | Good |
| ICC_22 | Early | Good |
| ICC_23 | Late | Good |
| ICC_24 | Late | Good |
| ICC_25 | Early | Good |
| ICC_26 | Early | Good |
| ICC_27 | Late | Good |
| ICC_28 | Late | Good |
| ICC_29 | Late | Good |
| ICC_3 | Early | Poor |
| ICC_30 | Early | Good |
| ICC_31 | Early | Good |
| ICC_32 | Early | Poor |
| ICC_4 | Early | Good |
| ICC_5 | Early | Good |
| ICC_6 | Early | Poor |
| ICC_7 | Early | Good |
| ICC_8 | Early | Poor |
| ICC_9 | Early | Good |

Example 3 Appendix F

VS2.0 Classifications of Development Set Samples
Across Three Runs

| Sample ID | Development Run Classification | Development Run Noise Effect Estimator | Feb_3 Classification | Feb_3 Noise Effect Estimator | Feb_25 Classification | Feb_25 Noise quantifier |
|---|---|---|---|---|---|---|
| ICA_1 | Late | 0.2508903 | Late | 0.466734822 | Unknown | 1.25354 |
| ICA_10 | Late | 0.3138037 | Unknown | 1.964538835 | Unknown | 3.23176 |
| ICA_11 | Early | 0.080601 | Early | 0.31109509 | Early | 0.18127 |
| ICA_12 | Early | 0.0355124 | Early | 0.00909397 | Early | 0.1501 |
| ICA_13 | Late | 0.0047174 | Late | 0.030926878 | Late | 0.08849 |
| ICA_14 | Unknown | 2.7555361 | Unknown | 6.009376135 | Unknown | 0.57061 |
| ICA_15 | Late | 0.0149085 | Late | 0.187318654 | Late | 0.08098 |
| ICA_17 | Late | 0.0451973 | Late | 0.130183945 | Late | 0.10486 |
| ICA_18 | Early | 0.3983651 | Early | 0.134071541 | Early | 0.2023 |
| ICA_19 | Late | 0.0826776 | Late | 0.027922277 | Late | 0.03699 |
| ICA_2 | Late | 0.0115269 | Late | 0.014803894 | Late | 0.01478 |
| ICA_20 | Late | 0.2883118 | Late | 0.468349356 | Unknown | 1.55056 |
| ICA_21 | Late | 0.3249368 | Late | 0.197541409 | Late | 0.42881 |
| ICA_22 | Early | 0.4547106 | Unknown | 408.6471898 | Unknown | 10.2749 |
| ICA_23 | Early | 0.0748141 | Unknown | 1.064878786 | | |
| ICA_24 | Unknown | 0.5213397 | Early | 0.273862348 | | |
| ICA_25 | Unknown | 0.5367448 | Early | 0.576202188 | Unknown | 2.14736 |
| ICA_26 | Unknown | 1.4825573 | Unknown | 1.176456598 | Unknown | 1.14433 |
| ICA_27 | Late | 0.4851147 | Unknown | 0.823851604 | Unknown | 0.54047 |
| ICA_28 | Early | 0.024537 | Early | 0.041470212 | Early | 0.04415 |
| ICA_29 | Early | 0.0684268 | Early | 0.199645029 | Early | 0.23878 |
| ICA_3 | Early | 0.0449748 | Early | 0 | | |
| ICA_30 | Early | 0.1134967 | Early | 0 | | |
| ICA_31 | Unknown | 1.1973862 | Unknown | 2.017268589 | Unknown | 7.40837 |
| ICA_32 | Unknown | 0.9744799 | Unknown | 3.705512439 | Unknown | 1.88644 |
| ICA_34 | Late | 0.0513075 | Late | 0.075731492 | Late | 0.15651 |
| ICA_35 | Early | 0.2933299 | Early | 0.191894212 | Early | 0.0942 |
| ICA_36 | Late | 0.0405301 | Late | 0.207008265 | | |
| ICA_38 | Unknown | 0.6299707 | Early | 0.286152473 | Unknown | 1.39855 |
| ICA_39 | Unknown | 0.6493858 | Unknown | 2.07717748 | Unknown | 1.02573 |
| ICA_4 | Late | 0 | Late | 0.038223058 | Late | 0.06442 |
| ICA_40 | Early | 0.1460363 | Unknown | 2.460497465 | Early | 0.11424 |
| ICA_41 | Late | 0.359934 | Late | 0.401264716 | Unknown | 0.757 |
| ICA_42 | Unknown | 2.2944611 | Early | 0.123948659 | Early | 0.27961 |
| ICA_43 | Early | 0.0967663 | Early | 0.000632487 | | |
| ICA_44 | Unknown | 1.6734598 | Early | 0.169833656 | Early | 0.40807 |
| ICA_45 | Unknown | 1.0538265 | Unknown | 0.584840142 | Early | 0.21289 |
| ICA_46 | Early | 0.4287061 | Unknown | 2.926113519 | Unknown | 0.6906 |
| ICA_47 | Early | 0.0535227 | Early | 0 | | |
| ICA_48 | Late | 0.4357615 | Unknown | 2.0349327 | Unknown | 2.07714 |
| ICA_49 | Early | 0 | Early | 0 | | |
| ICA_5 | Unknown | 0.9192309 | Unknown | 0.653490123 | Late | 0.21708 |
| ICA_50 | Unknown | 2.6894001 | Early | 0.158682214 | Unknown | 0.51338 |
| ICA_51 | Late | 0.1653643 | Late | 0.31185332 | Unknown | 0.9165 |
| ICA_52 | Early | 0.0045497 | Early | 0 | | |
| ICA_54 | Early | 0.0918534 | Early | 0 | | |
| ICA_55 | Late | 0.009786 | Unknown | 0.556007152 | Unknown | 1.96082 |
| ICA_56 | Early | 0.0022435 | Early | 0.050034194 | Early | 0.0091 |
| ICA_57 | Early | 0.0050177 | Early | 0.000632487 | | |
| ICA_58 | Early | 0 | Early | 0 | | |
| ICA_59 | Early | 0.0020317 | Early | 0.001887201 | | |
| ICA_6 | Early | 0.0010887 | Early | 0 | | |
| ICA_60 | Early | 0 | Early | 0 | | |
| ICA_61 | Early | 0 | Early | 0 | | |
| ICA_63 | Early | 0.0304895 | Early | 0.046816893 | Early | 0.14536 |
| ICA_64 | Early | 0 | Early | 0 | | |
| ICA_65 | Early | 0 | Early | 0 | | |
| ICA_67 | Unknown | 0.7938756 | Unknown | 0.826523764 | Unknown | 0.60441 |
| ICA_68 | Late | 0.2370179 | Unknown | 2.282512088 | Unknown | 2.00963 |
| ICA_69 | Early | 0.0061302 | Early | 0.014126042 | | |
| ICA_7 | Late | 0.2874263 | Late | 0.092535875 | Late | 0.17229 |
| ICA_70 | Unknown | 0.8459228 | Unknown | 0.592744714 | Early | 0.19042 |
| ICA_8 | Late | 0.3185725 | Unknown | 0.524389074 | Unknown | 1.06012 |
| ICB_1 | Early | 0.001642 | Early | 0 | | |
| ICB_10 | Early | 0.1244703 | Early | 0.071776831 | Early | 0.04976 |
| ICB_11 | Early | 0 | Early | 0 | | |
| ICB_12 | Late | 0.4010251 | Unknown | 3.819985778 | Unknown | 2.46467 |
| ICB_13 | Early | 0.0335419 | Early | 0.239284331 | Early | 0.20115 |
| ICB_14 | Unknown | 0.7794731 | Unknown | 1.064463653 | Early | 0.20933 |

-continued

| Sample ID | Development Run Classification | Development Run Noise Effect Estimator | Feb_3 Classification | Feb_3 Noise Effect Estimator | Feb_25 Classification | Feb_25 Noise quantifier |
|---|---|---|---|---|---|---|
| ICB_15 | Unknown | 1.402295 | Early | 0.005996916 | Early | 0.05784 |
| ICB_16 | Late | 0.49193 | Unknown | 3.18288305 | | |
| ICB_17 | Unknown | 15.495518 | Unknown | 2.770598757 | Unknown | 0.75083 |
| ICB_18 | Early | 0.0104891 | Early | 0 | | |
| ICB_19 | Early | 0.0044287 | Early | 0 | | |
| ICB_2 | Unknown | 1.8319861 | Unknown | 0.574145865 | Unknown | 1.11314 |
| ICB_20 | Early | 0.1010281 | Early | 0.001265038 | | |
| ICB_21 | Early | 0.3837118 | Early | 0.047678494 | Early | 0.42108 |
| ICB_22 | Late | 0.24719 | Unknown | 1.296687602 | Unknown | 2.0375 |
| ICB_23 | Early | 0.0080037 | Early | 0 | | |
| ICB_24 | Early | 0 | Early | 0 | | |
| ICB_25 | Early | 0.4691525 | Early | 0.374906318 | | |
| ICB_26 | Early | 0.2842823 | Unknown | 18.84274386 | Unknown | 1.65263 |
| ICB_27 | Early | 0.1090687 | Early | 0.026120232 | | |
| ICB_28 | Late | 0.0106621 | Late | 0.174473568 | Late | 0.11698 |
| ICB_29 | Early | 0.0235619 | Early | 0.009862237 | | |
| ICB_3_rerun | Late | 0.0304724 | Late | 0.067773006 | | |
| ICB_30 | Early | 0.0210381 | Early | 0.007672574 | | |
| ICB_31 | Late | 0.1671391 | Unknown | 1.269484668 | Unknown | 2.60353 |
| ICB_32 | Early | 0.0504194 | Early | 0.006513994 | | |
| ICB_33 | Early | 0.0022743 | Early | 0 | | |
| ICB_34 | Unknown | 0.7717411 | Early | 0.235015835 | Early | 0.23868 |
| ICB_35 | Early | 0.1187116 | Unknown | 0.684071314 | | |
| ICB_36 | Unknown | 0.6113689 | Early | 0.495122448 | | |
| ICB_37 | Early | 0 | Early | 0.000632487 | | |
| ICB_38 | Unknown | 0.7252647 | Late | 0.327507909 | Unknown | 7.41886 |
| ICB_39 | Early | 0.0873692 | Unknown | 0.538723703 | Unknown | 0.69525 |
| ICB_4 | Early | 0.0583902 | Early | 0 | | |
| ICB_40 | Unknown | 1.5221366 | Unknown | 1.376172237 | Unknown | 4.11934 |
| ICB_41 | Late | 0.2281209 | Unknown | 2.942393151 | | |
| ICB_42 | Early | 0.016582 | Early | 0.001265038 | | |
| ICB_43 | Early | 0.008667 | Early | 0.014663441 | Early | 0.00617 |
| ICB_44 | Early | 0.026458 | Early | 0.001253172 | | |
| ICB_45 | Early | 0.3637465 | Early | 0.19639466 | Early | 0.17223 |
| ICB_46 | Early | 0 | Early | 0 | | |
| ICB_47 | Late | 0.3112708 | Late | 0.37180672 | Unknown | 0.53511 |
| ICB_48 | Unknown | 0.6104345 | Unknown | 0.695956133 | Unknown | 1.19754 |
| ICB_49 | Unknown | 0.8091827 | Unknown | 1.921287211 | | |
| ICB_5 | Unknown | 0.5610236 | Unknown | 1.791500069 | Unknown | 19.3159 |
| ICB_50 | Unknown | 1.5210721 | Early | 0.322646083 | | |
| ICB_51 | Early | 0.2798399 | Early | 0.411311501 | | |
| ICB_52 | Late | 0.0913128 | Unknown | 0.995984435 | Late | 0.0946 |
| ICB_53 | Early | 0.0177726 | Early | 0 | | |
| ICB_54 | Unknown | 3.9796933 | Unknown | 0.729611954 | | |
| ICB_55 | Early | 0.2673627 | Early | 0.016808751 | | |
| ICB_56 | Early | 0.016083 | Early | 0.001660149 | | |
| ICB_57 | Late | 0.0495004 | Late | 0.454621578 | Unknown | 5.38489 |
| ICB_58 | Early | 0 | Early | 0 | | |
| ICB_59 | Early | 0.099419 | Early | 0 | | |
| ICB_6 | Early | 0.0926929 | Early | 0.010137147 | Early | 0.01514 |
| ICB_60 | Early | 0.024118 | Early | 0.045176626 | Early | 0.22779 |
| ICB_61 | Early | 0.0207761 | Early | 0.098978496 | Early | 0.05717 |
| ICB_62 | Early | 0.1123475 | Early | 0.038795663 | | |
| ICB_63 | Early | 0.3143604 | Unknown | 0.5577347 | Early | 0.17666 |
| ICB_64 | Late | 0.2135021 | Unknown | 0.981560369 | | |
| ICB_65 | Early | 0.4912493 | Unknown | 0.975042177 | Early | 0.48021 |
| ICB_66 | Early | 0.0471047 | Early | 0.046567508 | | |
| ICB_67 | Unknown | 0.5234719 | Early | 0.322026183 | | |
| ICB_8 | Early | 0.0052102 | Early | 0 | | |
| ICB_9 | Late | 0.1080207 | Late | 0.042361028 | Late | 0.04029 |
| ICC_1 | Early | 0.2070783 | Early | 0.085396794 | | |
| ICC_10 | Early | 0.1236901 | Early | 0.004740175 | Early | 0.01399 |
| ICC_11 | Unknown | 1.1814412 | Unknown | 2.209011682 | Unknown | 1.34544 |
| ICC_12 | Early | 0.0054516 | Early | 0 | | |
| ICC_13 | Early | 0 | Early | 0 | | |
| ICC_14 | Unknown | 0.9532531 | Early | 0.208090801 | Early | 0.40234 |
| ICC_15 | Early | 0.0046228 | Early | 0.000632487 | | |
| ICC_16 | Early | 0.0006325 | Early | 0 | | |
| ICC_17 | Unknown | 1.060111 | Unknown | 0.503778812 | Late | 0.33919 |
| ICC_18 | Early | 0.001265 | Early | 0.010079649 | | |
| ICC_19 | Early | 0.0946116 | Early | 0.034253636 | Early | 0.21303 |
| ICC_2 | Early | 0 | Early | 0 | | |
| ICC_20 | Early | 0.0392832 | Early | 0.101833857 | | |
| ICC_21 | Late | 0.1985239 | Late | 0.269895491 | Unknown | 1.26594 |

-continued

| Sample ID | Development Run Classification | Development Run Noise Effect Estimator | Feb_3 Classification | Feb_3 Noise Effect Estimator | Feb_25 Classification | Feb_25 Noise quantifier |
|---|---|---|---|---|---|---|
| ICC_22 | Early | 0.1766128 | Unknown | 1.01724785 | Unknown | 2.29042 |
| ICC_23 | Unknown | 2.3518283 | Unknown | 4.747822355 | Unknown | 36.0979 |
| ICC_24 | Late | 0.4498147 | Unknown | 1.641647487 | Late | 0.23851 |
| ICC_25 | Early | 0.2547183 | Early | 0.026712614 | Early | 0.20825 |
| ICC_26 | Early | 0.0183961 | Early | 0.177587583 | Early | 0.06516 |
| ICC_27 | Unknown | 2.6560691 | Unknown | 0.894522603 | Unknown | 4.03214 |
| ICC_28 | Unknown | 5.162227 | Unknown | 1.585391499 | Unknown | 1.17993 |
| ICC_29 | Late | 0.0907799 | Late | 0.134559673 | Late | 0.30603 |
| ICC_3 | Early | 0.0006325 | Early | 0 | | |
| ICC_30 | Early | 0.0374486 | Early | 0.025356686 | Early | 0.03447 |
| ICC_31 | Early | 0.2820449 | Early | 0.145453279 | Early | 0.23148 |
| ICC_32 | Early | 0.0045497 | Early | 0 | | |
| ICC_4 | Unknown | 2.6580968 | Unknown | 0.635164246 | Unknown | 5.92408 |
| ICC_5 | Early | 0.1713111 | Unknown | 0.519211365 | Unknown | 0.51357 |
| ICC_6 | Early | 0.0193609 | Early | 0 | | |
| ICC_7 | Early | 0.0008917 | Early | 0 | Early | 0.0272 |
| ICC_8 | Early | 0.0873546 | Early | 0 | | |
| ICC_9 | Early | 0.0085559 | Early | 0.002577784 | Early | 0.00956 |

Example 3 Appendix G

VS2.0 Classifications Returned for PROSE Samples

| Blinded ID | VS2.0 CLASSIFICATION | PROSE Sample # |
|---|---|---|
| 3001 | Unknown | 01_024_1 |
| 3009 | Early | 11_046_1 |
| 3023 | Unknown | 01_055_1 |
| 3038 | Unknown | 16_005_1 |
| 3053 | Early | 04_001_1 |
| 3058 | Unknown | 10_002_1 |
| 3065 | Early | 16_013_1 |
| 3098 | Early | 11_055_1 possible repeat |
| 3099 | Unknown | 06_014_1 |
| 3116 | Early | 01_059_1 |
| 3170 | Unknown | 01_013_1 |
| 3194 | Late | 10_005_1 |
| 3200 | Late | 01_074_1 |
| 3204 | Early | 01_010_1 |
| 3214 | Sample not available for MS generation | 11_043_1 |
| 3246 | Early | 16_012_1 |
| 3262 | Early | 01_039_1 |
| 3306 | Early | 01_044_1 |
| 3336 | Late | 16_017_1 |
| 3344 | Late | 06_012_1 |
| 3382 | Early | 01_075_1 |
| 3402 | Early | 06_043_1 |
| 3410 | Early | 06_002_1 |
| 3412 | Unknown | 11_050_1 |
| 3413 | Early | 01_008_1 |
| 3421 | Early | 06_010_1 |
| 3423 | Early | 01_066_1 |
| 3435 | Unknown | 11_044_1 |
| 3437 | Early | 11_003_1 |
| 3438 | Unknown | 08_001_1 |
| 3444 | Early | 11_047_1 |
| 3470 | Late | 01_021_1 |
| 3481 | Unknown | 01_025_1 |
| 3508 | Early | 01_001_1 |
| 3521 | Early | 16_006_1 |
| 3526 | Early | 01_034_1 |
| 3535 | Early | 01_062_1 |
| 3553 | Unknown | 01_082_1 |
| 3563 | Early | 06_040_1 |
| 3592 | Early | 11_005_1 |
| 3600 | Unknown | 14_001_1 |
| 3609 | Early | 14_012_1 |
| 3646 | Early | 11_030_1 |
| 3655 | Early | 07_012_1 |
| 3670 | Unknown | 06_030_1 |
| 3678 | Early | 01_052_1 |
| 3686 | Unknown | 01_080_1 |
| 3698 | Early | 01_029_1 |
| 3701 | Early | 01_060_1 |
| 3704 | Unknown | 01_049_1 |
| 3727 | Early | 12_007_1 |
| 3739 | Early | 11_008_1 |
| 3763 | Unknown | 01_061_1 |
| 3764 | Early | 06_020_1 |
| 3767 | Unknown | 12_013_1 |
| 3780 | Early | 12_009_1 |
| 3792 | Early | 12_003_1 |
| 3798 | Unknown | 01_089_1 |
| 3801 | Early | 07_011_1 |
| 3806 | Unknown | 04_013_1 |
| 3821 | Early | 16_016_1 |
| 3850 | Early | 11_056_1 |
| 3854 | Early | 14_013_1 |
| 3874 | Early | 01_093_1 |
| 3882 | Unknown | 12_006_1 |
| 3903 | Early | 07_007_1 |
| 3920 | Early | 11_026_1 |
| 3943 | Early | 11_012_1 |
| 3945 | Early | 11_033_1 |
| 3953 | Early | 11_042_1 |
| 3955 | Unknown | 04_005_1 |
| 3962 | Unknown | 12_013_1 second sample |
| 3969 | Unknown | 14_006_1 |
| 3973 | Early | 13_005_1 |
| 3978 | Unknown | 03_001_1 |
| 3993 | Unknown | 02_005_1 |
| 4001 | Early | 06_016_1 |
| 4009 | Unknown | 16_009_1 |
| 4014 | Late | 04_003_1 |
| 4034 | Early | 12_008_1 |
| 4042 | Early | 06_013_1 |
| 4049 | Unknown | 06_009_1 |
| 4053 | Early | 01_007_1 |
| 4055 | Early | 11_039_1 |
| 4062 | Unknown | 12_001_1 |
| 4076 | Late | 01_035_1 |
| 4083 | Early | 11_015_1 |
| 4120 | Early | 11_053_1 |
| 4136 | Late | 07_008_1 |
| 4161 | Unknown | 16_011_1 |
| 4200 | Unknown | 06_022_1 |

-continued

| Blinded ID | VS2.0 CLASSIFICATION | PROSE Sample # |
|---|---|---|
| 4202 | Unknown | 07_006_1 |
| 4227 | Unknown | 01_030_1 |
| 4308 | Late | 01_067_1 |
| 4331 | Sample not available for MS generation | 01_040_1 repeat (original sample # not listed on pdf document) |
| 4345 | Late | 11_024_1 |
| 4349 | Unknown | 13_004_1 |
| 4353 | Late | 11_051_1 |
| 4364 | Early | 11_029_1 |
| 4381 | Early | 01_015_1 |
| 4385 | Early | 01_083_1 |
| 4419 | Unknown | 11_001_1 |
| 4426 | Early | 01_069_1 |
| 4431 | Unknown | 01_019_1 |
| 4445 | Early | 11_041_1 |
| 4446 | Unknown | 01_032_1 |
| 4455 | Early | 11_028_1 |
| 4462 | Early | 01_090_1 |
| 4499 | Early | 02_002_1 |
| 4504 | Early | 01_073_1 |
| 4505 | Unknown | 16_015_1 |
| 4509 | Early | 11_016_1 |
| 4510 | Late | 01_033_1 |
| 4515 | Early | 12_002_1 |
| 4540 | Early | 11_034_1 |
| 4562 | Early | 01_014_1 |
| 4564 | Early | 04_002_1 |
| 4607 | Unknown | 01_047_1 |
| 4618 | Early | 06_042_1 |
| 4634 | Early | 01_053_1 |
| 4667 | Unknown | 13_003_1 |
| 4683 | Early | 14_010_1 |
| 4694 | Late | 06_024_1 |
| 4697 | Early | 06_038_1 |
| 4699 | Early | 11_037_1 |
| 4713 | Late | 01_016_1 |
| 4730 | Early | 01_028_1 |
| 4753 | Early | 06_015_1 |
| 4770 | Early | 06_034_1 |
| 4780 | Late | 06_018_1 |
| 4783 | Late | 01_027_1 |
| 4786 | Unknown | 04_010_1 |
| 4803 | Early | 01_026_1 |
| 4826 | Early | 01_006_1 |
| 4851 | Early | 01_086_1 |
| 4873 | Unknown | 12_012_1 |
| 4876 | Early | 11_022_1 |
| 4880 | Early | 01_077_1 |
| 4900 | Early | 01_020_1 |
| 4910 | Early | 06_031_1 |
| 4936 | Early | 01_088_1 |
| 4961 | Late | 01_072_1 |
| 4976 | Early | 01_037_1 |
| 4986 | Late | 15_002_1 |
| 5007 | Unknown | 01_079_1 |
| 5072 | Unknown | 11_035_1 |
| 5079 | Early | 03_004_1 |
| 5090 | Early | 11_049_1 |
| 5091 | Early | 01_087_1 |
| 5101 | Unknown | 01_063_1 |
| 5134 | Early | 12_010_1 |
| 5158 | Late | 07_014_1 |
| 5195 | Early | 01_080_1 second sample |
| 5196 | Early | 16_014_1 |
| 5214 | Unknown | 14_009_1 |
| 5228 | Unknown | 11_036_1 |
| 5239 | Early | 04_009_1 |
| 5250 | Late | 11_021_1 |
| 5254 | Early | 06_026_1 |
| 5292 | Early | 11_004_1 |
| 5295 | Early | 07_005_1 |
| 5307 | Early | 06_025_1 |
| 5330 | Late | 11_045_1 |
| 5336 | Unknown | 10_003_1 |
| 5351 | Early | 06_033_1 |
| 5352 | Late | 16_010_1 |
| 5358 | Unknown | 13_001_1 |
| 5362 | Late | 04_004_1 |
| 5374 | Unknown | 02_003_1 |
| 5391 | Early | 01_064_1 |
| 5395 | Early | 06_032_1 |
| 5401 | Late | 01_092_1 |
| 5411 | Early | 13_002_1 |
| 5424 | Late | 01_043_1 |
| 5431 | Unknown | 02_004_1 |
| 5440 | Early | 06_029_1 |
| 5443 | Unknown | 12_011_1 |
| 5444 | Early | 11_006_1 |
| 5447 | Unknown | 01_003_1 |
| 5448 | Unknown | 04_006_1 |
| 5456 | Early | 14_011_1 |
| 5466 | Early | 14_004_1 |
| 5497 | Unknown | 16_003_1 |
| 5505 | Early | 01_002_1 |
| 5507 | Early | 12_005_1 |
| 5512 | Late | 01_070_1 |
| 5567 | Unknown | 02_001_1 |
| 5573 | Early | 01_022_1 |
| 5583 | Early | 04_012_1 |
| 5587 | Early | 12_004_1 |
| 5594 | Early | 06_041_1 |
| 5638 | Early | 11_023_1 |
| 5658 | Early | 01_011_1 |
| 5663 | Early | 01_094_1 |
| 5671 | Early | 11_031_1 |
| 5672 | Early | 01_056_1 |
| 5673 | Early | 01_004_1 |
| 5680 | Late | 14_003_1 |
| 5713 | Early | 01_009_1 |
| 5714 | Late | 06_005_1 |
| 5721 | Unknown | 01_071_1 |
| 5724 | Early | 08_002_1 |
| 5725 | Unknown | 06_019_1 |
| 5747 | Early | 01_065_1 |
| 5755 | Early | 01_042_1 |
| 5767 | Unknown | 07_004_1 |
| 5791 | Early | 06_037_1 |
| 5801 | Late | 11_018_1 |
| 5813 | Early | 11_027_1 |
| 5820 | Late | 01_018_1 |
| 5842 | Late | 03_005_1 |
| 5847 | Unknown | 11_054_1 |
| 5869 | Early | 14_005_1 |
| 5874 | Early | 15_001_1 |
| 5910 | Unknown | 01_091_1 |
| 5911 | Early | 06_035_1 |
| 5913 | Early | 03_002_1 |
| 5935 | Early | 16_018_1 |
| 5963 | Early | 06_039_1 |
| 5970 | Late | 01_054_1 |
| 5975 | Early | 01_046_1 |
| 5976 | Early | 01_085_1 |
| 5997 | Unknown | 14_002_1 |
| 6048 | Early | 01_017_1 |
| 6056 | Unknown | 16_007_1 |
| 6082 | Early | 11_014_1 |
| 6093 | Early | 07_001_1 |
| 6098 | Late | 11_017_1 |
| 6105 | Unknown | 16_002_1 |
| 6122 | Early | 06_010_1 second sample |
| 6130 | Early | 14_007_1 |
| 6140 | Unknown | 07_003_1 |
| 6156 | Late | 11_011_1 |
| 6161 | Early | 01_068_1 |
| 6182 | Early | 11_020_1 |
| 6193 | Unknown | 16_008_1 |
| 6203 | Early | 11_013_1 |

-continued

| Blinded ID | VS2.0 CLASSIFICATION | PROSE Sample # |
|---|---|---|
| 6235 | Unknown | 11_010_1 |
| 6260 | Early | 01_045_1 |
| 6270 | Early | 11_052_1 |
| 6278 | Early | 06_008_1 |
| 6281 | Early | 04_008_1 |
| 6282 | Unknown | 06_022_1 |
| 6295 | Early | 11_009_1 |
| 6296 | Early | 01_041_1 |
| 6297 | Unknown | 01_081_1 |
| 6299 | Early | 14_014_1 |
| 6321 | Early | 11_057_1 |
| 6336 | Late | 01_023_1 |
| 6349 | Late | 10_001_1 |
| 6361 | Unknown | 03_003_1 |
| 6390 | Early | 01_078_1 |
| 6398 | Unknown | 06_001_1 |
| 6419 | Late | 01_044_1 second sample |
| 6424 | Early | 06_023_1 |
| 6438 | Unknown | 16_001_1 |
| 6439 | Early | 01_036_1 |
| 6442 | Early | 10_004_1 |
| 6476 | Early | 01_084_1 |
| 6487 | Sample not available for MS generation | 11_048_1 |
| 6492 | Late | 01_057_1 |
| 6572 | Unknown | 13_006_1 |
| 6585 | Early | 01_076_1 |
| 6604 | Early | 11_002_1 |
| 6622 | Early | 01_031_1 |
| 6625 | Early | 06_011_1 |
| 6626 | Early | 06_003_1 |
| 6667 | Unknown | 11_025_1 |
| 6712 | Early | 01_038_1 |
| 6718 | Early | 07_013_1 |
| 6729 | Early | 06_036_1 |
| 6737 | Early | 06_006_1 |
| 6741 | Early | 16_004_1 |
| 6752 | Early | 11_019_1 |
| 6761 | Late | 06_027_1 |
| 6770 | Early | 11_007_1 |
| 6795 | Unknown | 11_038_1 |
| 6797 | Early | 01_058_1 |
| 6824 | Unknown | 04_007_1 |
| 6827 | Early | 06_007_1 |
| 6847 | Early | 04_011_1 |
| 6854 | Early | 07_002_1 |
| 6886 | Unknown | 01_012_1 |
| 6887 | Late | 01_051_1 |
| 6932 | Early | 01_005_1 |
| 6939 | Late | 14_008_1 |
| 6947 | Early | 11_032_1 |
| 6977 | Early | 07_009_1 |
| 6981 | Unknown | 06_028_1 |
| 6982 | Early | 13_007_1 |
| 6992 | Late | 11_040_1 |
| 6998 | Unknown | 06_017_1 |

Example 3 Appendix H

Details of Instruments for Spectral Acquisition

| Run | Dates | Serial Number | Qualification Date |
|---|---|---|---|
| 140131_ItalianABC | Feb. 3, 2014-Feb. 4, 2014 | 260 | Jan. 30, 2014 NRS Jan. 27, 2014 RuO |
| 140225_ItalianABC | Feb. 25, 2014 | 260 | Feb. 25, 2014 NRS |
| 140130_Furb_PROSE*[2] | Jan. 30, 2014-Jan. 31, 2014 | 260 | Jan. 30, 2014 NRS |
| 140115_PROSE | Jan. 15, 2014-Jan. 17, 2014 | 258 | Dec. 11, 2013* |
| 131118_ItalianABC | Nov. 18, 2013-Nov. 19, 2013 | 258 | Nov. 12, 2013 RuO |

*This was a quick concordance check two samples had a spot fail to acquire, but if you dropped these two samples it was concordant.
*[2]This run was done on the same plate as the 140115_PROSE run from instrument 258

We claim:

1. A method for generating a classifier to classify a sample in accordance with physical attributes of the sample, comprising the steps of:
  a) obtaining physical measurement data for classification from a plurality of samples, the physical measurement data for each of the samples comprising a multitude of feature values;
  b) assigning a class label to each of the samples;
  with a programmed computer:
  c) constructing a multitude of individual mini-classifiers using sets of feature values from the samples up to a pre-selected feature size (s, integer);
  d) testing the performance of individual mini-classifiers constructed in step c) when classifying at least some of the multitude of samples and retaining those mini-classifiers whose performance exceeds a threshold or lies within preset limits to arrive at a filtered set of mini-classifiers;
  e) generating a master classifier (MC) by combining the filtered mini-classifiers using a regularized combination method;
  f) wherein the samples comprise a set of samples which are randomly separated into a test set and a training set, and wherein the steps c)-e) are repeated in the programmed computer for different realizations of the separation of the set of samples into test and training sets, thereby generating a plurality of master classifiers, one for each realization of the separation of the set of samples into training and test sets, and
  g) wherein the method further comprises the step of defining a final classifier from one or a combination of more than one of the plurality of master classifiers.

2. The method of claim 1, wherein step d) comprises repeatedly randomly selecting a small fraction of the filtered mini-classifiers and conducting logistic regression training on such selected mini-classifiers to the class labels for the samples.

3. The method of claim 1, further comprising the steps of:
  evaluating the performance of the master classifier generated at step e) on the test set of the samples,
  redefining the class labels for samples in the test set which are misclassified by the master classifier, and
  repeating steps c), d) and e) with the redefined class labels thereby generating a new master classifier.

4. The method of claim 1, wherein the samples comprise samples obtained from a human and the obtaining data comprises performing mass spectrometry on the samples and storing associated mass-spectral data in memory accessible to the programmed computer.

5. The method of claim 1, wherein the samples comprise blood-based samples from a human with cancer.

6. The method of claim 1, wherein the final classifier is defined as a majority vote of the plurality of master classifiers.

7. The method of claim 1, wherein the final classifier is defined as one of the master classifiers from one of the realizations of the separation of the set of samples into training and test sets having typical classifier performance.

8. The method of claim 1, wherein the measurement data comprises mass spectrometry data.

9. The method of claim 1, wherein the measurement data comprises gene expression, protein expression, mRNA transcript, or other genomic data.

10. The method of claim 1, wherein the method further comprises conducting a physical measurement process on a test sample to thereby obtain classification data of the same type as the physical measurement data of step a) of claim 1 and classifying the test sample using the final classifier and the classification data.

11. The method of claim 10, wherein the classification data associated with the test sample comprises a number of feature values, and wherein the method further comprising the steps of correcting the feature values associated with the test sample from a defined feature correction function to thereby produce corrected feature values, and conducting the classification of the sample using the corrected feature values.

12. The method of claim 11, wherein the method further comprises the steps of:
conducting the physical measurement process on at least one reference sample;
generating a set of reference sample feature values;
checking the reference sample feature values for concordance,
if the checking of the reference feature values for concordance is affirmative, defining a feature correction function from the reference sample feature values; and
using the feature correction function to correct the classification data for the test sample.

13. The method of claim 12, further comprising the steps of:
with the programmed computer, generating noisy feature value realizations of the corrected feature values using pre-defined feature-dependent noise characteristics;
applying the master classifier to the noisy feature value realizations;
collecting results of the applying step; and
using statistical analysis of the collected results to generate a final classification label for the test sample.

14. The method of claim 1, wherein the mini-classifiers implement a supervised classification algorithm.

15. The method of claim 1, wherein the samples are in the form of samples from a set of human patients, and wherein the method further comprises the step of redefining the class label for one or more of the samples of step a) and repeating steps c)-f) on the data associated with the multitude of samples with the redefined class labels.

16. The method of claim 15, wherein step b) comprises the further step of selecting a new set of feature values.

17. The method of claim 1, wherein the class labels of the samples of step a) have a therapeutic or diagnostics attribute.

18. A method of classifying a biological sample, comprising:
a) generating a classifier according to the method of claim 1;
b) conducting a measurement of the biological sample to thereby obtain a set of feature values pertaining to the biological sample for use in classification of the biological sample; and
c) executing in a programmed computer an application of the classifier generated in step a) to the feature values obtained in step b) and producing a class label for the biological sample.

19. The method of claim 18, wherein the biological sample is obtained from a human and wherein the step of conducting a measurement comprises conducting mass spectrometry.

20. The method of claim 19, wherein the biological sample comprises a blood-based sample.

21. The method of claim 18, wherein the class label produced in step c) comprises a prediction of whether the source of the biological sample is likely to benefit from administration of a drug or combination of drugs to treat a disease.

22. The method of claim 21, wherein the disease comprises cancer.

23. A system for generating a classifier to classify a sample, comprising:
a general purpose computer having a processing unit and a memory storing data for classification of a plurality of samples, the data for each of the samples consisting of a multitude of feature values associated with a physical measurement process and a class label, and wherein the plurality of samples are randomly separated into a test set and a training set;
and wherein the memory stores program code for:
1) constructing a multitude of individual mini-classifiers using sets of features from the samples up to a pre-selected feature set size (s, integer);
2) testing the performance of individual mini-classifiers when classifying at least some of the multitude of biological samples and retaining only those mini-classifiers whose classification performance exceeds a pre-defined threshold or lies within preset limits to arrive at a filtered set of mini-classifiers;
3) generating a master classifier by combining the filtered mini-classifiers using a regularized combination method;
4) repeating steps 1)-3) for different realizations of the separation of the set of samples into test and training sets, thereby generating a plurality of master classifiers, one for each realization of the separation of the set of samples into training and test sets, and
5) defining a final classifier from one or a combination of more than one of the plurality of master classifiers.

24. The system of claim 23, wherein the program code executing the combining step 3) repeatedly randomly selects a small fraction of the filtered mini-classifiers and conducting logistical regression training on such selected mini-classifiers to the classification labels for the samples.

25. The system of claim 23, wherein the system further comprises a mass spectrometer generating the data for classification of the samples.

26. The system of claim 23, wherein the samples comprise samples obtained from a human.

27. The system of claim 26, wherein the samples comprise blood-based samples from a human with cancer.

28. The system of claim 27, wherein the samples are obtained from cancer patients enrolled in a study to determine whether an anti-cancer drug or combination of drugs is effective in treating the cancer patients and wherein the final classifier defined by program code 5) when applied to classify data from a test sample of patient predicts whether the patient is likely to obtain relative benefit from administration of such anti-cancer drug or combination of drugs.

29. The system of claim 26, wherein the data for classification comprises mass spectrometry data.

30. The system of claim 29, wherein the mass spectrometry data is acquired from at least 20,000 shots in MALDI-TOF mass spectrometry.

31. The system of claim 23, wherein the final classifier is defined as a majority vote of the plurality of master classifiers.

32. The system of claim 23, wherein the final classifier is defined as one of the master classifiers having typical classifier performance.

33. The system of claim 23, wherein the data for classification comprises gene expression, protein expression, mRNA transcript, or other genomic data.

34. A laboratory test center comprising:
a measurement system for conducting a physical testing process on a test sample and obtain data for classification from the physical testing process in the form of values of a set of features, and
the system as recited in claim 23, wherein the programmed computer is operative to classify the data for classification obtained from the test sample using the defined final classifier.

35. The laboratory test center of claim 34, wherein the programmed computer implements a correcting of the values of features associated with the test sample from a defined feature correction function to thereby generate corrected feature values and conducts the classification of the test sample using the corrected feature values.

36. The laboratory test center of claim 35, wherein the programmed computer obtains data from at least one reference sample in addition to the obtaining data from the test sample, and wherein the programmed computer is configured to generate a set of reference sample feature values, check the reference sample feature values for concordance, and if the checking of the reference feature values for concordance is affirmative, defining a feature correction function from the reference sample feature values, and wherein the programmed computer uses the feature correction function to correct the values of features for the test sample.

37. The laboratory test center of claim 36, wherein the computer is further configured to generate noisy feature value realizations of the corrected feature values using pre-defined feature-dependent noise characteristics, apply the master classifier to the noisy feature value realizations, collect results of the applying step, and use statistical analysis of the collected results to generate a final classification label for the test sample.

38. The system of claim 23, wherein the mini-classifiers implement a supervised classification algorithm.

39. The system of claim 23, wherein the class labels of the samples have a therapeutic or diagnostics attribute.

* * * * *